(12) United States Patent
Duncton et al.

(10) Patent No.: US 9,701,647 B2
(45) Date of Patent: Jul. 11, 2017

(54) TETRAZOLONES AS A CARBOXYLIC ACID BIOISOSTERES

(71) Applicant: RIGEL PHARMACEUTICALS, INC., South San Francisco, CA (US)

(72) Inventors: Matthew Duncton, San Bruno, CA (US); Rajinder Singh, Belmont, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 15/233,676

(22) Filed: Aug. 10, 2016

(65) Prior Publication Data

US 2017/0129862 A1   May 11, 2017

Related U.S. Application Data

(63) Continuation of application No. 15/005,773, filed on Jan. 25, 2016, now Pat. No. 9,439,888.

(60) Provisional application No. 62/107,948, filed on Jan. 26, 2015.

(51) Int. Cl.

| | | |
|---|---|---|
| *C07D 257/04* | (2006.01) | |
| *A61K 31/41* | (2006.01) | |
| *C07D 403/06* | (2006.01) | |
| *C07D 403/14* | (2006.01) | |
| *C07D 401/12* | (2006.01) | |
| *C07D 403/12* | (2006.01) | |
| *C07D 401/10* | (2006.01) | |
| *C07D 413/10* | (2006.01) | |
| *C07D 501/16* | (2006.01) | |
| *C07D 401/14* | (2006.01) | |
| *C07J 43/00* | (2006.01) | |
| *C07D 401/04* | (2006.01) | |
| *C07D 487/04* | (2006.01) | |
| *C07D 471/04* | (2006.01) | |
| *A61K 31/4184* | (2006.01) | |
| *A61K 31/4709* | (2006.01) | |
| *A61K 31/4245* | (2006.01) | |
| *A61K 31/546* | (2006.01) | |
| *A61K 31/55* | (2006.01) | |
| *A61K 31/496* | (2006.01) | |
| *A61K 31/58* | (2006.01) | |
| *A61K 31/506* | (2006.01) | |
| *A61K 31/519* | (2006.01) | |

(52) U.S. Cl.
CPC .......... *C07D 257/04* (2013.01); *A61K 31/41* (2013.01); *A61K 31/4184* (2013.01); *A61K 31/4245* (2013.01); *A61K 31/4709* (2013.01); *A61K 31/496* (2013.01); *A61K 31/506* (2013.01); *A61K 31/519* (2013.01); *A61K 31/546* (2013.01); *A61K 31/55* (2013.01); *A61K 31/58* (2013.01); *C07D 401/04* (2013.01); *C07D 401/10* (2013.01); *C07D 401/12* (2013.01); *C07D 401/14* (2013.01); *C07D 403/06* (2013.01); *C07D 403/12* (2013.01); *C07D 403/14* (2013.01); *C07D 413/10* (2013.01); *C07D 471/04* (2013.01); *C07D 487/04* (2013.01); *C07D 501/16* (2013.01); *C07J 43/003* (2013.01)

(58) Field of Classification Search
CPC .. C07D 257/04; C07D 401/04; C07D 401/10; C07D 401/14; C07D 403/06; C07D 403/12; C07D 403/14; C07D 413/10; C07D 471/04; C07D 487/04; C07D 501/16; A61K 31/41; A61K 31/4184; A61K 31/4245; A61K 31/4709; A61K 31/496; A61K 31/506; A61K 31/519; A61K 31/546; A61K 31/55; A61K 31/58
USPC ....................................................... 514/230.2
See application file for complete search history.

(56) References Cited

U.S. PATENT DOCUMENTS

| | | |
|---|---|---|
| 2011/0009409 A1 | 1/2011 | Blair et al. |
| 2011/0130415 A1 | 6/2011 | Singh et al. |
| 2011/0178101 A1 | 7/2011 | Fatheree et al. |
| 2016/0083357 A1 | 3/2016 | Grether et al. |

FOREIGN PATENT DOCUMENTS

EP        0638561        5/1997

OTHER PUBLICATIONS

Ballatore et al., (2013) "Carboxylic Acid (bio) Isosteres in Drug Design," Chemmedchem 8(3): 385-395 (XP002755375).
Burger (1991) "Isosterism and Bioisosterism is Drug Research," Progress in Drug Research 37(1) 287-371 (XP002096229).
Kees et al. (1995) J. Med Chem 38: 617-628.

*Primary Examiner* — Yevegeny Valenrod
(74) *Attorney, Agent, or Firm* — Rudy J. Ng; Bozicevic, Field & Francis LLP

(57) ABSTRACT

The present disclosure provides compounds that include a tetrazolone derivative of a carboxyl group of an active agent. This disclosure also relates to pharmaceutical compositions that include these compounds, methods of using these compounds in the treatment of various diseases and disorders, and processes for preparing these compounds.

5 Claims, 2 Drawing Sheets

TETRAZOLONES AS A CARBOXYLIC ACID BIOISOSTERES

CROSS-REFERENCE TO RELATED APPLICATIONS

This application claims priority pursuant to 35 U.S.C. §119(e) to the filing date of U.S. Provisional Application No. 62/107,948, filed Jan. 26, 2015, the disclosure of which is herein incorporated by reference.

INTRODUCTION

Tetrazole is an organic heterocyclic compound that includes a 5-membered ring of four nitrogen atoms and one carbon atom (plus hydrogens), and has the chemical formula $CH_2N_4$. A tetrazol-5-one group (also referred to as "tetrazolone") includes an oxygen on the 5-position of the tetrazole ring. When the nitrogen at the 4-position of tetrazolone is unsubstituted, the tetrazolone can have a similar pKa compared to tetrazole, and can lower the calculated octanol-water partition coefficient (clog P). In addition, the presence of an oxygen on the tetrazolone ring can stabilize the localization of electron-density at the nitrogen 4-position, allowing for 1,4-disubstituted analogs. An expedient synthesis of compounds containing the tetrazolone group may be used to produce compounds containing the tetrazolone group.

SUMMARY

The present disclosure provides compounds that include a tetrazolone derivative of a carboxyl group of an active agent. In some instances, the active agent is a biologically active agent, such as, but not limited to, a pesticide, an herbicide or a therapeutically effective compound. This disclosure also relates to pharmaceutical compositions that include these compounds, methods of using these compounds in the treatment of various diseases and disorders, and processes for preparing these compounds.

In some embodiments, the tetrazolone derivative includes a tetrazolone or a substituted tetrazolone. By "tetrazolone" is meant a tetrazol-5-one group.

Embodiments of chemical structures are provided throughout the present disclosure. By way of example, such compounds are represented by the following formula:

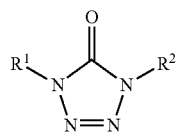

wherein
R¹ is the active agent; and
R² is selected from hydrogen, alkyl, substituted alkyl, alkenyl, substituted alkenyl, alkynyl, substituted alkynyl; or a salt or stereoisomer thereof.

In some embodiments, R² is hydrogen or alkyl.
In some embodiments, the active agent is a therapeutically effective active agent.
In some embodiments, the tetrazolone derivative is produced from the carboxyl group of the active agent.
In some embodiments, the compound is selected from:

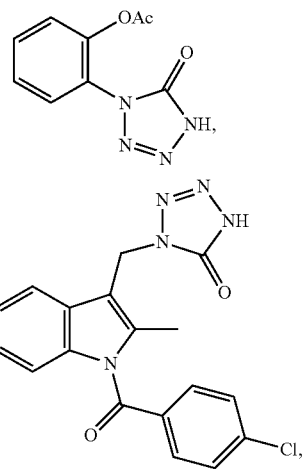

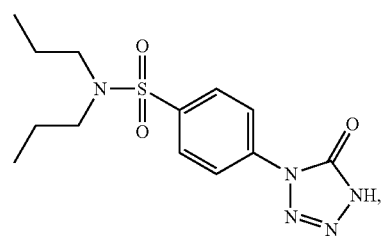

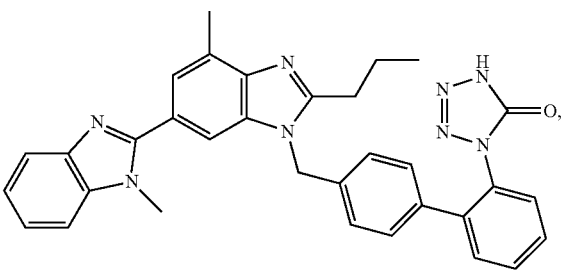

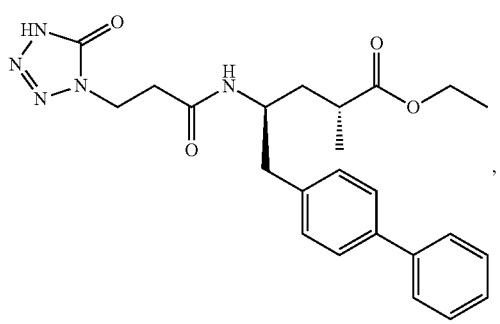

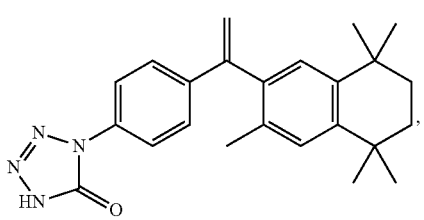

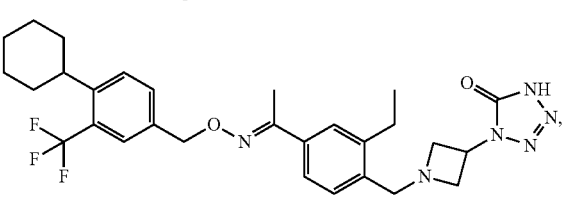

-continued
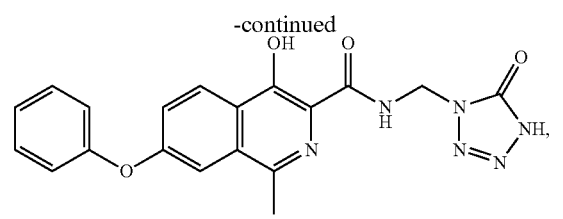
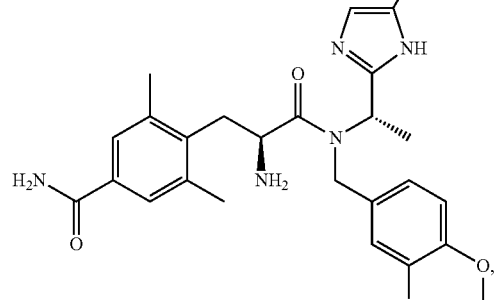
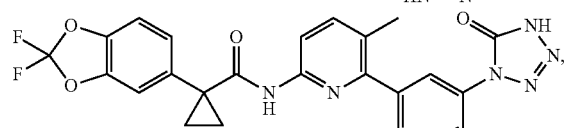
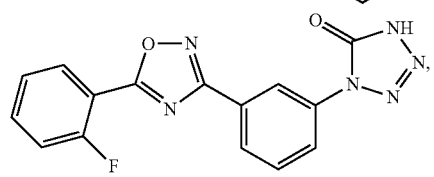
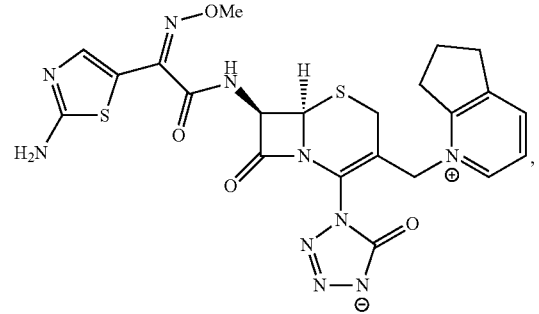
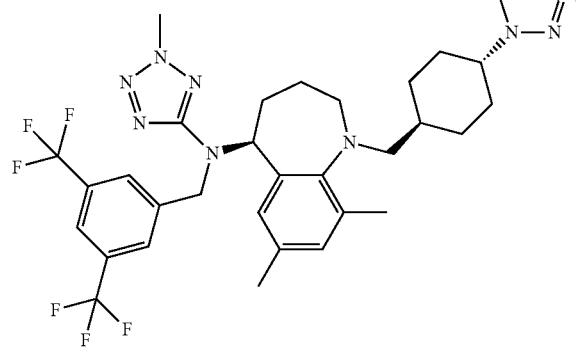
-continued
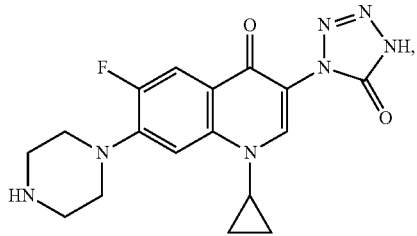
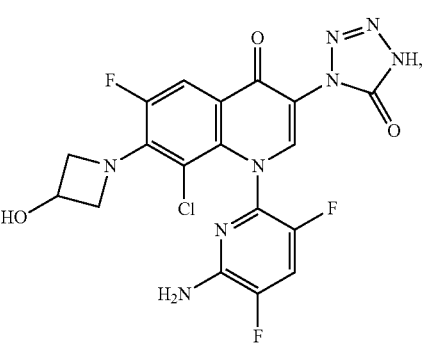
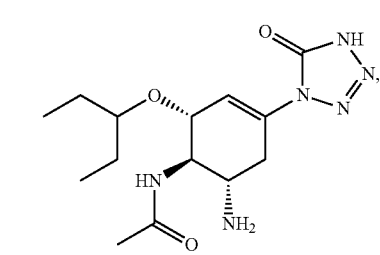
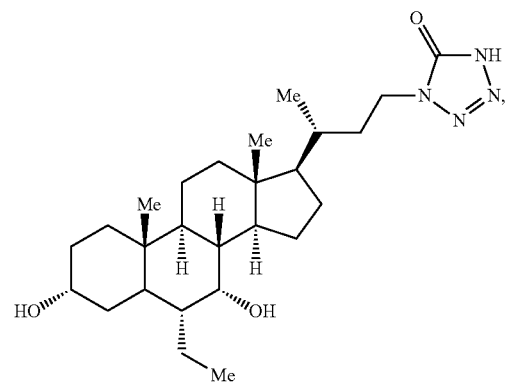
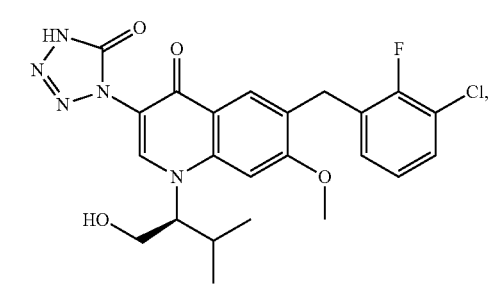

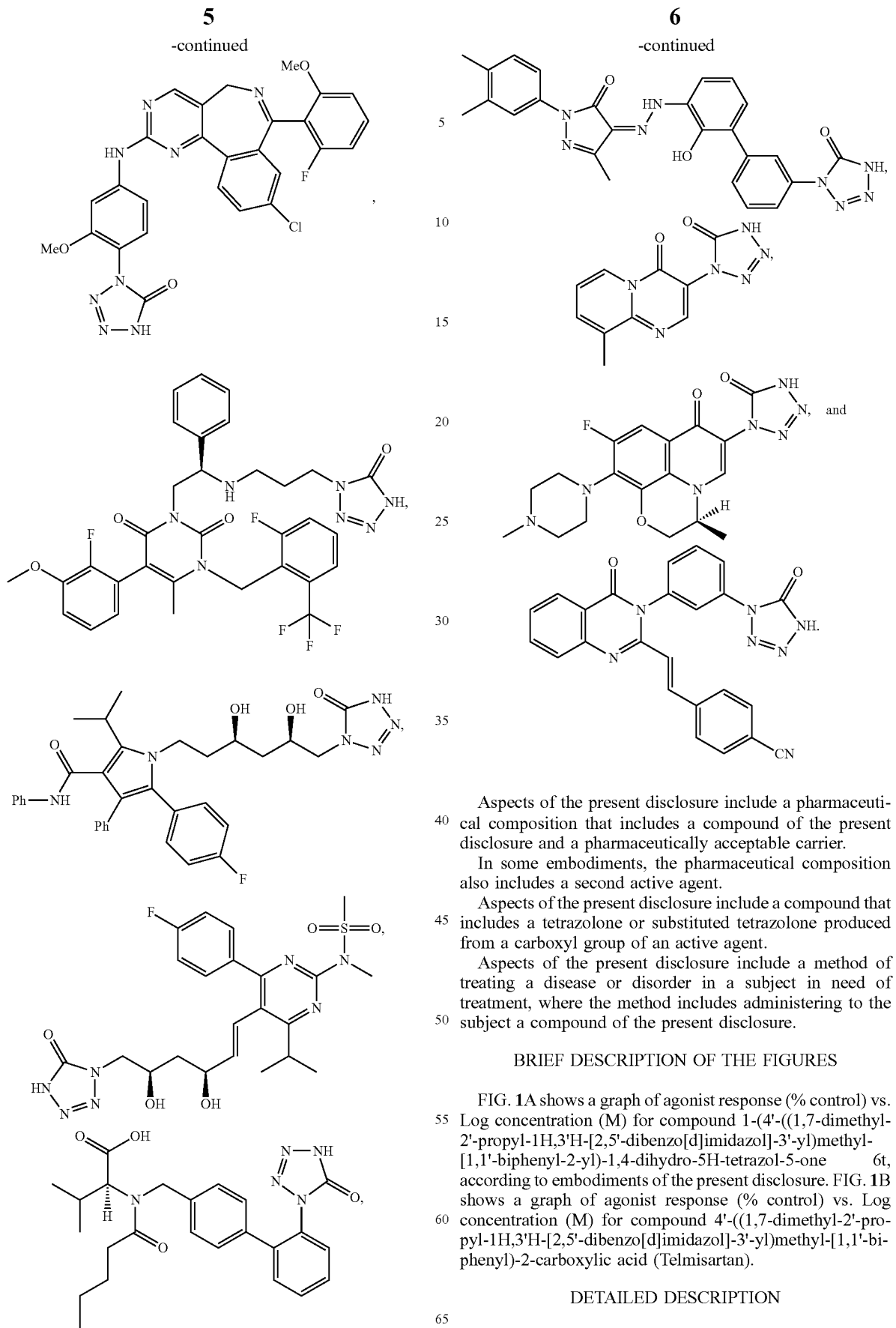

Aspects of the present disclosure include a pharmaceutical composition that includes a compound of the present disclosure and a pharmaceutically acceptable carrier.

In some embodiments, the pharmaceutical composition also includes a second active agent.

Aspects of the present disclosure include a compound that includes a tetrazolone or substituted tetrazolone produced from a carboxyl group of an active agent.

Aspects of the present disclosure include a method of treating a disease or disorder in a subject in need of treatment, where the method includes administering to the subject a compound of the present disclosure.

DETAILED DESCRIPTION

Figure 1A:
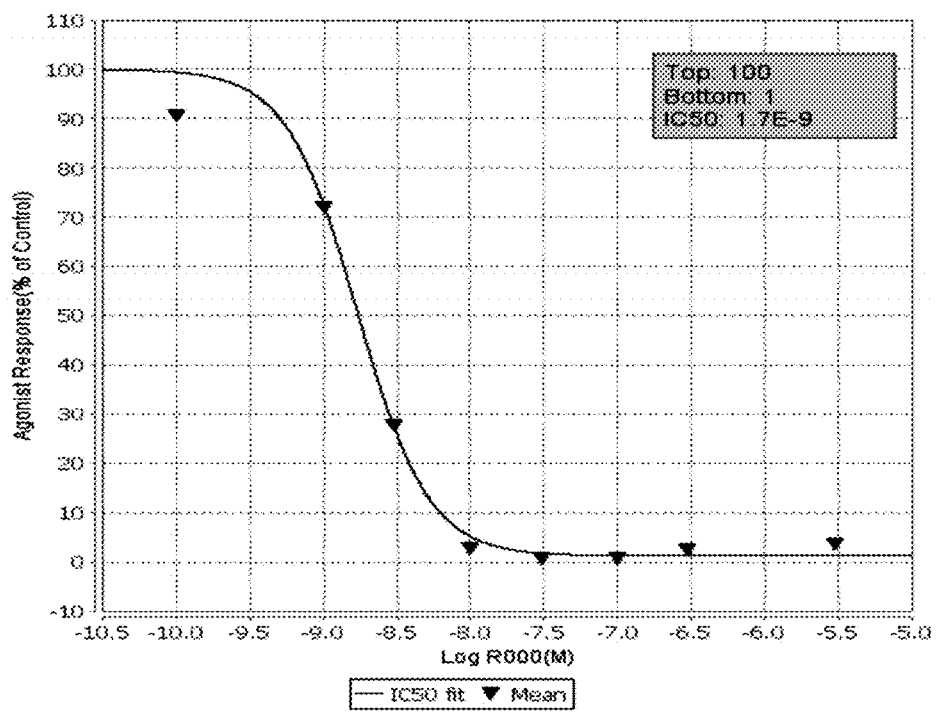
FIG. 1A shows a graph of agonist response (% control) vs. Log concentration (M) for compound 1-(4'-((1,7-dimethyl-2'-propyl-1H,3'H-[2,5'-dibenzo[d]imidazol]-3'-yl)methyl-[1,1'-biphenyl-2-yl)-1,4-dihydro-5H-tetrazol-5-one 6t, according to embodiments of the present disclosure.

The present disclosure provides compounds that include a tetrazolone derivative of a carboxyl group of an active agent.

In some instances, the active agent is a biologically active agent, such as, but not limited to, a pesticide, an herbicide or a therapeutically effective compound. This disclosure also relates to pharmaceutical compositions that include these compounds, methods of using these compounds in the treatment of various diseases and disorders, and processes for preparing these compounds.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It is noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Where a range of values is provided, it is understood that each intervening value, to the tenth of the unit of the lower limit unless the context clearly dictates otherwise, between the upper and lower limit of that range and any other stated or intervening value in that stated range, is specifically contemplated. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978.

The nomenclature used herein to name the subject compounds is illustrated in the Examples herein. This nomenclature has generally been derived using the commercially-available AutoNom software (MDL, San Leandro, Calif.).

Terms

The following terms have the following meanings unless otherwise indicated. Any undefined terms have their art recognized meanings.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—$CH_2$—), ethylene (—$CH_2CH_2$—), n-propylene (—$CH_2CH_2CH_2$—), iso-propylene (—$CH_2CH(CH_3)$—), (—$C(CH_3)_2CH_2CH_2$—), (—C($CH_3)_2CH_2C(O)$—), (—C($CH_3)_2CH_2C(O)NH$—), (—CH($CH_3)CH_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

The term "alkylaminoalkyl", "alkylaminoalkenyl" and "alkylaminoalkynyl" refers to the groups R'NHR"—where R' is alkyl group as defined herein and R" is alkylene, alkenylene or alkynylene group as defined herein.

The term "alkaryl" or "aralkyl" refers to the groups -alkylene-aryl and -substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyamino" refers to the group —NH-alkoxy, wherein alkoxy is defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups -alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—CH$_2$C≡CH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO— substituted alkyl, —SO-aryl, —SO-heteroaryl, —SO$_2$-alkyl, —SO$_2$-substituted alkyl, —SO$_2$-aryl, and —SO$_2$-heteroaryl.

"Alkynyloxy" refers to the group —O-alkynyl, wherein alkynyl is as defined herein. Alkynyloxy includes, by way of example, ethynyloxy, propynyloxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group $CH_3C(O)$—

"Acylamino" refers to the groups —NR$^{20}$C(O)alkyl, —NR$^{20}$C(O) substituted alkyl, N R$^{20}$C(O)cycloalkyl, —NR$^{20}$C(O) substituted cycloalkyl, —NR$^{20}$C(O)cycloalkenyl, —NR$^{20}$C(O) substituted cycloalkenyl, —NR$^{20}$C(O) alkenyl, —NR$^{20}$C(O) substituted alkenyl, —NR$^{20}$C(O) alkynyl, —NR$^{20}$C(O) substituted alkynyl, —NR$^{20}$C(O)aryl, —NR$^{20}$C(O) substituted aryl, —NR$^{20}$C(O)heteroaryl, —NR$^{20}$C(O) substituted heteroaryl, —NR$^{20}$C(O)heterocyclic, and —NR$^{20}$C(O) substituted heterocyclic, wherein R$^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^{21}$C(O) NR$^{22}$R$^{23}$ where R$^{21}$, R$^{22}$, and R$^{23}$ are independently selected from hydrogen, alkyl, aryl or cycloalkyl, or where two R groups are joined to form a heterocyclyl group.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

"Aminosulfonyl" refers to the group —SO$_2$NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where $R^{21}$ and $R^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —NR$^{21}$SO$_2$R$^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

"Aryloxy" refers to the group —O-aryl, wherein aryl is as defined herein, including, by way of example, phenoxy, naphthoxy, and the like, including optionally substituted aryl groups as also defined herein.

"Amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —N$_3$.

"Carboxyl," "carboxy" or "carboxylate" refers to —CO$_2$H or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O-alkyl, —O—C(O)O-substituted alkyl, —O—C(O)O-alkenyl, —O—C(O)O-substituted alkenyl, —O—C(O)O— alkynyl, —O—C(O)O-substituted alkynyl, —O—C(O)O-aryl, —O—C(O)O-substituted aryl, —O—C(O)O—cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkenyl" refers to non-aromatic cyclic alkyl groups of from 3 to 10 carbon atoms having single or multiple rings and having at least one double bond and preferably from 1 to 2 double bonds.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkynyl" refers to non-aromatic cycloalkyl groups of from 5 to 10 carbon atoms having single or multiple rings and having at least one triple bond.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$— alkyl, —SO$_2$-substituted alkyl, —SO$_2$-aryl and —SO$_2$-heteroaryl, and trihalomethyl.

The term "heteroaralkyl" refers to the groups -alkylene-heteroaryl where alkylene and heteroaryl are defined herein. This term includes, by way of example, pyridylmethyl, pyridylethyl, indolylmethyl, and the like.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocylooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Heterocyclyloxy" refers to the group —O-heterocyclyl.

The term "heterocyclylthio" refers to the group heterocyclic-S—.

The term "heterocyclene" refers to the diradical group formed from a heterocycle, as defined herein.

The term "hydroxyamino" refers to the group —NHOH.

"Nitro" refers to the group —NO$_2$.

"Oxo" refers to the atom (=O).

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cycloalkyl, SO$_2$-cycloalkenyl, SO$_2$-substituted cylcoalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

"Sulfonyloxy" refers to the group —OSO$_2$-alkyl, OSO$_2$-substituted alkyl, OSO$_2$-alkenyl, OSO$_2$-substituted alkenyl, OSO$_2$-cycloalkyl, OSO$_2$-substituted cycloalkyl, OSO$_2$-cycloalkenyl, OSO$_2$-substituted cylcoalkenyl, OSO$_2$-aryl, OSO$_2$-substituted aryl, OSO$_2$-heteroaryl, OSO$_2$-substituted heteroaryl, OSO$_2$-heterocyclic, and OSO$_2$ substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioxo" or the term "thioketo" refers to the atom (=S).

"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

The term "substituted thioalkoxy" refers to the group —S-substituted alkyl.

The term "thioaryloxy" refers to the group aryl-S— wherein the aryl group is as defined herein including optionally substituted aryl groups also defined herein.

The term "thioheteroaryloxy" refers to the group heteroaryl-S— wherein the heteroaryl group is as defined herein including optionally substituted aryl groups as also defined herein.

The term "thioheterocyclooxy" refers to the group heterocyclyl-S— wherein the heterocyclyl group is as defined herein including optionally substituted heterocyclyl groups as also defined herein.

The term "pentafluorosulfanyl" refers to the group —$SF_5$.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =$NR^{70}$, =N—$OR^{70}$, =$N_2$ or =S) on saturated carbon atoms in the specified group or radical are, unless otherwise specified, —$R^{60}$, halo, =O, —$OR^{70}$, —$SR^{70}$, —$NR^{80}R^{80}$, trihalomethyl, —CN, —OCN, —SCN, —NO, —$NO_2$, =$N_2$, —$N_3$, —$SO_2R^{70}$, —$SO_2O^-M^+$, —$SO_2OR^{70}$, —$OSO_2R^{70}$, —$OSO_2O^-M^+$, —$OSO_2OR^{70}$, —$P(O)(O^-)_2(M^+)_2$, —$P(O)(OR^{70})O^-M^+$, —$P(O)(OR^{70})_2$, —$C(O)R^{70}$, —$C(S)R^{70}$, —$C(NR^{70})R^{70}$, —$C(O)O^-M^+$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)O^-M^+$, —$OC(O)OR^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each $R^{70}$ is independently hydrogen or $R^{60}$; each $R^{80}$ is independently $R^{70}$ or alternatively, two $R^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution; and each $M^+$ is a counter ion with a net single positive charge. Each $M^+$ may independently be, for example, an alkali ion, such as $K^+$, $Na^+$, $Li^+$; an ammonium ion, such as $^+N(R^{60})_4$; or an alkaline earth ion, such as $[Ca^{2+}]_{0.5}$, $[Mg^{2+}]_{0.5}$, or $[Ba^{2+}]_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —$NR^{80}R^{80}$ is meant to include —$NH_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —$R^{60}$, halo, —$O^-M^+$, —$OR^{70}$, —$SR^{70}$, —$S^-M^+$, —$NR^{80}R^{80}$, trihalomethyl, —$CF_3$, —CN, —OCN, —SCN, —NO, —$NO_2$, —$N_3$, —$SO_2R^{70}$, —$SO_3^-M^+$, —$SO_3R^{70}$, —$OSO_2R^{70}$, —$OSO_3^-M^+$, —$OSO_3R^{70}$, —$PO_3^{-2}(M^+)_2$, —$P(O)(OR^{70})O^-M^+$, —$P(O)(OR^{70})_2$, —$C(O)R^{70}$, —$C(S)R^{70}$, —$C(NR^{70})R^{70}$, —$CO_2^-M^+$, —$CO_2R^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OCO_2^-M^+$, —$OCO_2R^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined, provided that in case of substituted alkene or alkyne, the substituents are not —$O^-M^+$, —$OR^{70}$, —$SR^{70}$, or —$S^-M^+$.

In addition to the groups disclosed with respect to the individual terms herein, substituent groups for hydrogens on nitrogen atoms in "substituted" heteroalkyl and cycloheteroalkyl groups are, unless otherwise specified, —$R^{60}$, —$O^-M^+$, —$OR^{70}$, —$SR^{70}$, —$S^-M^+$, —$NR^{80}R^{80}$, trihalomethyl, —$CF_3$, —CN, —NO, —$NO_2$, —$S(O)_2R^{70}$, —$S(O)_2O^-M^+$, —$S(O)_2OR^{70}$, —$OS(O)_2R^{70}$, —$OS(O)_2O^-M^+$, —$OS(O)_2OR^{70}$, —$P(O)(O^-)_2(M^+)_2$, —$P(O)(OR^{70})O^-M^+$, —$P(O)(OR^{70})(OR^{70})$, —$C(O)R^{70}$, —$C(S)R^{70}$, —$C(NR^{70})R^{70}$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)OR^{70}$, —$OC(S)OR^{70}$, —$NR^{70}C(O)R^{70}$, —$NR^{70}C(S)R^{70}$, —$NR^{70}C(O)OR^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

"Pharmaceutically effective" and "therapeutically effective" refer to a compound (e.g., active agent) used to treat a specified disorder or disease or one or more of its symptoms and/or to prevent the occurrence of the disease or disorder. For example, in reference to tumorigenic proliferative disorders, treatment with a pharmaceutically or therapeutically effective compound (active agent) is sufficient to, among other things, cause the tumor to shrink or decrease the growth rate of the tumor.

"Pharmaceutically effective amount" and "therapeutically effective amount" refer to an amount of a compound (e.g., active agent) sufficient to treat a specified disorder or disease or one or more of its symptoms and/or to prevent the occurrence of the disease or disorder. For example, in reference to tumorigenic proliferative disorders, a pharmaceutically or therapeutically effective amount comprises an amount sufficient to, among other things, cause the tumor to shrink or decrease the growth rate of the tumor.

"Patient" refers to human and non-human subjects, especially mammalian subjects.

The term "treating" or "treatment" as used herein means the treating or treatment of a disease or medical condition in a patient, such as a mammal (particularly a human) that includes: (a) preventing the disease or medical condition from occurring, such as, prophylactic treatment of a subject; (b) ameliorating the disease or medical condition, such as, eliminating or causing regression of the disease or medical condition in a patient; (c) suppressing the disease or medical condition, for example by, slowing or arresting the development of the disease or medical condition in a patient; or (d) alleviating a symptom of the disease or medical condition in a patient.

Representative Embodiments

The following substituents and values are intended to provide representative examples of various aspects and embodiments. These representative values are intended to further define and illustrate such aspects and embodiments and are not intended to exclude other embodiments or to limit the scope of the present disclosure. In this regard, the representation that a particular value or substituent is preferred is not intended in any way to exclude other values or substituents from the present disclosure unless specifically indicated.

These compounds may contain one or more chiral centers and therefore, the embodiments are directed to racemic mixtures; pure stereoisomers (i.e., enantiomers or diastereomers); stereoisomer-enriched mixtures and the like unless otherwise indicated. When a particular stereoisomer is shown or named herein, it will be understood by those skilled in the art that minor amounts of other stereoisomers may be present in the compositions unless otherwise indicated, provided that the desired utility of the composition as a whole is not eliminated by the presence of such other isomers.

The compositions of the present disclosure include compounds as shown below. Pharmaceutical compositions and methods of the present disclosure also contemplate compounds as provided herein.

Embodiments of the present disclosure include a compound having a tetrazolone derivative of a carboxyl group of an active agent. By "derivative" is meant a compound that can be produced from a precursor compound by a chemical process. For example, an atom or group of atoms in the precursor compound can be modified or replaced to produce the derivative compound (also referred to herein as an "analog" or "structural analog"). In certain embodiments, an active agent includes a carboxyl group. Compounds of the present disclosure may be derivatives of an active agent that includes a carboxyl group. In certain embodiments, the carboxyl group of the active agent is modified or replaced to produce the derivative. For example, the carboxyl group of the active agent may be modified or replaced with a tetrazolone or a substituted tetrazolone. In these embodiments, the compounds of the present disclosure include a tetrazolone (or substituted tetrazolone) derivative of a carboxyl group of the active agent. As such, aspects of the present disclosure include compounds having a tetrazolone or substituted tetrazolone produced from a carboxyl group of an active agent.

In certain embodiments, the tetrazolone derivative is produced from a carboxyl group of the active agent. The carboxyl group of the active agent may be modified or replaced to form the tetrazolone derivative. In some cases, the carboxyl group is modified to produce one or more intermediate groups before producing the tetrazolone derivative. In certain instances, such intermediate groups include, but are not limited to, an acyl halide (i.e., acid halide), an isocyanate, an acyl azide, and the like. In some embodiments, the acyl halide intermediate is an acyl chloride (acid chloride).

In certain embodiments, the tetrazolone derivative includes a tetrazolone or a substituted tetrazolone. By "tetrazolone" is meant a tetrazol-5-one group. In some cases, the tetrazolone derivative is tetrazolone (e.g., an unsubstituted tetrazolone, such as a tetrazolone that has a hydrogen at the 4-position). In some cases, the tetrazolone derivative is a substituted tetrazolone, such as a 1,4-disubstituted tetrazolone. Substituents of interest include, but are not limited to, alkyl, substituted alkyl, alkenyl, substituted alkenyl, alkynyl, and substituted alkynyl.

In certain embodiments, the substituted tetrazolone includes an alkyl substituent, such as, but not limited to a $C_{1-6}$ alkyl, a $C_{1-5}$ alkyl, $C_{1-4}$ alkyl, $C_{1-3}$ alkyl, or $C_{1-2}$ alkyl. In some embodiments, the substituted tetrazolone includes a $C_{1-3}$ alkyl, such as methyl. In certain embodiments, the substituted tetrazolone includes a substituted alkyl substituent, such as, but not limited to a substituted $C_{1-6}$ alkyl, a substituted $C_{1-5}$ alkyl, substituted $C_{1-4}$ alkyl, substituted $C_{1-3}$ alkyl, or substituted $C_{1-2}$ alkyl. In some embodiments, the substituted tetrazolone includes a substituted $C_{1-3}$ alkyl, such as substituted methyl.

In certain embodiments, the substituted tetrazolone includes an alkenyl substituent, such as, but not limited to a $C_{1-6}$ alkenyl, a $C_{1-5}$ alkenyl, $C_{1-4}$ alkenyl, $C_{1-3}$ alkenyl, or $C_{1-2}$ alkenyl. In some embodiments, the substituted tetrazolone includes a $C_{1-3}$ alkenyl. In certain embodiments, the substituted tetrazolone includes a substituted alkenyl substituent, such as, but not limited to a substituted $C_{1-6}$ alkenyl, a substituted $C_{1-5}$ alkenyl, substituted $C_{1-4}$ alkenyl, substituted $C_{1-3}$ alkenyl, or substituted $C_{1-2}$ alkenyl. In some embodiments, the substituted tetrazolone includes a substituted $C_{1-3}$ alkenyl.

In certain embodiments, the substituted tetrazolone includes an alkynyl substituent, such as, but not limited to a $C_{1-6}$ alkynyl, a $C_{1-5}$ alkynyl, $C_{1-4}$ alkynyl, $C_{1-3}$ alkynyl, or $C_{1-2}$ alkynyl. In some embodiments, the substituted tetrazolone includes a $C_{1-3}$ alkynyl. In certain embodiments, the substituted tetrazolone includes a substituted alkynyl substituent, such as, but not limited to a substituted $C_{1-6}$ alkynyl, a substituted $C_{1-5}$ alkynyl, substituted $C_{1-4}$ alkynyl, substituted $C_{1-3}$ alkynyl, or substituted $C_{1-2}$ alkynyl. In some embodiments, the substituted tetrazolone includes a substituted $C_{1-3}$ alkynyl.

In certain embodiments, the compound is of the following formula:

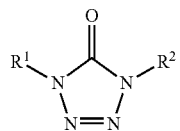

wherein
$R^1$ is the active agent; and
$R^2$ is selected from hydrogen, alkyl, substituted alkyl, alkenyl, substituted alkenyl, alkynyl, substituted alkynyl;
or a salt or stereoisomer thereof.

In certain embodiments, $R^1$ is the active agent. In some cases, the active agent is an agrochemical, such as an herbicide. In some instances, the active agent is a therapeutically effective active agent. For example, $R^1$ may be any of the active agents described below. As discussed herein, a carboxyl group of the active agent may be replaced by a bond between $R^1$ and the tetrazolone or substituted tetrazolone group, as shown in the formula above.

In some embodiments, $R^2$ is selected from hydrogen, alkyl, substituted alkyl, alkenyl, substituted alkenyl, alkynyl, substituted alkynyl. In some embodiments, $R^2$ is hydrogen. In some embodiments, $R^2$ is alkyl or substituted alkyl. In some embodiments, $R^2$ is alkenyl or substituted alkenyl. In some embodiments, $R^2$ is alkynyl or substituted alkynyl.

In some embodiments, $R^2$ is hydrogen, alkyl or substituted alkyl. In some embodiments, $R^2$ is hydrogen or alkyl. In some embodiments, $R^2$ is alkyl (e.g., methyl).

In certain embodiments, $R^2$ is alkyl, such as, but not limited to a $C_{1-6}$ alkyl, $C_{1-5}$ alkyl, $C_{1-4}$ alkyl, $C_{1-3}$ alkyl, or $C_{1-2}$ alkyl. In some embodiments, $R^2$ is $C_{1-3}$ alkyl, such as methyl. In certain embodiments, $R^2$ is substituted alkyl, such as substituted $C_{1-6}$ alkyl, substituted $C_{1-5}$ alkyl, substituted $C_{1-4}$ alkyl, substituted $C_{1-3}$ alkyl, or substituted $C_{1-2}$ alkyl. In some embodiments, $R^2$ is substituted $C_{1-3}$ alkyl, such as substituted methyl.

In certain embodiments, $R^2$ is alkenyl, such as, but not limited to a $C_{1-6}$ alkenyl, $C_{1-5}$ alkenyl, $C_{1-4}$ alkenyl, $C_{1-3}$ alkenyl, or $C_{1-2}$ alkenyl. In some embodiments, $R^2$ is $C_{1-3}$ alkenyl. In certain embodiments, $R^2$ is substituted alkenyl, such as, but not limited to a substituted $C_{1-6}$ alkenyl, substituted $C_{1-5}$ alkenyl, substituted $C_{1-4}$ alkenyl, substituted $C_{1-3}$ alkenyl, or substituted $C_{1-2}$ alkenyl. In some embodiments, $R^2$ is substituted $C_{1-3}$ alkenyl.

In certain embodiments, $R^2$ is alkynyl, such as, but not limited to a $C_{1-6}$ alkynyl, a $C_{1-5}$ alkynyl, $C_{1-4}$ alkynyl, $C_{1-3}$ alkynyl, or $C_{1-2}$ alkynyl. In some embodiments, $R^2$ is $C_{1-3}$ alkynyl. In certain embodiments, $R^2$ is substituted alkynyl, such as, but not limited to a substituted $C_{1-6}$ alkynyl, substituted $C_{1-5}$ alkynyl, substituted $C_{1-4}$ alkynyl, substituted $C_{1-3}$ alkynyl, or substituted $C_{1-2}$ alkynyl. In some embodiments, $R^2$ is substituted $C_{1-3}$ alkynyl.

In certain embodiments, the compound is optically active. In certain embodiments, there is an enantiomeric excess of 90% or more. In certain embodiments, there is an enantiomeric excess of 95% or more. In certain embodiments, there is an enantiomeric excess of 99% or more.

Particular compounds of interest, and salts or solvates or stereoisomers thereof, include:

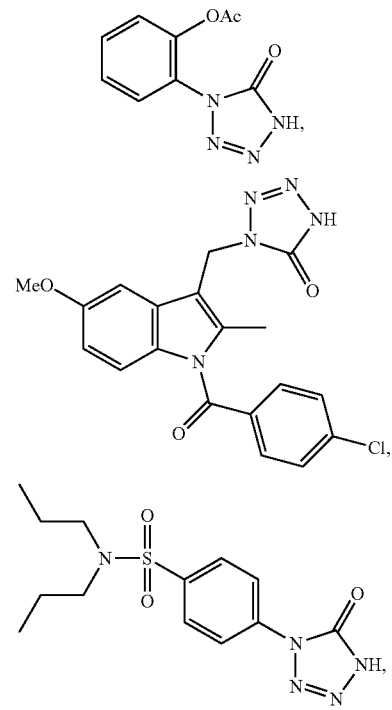

21
-continued
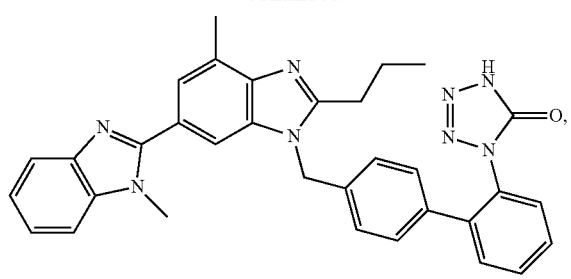
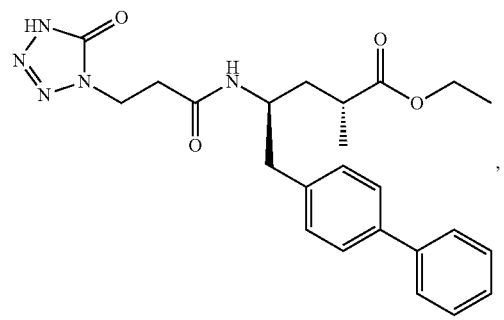
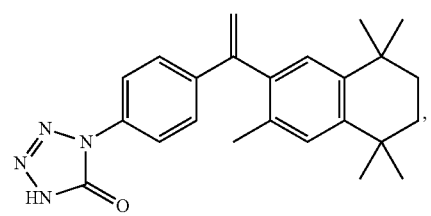
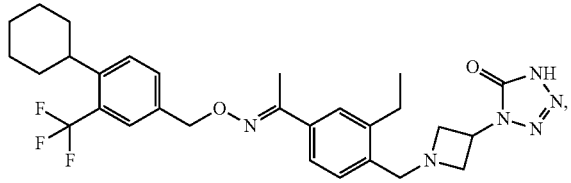
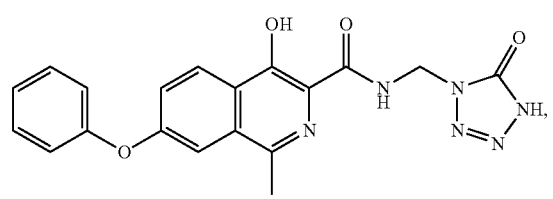
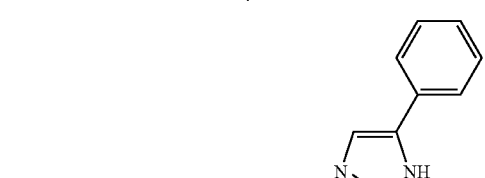
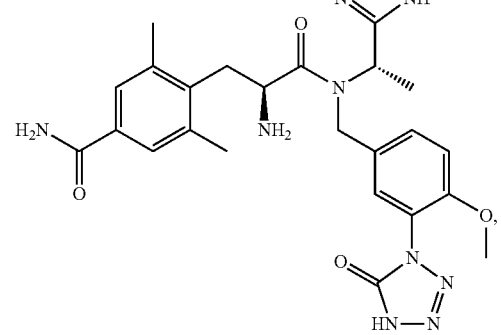
22
-continued
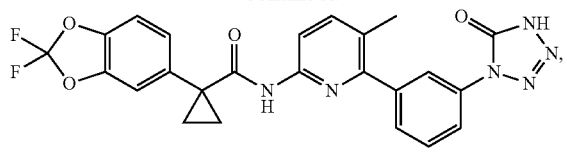
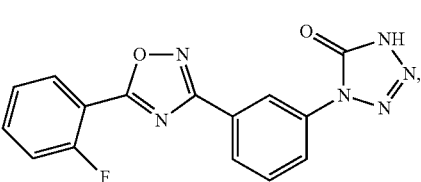
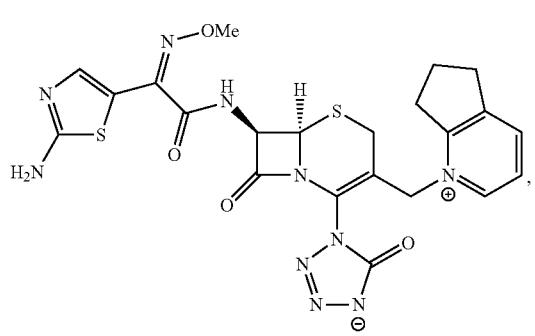
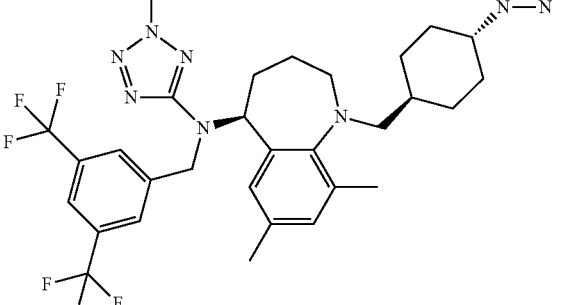
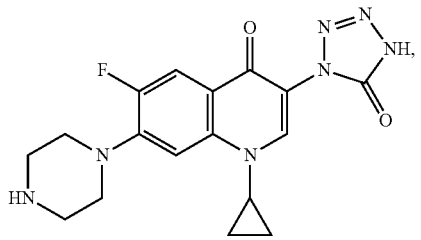
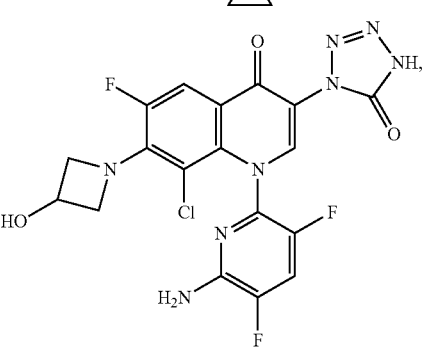

23
-continued
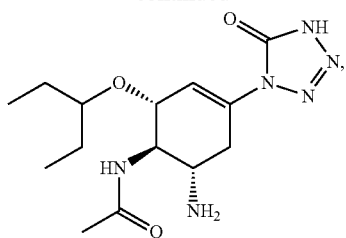
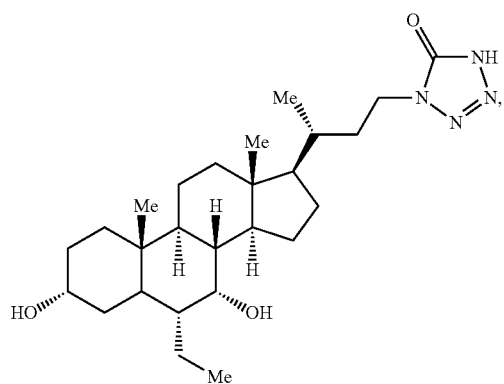
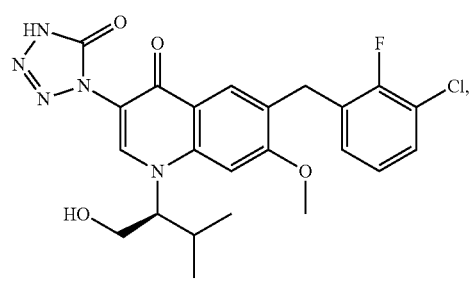
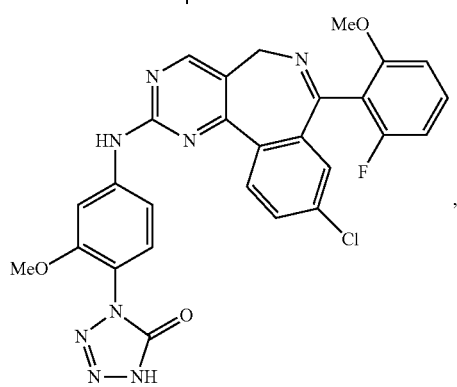
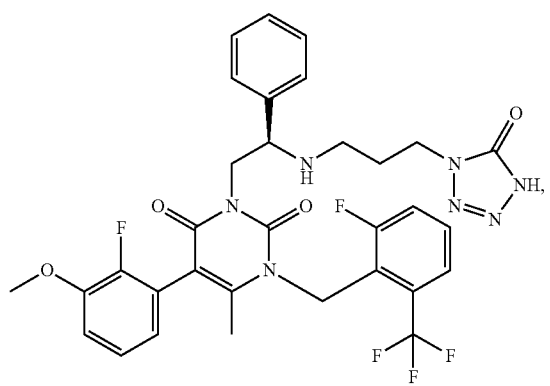
24
-continued
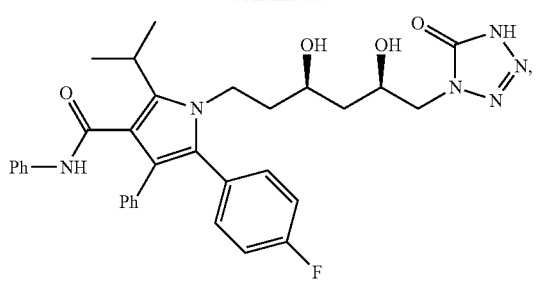
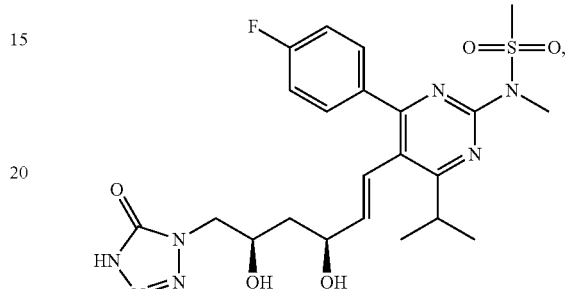
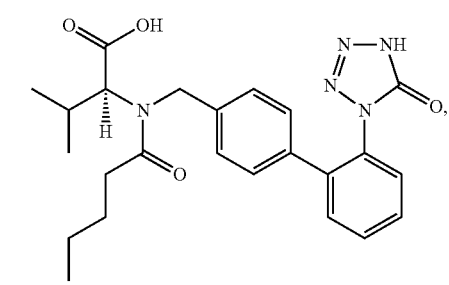
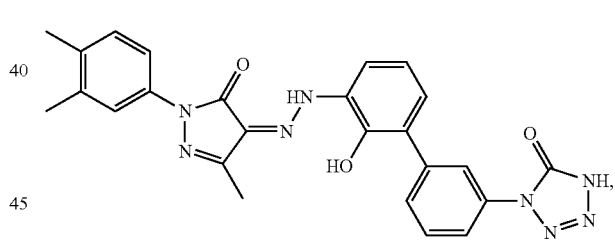
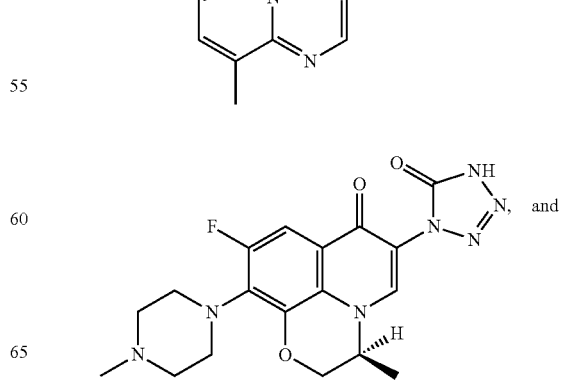

-continued

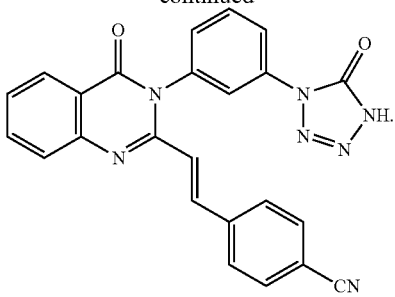

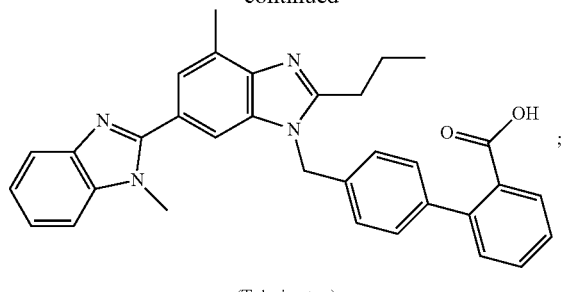

(Telmisartan)

In certain embodiments, compounds of the present disclosure are isosteres (e.g., bioisosteres) of active agents that include a carboxyl group. By "isostere" or "bioisostere" is meant a derivative of an active agent (e.g., a therapeutically effective active agent), where the derivative produces substantially similar biological effects in vivo as compared to the active agent. In some embodiments, compounds of the present disclosure include a tetrazolone or substituted tetrazolone and are isosteres (e.g., bioisosteres) of an active agent (e.g., a therapeutically effective active agent) that includes a carboxyl group.

As described herein, a compound of the present disclosure may be a tetrazolone derivative of an active agent (or prodrug of an active agent), such as a tetrazolone-containing isostere or bioisostere of an active agent (or prodrug of an active agent) having a carboxyl group. In some instances, the active agent is a biologically active agent, such as, but not limited to, a pesticide, an herbicide or a therapeutically effective compound. In some embodiments, the active agent is a therapeutically effective active agent, such as, but not limited to the following:

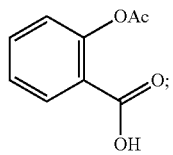

(Aspirin)

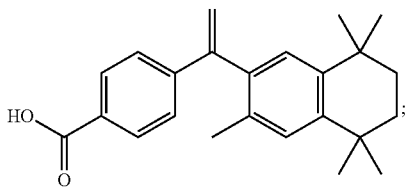

(Sacubitril)

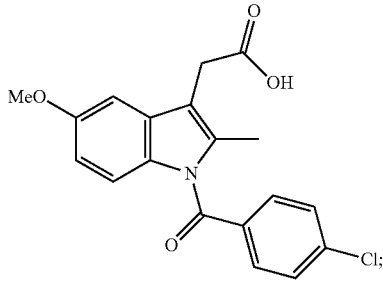

(Indomethacin)

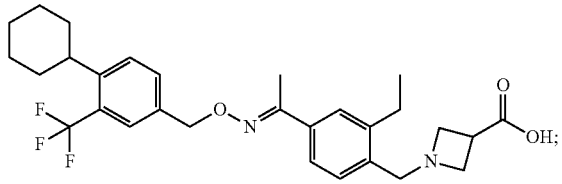

(Bexarotene)

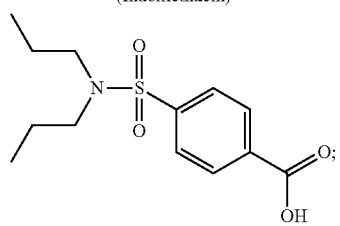

(Probenecid)

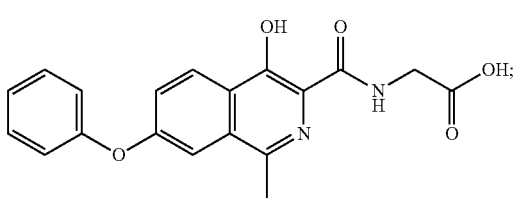

(Siponimod)

(FG-4592)

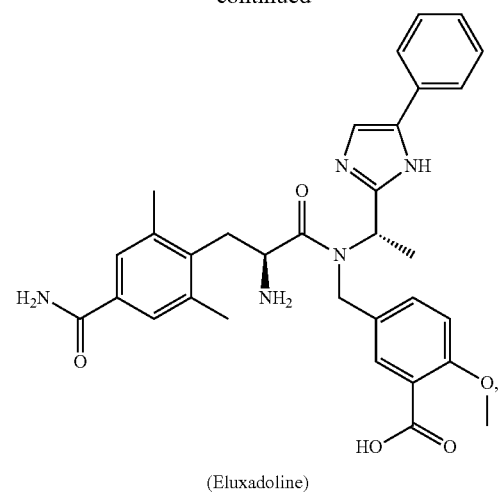
(Eluxadoline)
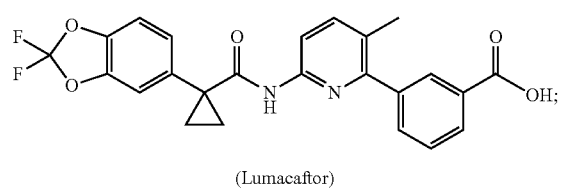
(Lumacaftor)
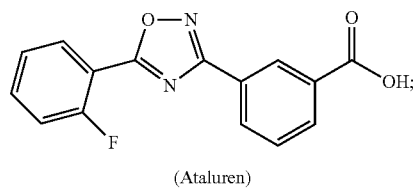
(Ataluren)
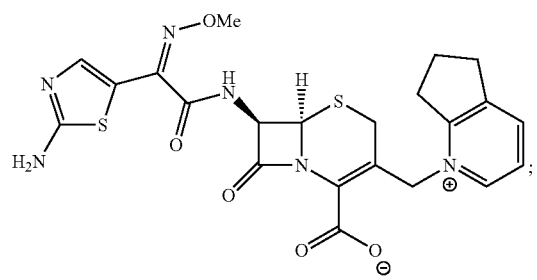
(Cefpirome)
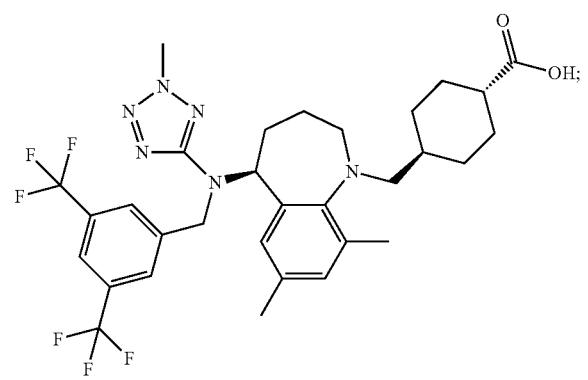
(Evacetrapib)
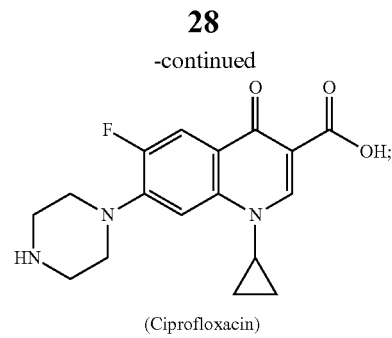
(Ciprofloxacin)
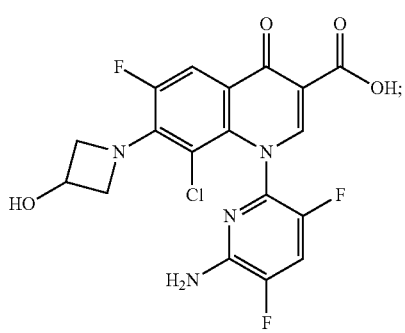
(Delafloxacin)
or
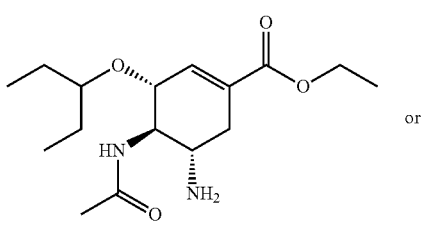
(Oseltamivir)
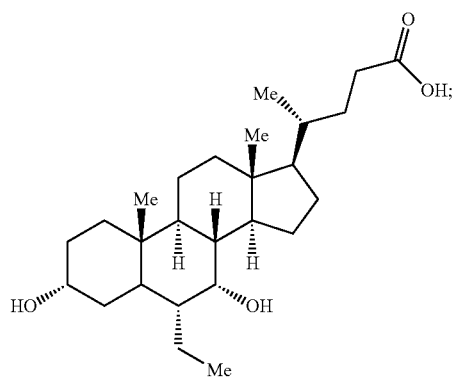
(Obeticholic acid)

-continued
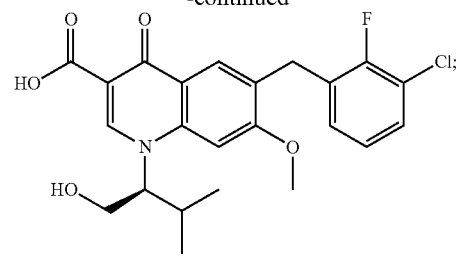
(Elvitegravir)
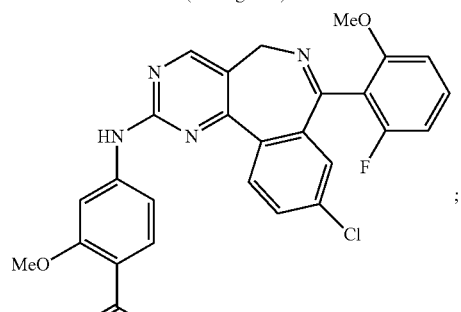
(Alisertib)
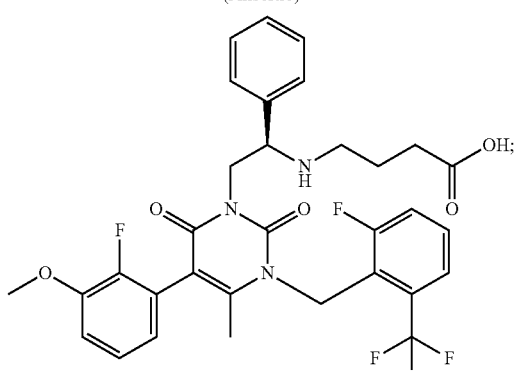
(Elagolix)
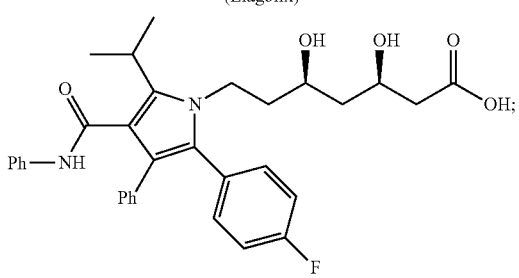
(Atorvastain)
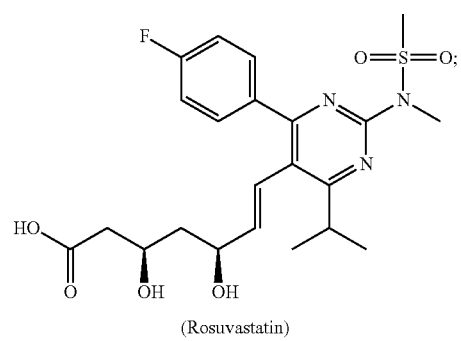
(Rosuvastatin)
-continued
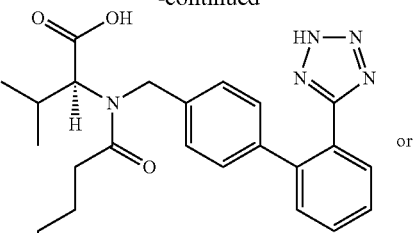
or
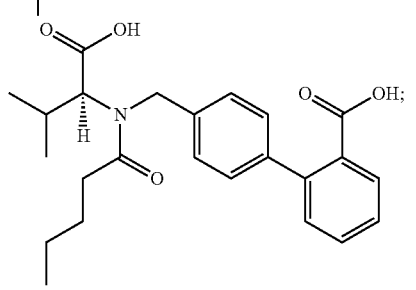
(Valsartan)
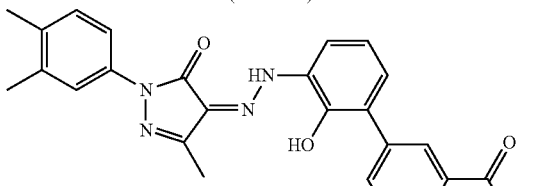
(Eltrombopag)
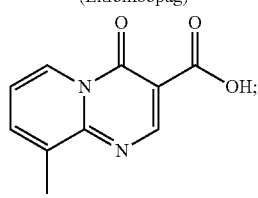
(Pemirolast)
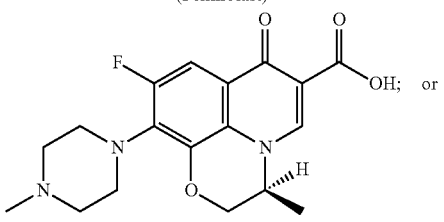
or
(Levofloxacin)
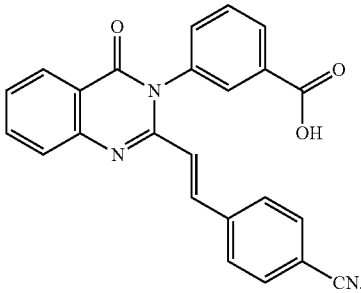
((E)-3-(2-(4-cyanostyryl)-4-oxoquinazolin-3(4H)-yl)benzoic acid)
The compounds described herein also include isotopically labeled compounds where one or more atoms have an atomic mass different from the atomic mass conventionally found in nature. Examples of isotopes that may be incorporated into the compounds disclosed herein include, but are not limited to, $^{2}H$, $^{3}H$, $^{11}C$, $^{13}C$, $^{14}C$, $^{15}N$, $^{18}O$, $^{17}O$, etc. Thus, the disclosed compounds may be enriched in one or more of these isotopes relative to the natural abundance of such isotope. By way of example, deuterium ($^{2}H$) has a natural abundance of about 0.015%. Accordingly, for approximately every 6,500 hydrogen atoms occurring in nature, there is one deuterium atom. Specifically contemplated herein are compounds enriched in deuterium at one or more positions. Thus, deuterium containing compounds of the disclosure have deuterium at one or more positions (as the case may be) in an abundance of greater than 0.015%.

General Synthetic Procedures

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any purification protocol known in the art, including chromatography, such as HPLC, preparative thin layer chromatography, flash column chromatography and ion exchange chromatography. Any suitable stationary phase can be used, including normal and reversed phases as well as ionic resins. In certain embodiments, the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4$^{th}$ edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

Examples of synthetic methods for the compounds provided herein are described in the schemes below. These methods can be adapted to synthesize compounds and prodrugs described herein.

Synthesis of Compounds

In certain embodiments, the compounds can be synthesized according to one or more of the steps of the scheme shown below:

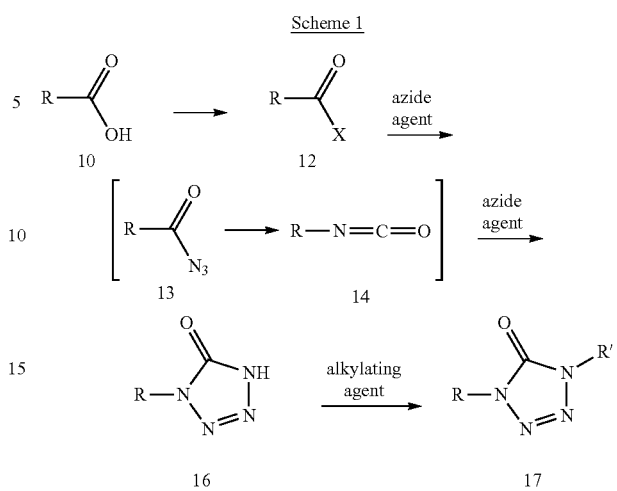

Scheme 1 where compound 10 is a carboxylic acid-containing compound of interest, compound 12 includes an activated acyl group (e.g., X is an acyl activating group, such as a leaving group), acyl azide compound 13 and isocyanate compound 14 may be formed in situ or may be isolated starting compounds, and tetrazolone 16 may be optionally further derivatized using any convenient method, e.g., with an alkylating agent to produce to tetrazolone 17, where R' is an alkyl or a substituted alkyl group. The selection of a suitable starting compound depends on a variety of factors, such as the desired product. Alternatively, compound 10 may be converted directly to intermediate acyl azide compound 13 via a single reagent, such as diphenyl phosphoryl azide.

In some embodiments, R—CO$_{2}$H (10) is a bioactive compound of interest (e.g., as described herein). Bioactive compounds of interest which may be converted into tetrazolone compounds according to the methods described herein include, but are not limited to, amino acids, peptides, nutrients (e.g., Vitamin B), natural products or semi-synthetic drugs (e.g., penicillins, cephalosporins, carbapenems, etc.), antibiotics, such as quinolone antibiotics (e.g., Ciprofloxacin, ABT-492) or quinazolinone antibiotics (e.g., (E)-3-(2-(4-cyanostyryl)-4-oxoquinazolin-3(4H)-yl)benzoic acid), insulin secretors, such as "Metliginides" (e.g., Repaglinide), non-steroidal anti-inflammatories (e.g., Ibuprofen, Naproxen, etc.), "Statins" (e.g., Atorvastatin), CFTR "Correctors" & Read-Through Enablers for nmStops (e.g., Lumacaftor (VX-809)/Ataluren) and antiviral compounds (e.g., Elvitegravir (GS-9137)). In some instances, rather than converting a carboxylic acid group of a carboxylic acid-containing active agent to a tetrazolone group, the tetrazolone derivative of the active agent may be synthesized using a tetrazolone-containing precursor.

In certain embodiments, R is a fragment or a synthetic precursor of a compound of interest and may further include any convenient additional functional groups (e.g., protected or unprotected functional groups) suitable for use in the synthesis of compounds of interest. A variety of chemical synthetic schemes and conditions useful for synthesizing such compounds are available. As such, the tetrazolone group of the subject compounds may be installed at any convenient point in the synthesis of a target compound of interest. In some instances, the tetrazolone group is installed at the end of the synthesis, e.g., where R represents a bioactive moiety, or a protected version thereof. In certain instances, the tetrazolone group is installed into a compound R, which is a convenient fragment or precursor of a target compound of interest.

Any convenient tetrazolone precursor of scheme 1 (i.e., compounds 10, 12, 13 or 14 including any convenient R group of interest) may be utilized as a starting compound in the preparation of the subject tetrazolone compound 16. In some cases, one of compounds 12, 13 or 14 is provided as a starting compound for the synthesis of compound 16, where the compounds 12, 13 or 14 may be derived from a carboxylic acid (10) or from another convenient precursor.

R may include any convenient additional functional groups (e.g., protected or unprotected functional groups), that are stable to the methods of preparing the subject tetrazolone compounds. In some embodiments, R includes one or more functional groups selected from a halide, a ketone and a nitrile.

In certain embodiments, the tetrazolone is prepared from compound 12. In some instances of compound 12, X is selected from the group consisting of halogen (e.g., fluoro, chloro, bromo or iodo), azide and a leaving group of an active ester. In certain embodiments of compound 12, X is azide (i.e., $N_3$). In certain embodiments of compound 12, X is a leaving group of an active ester, such as an alkoxy, aryloxy, heteroaryloxy or a N-hydroxysuccinimidyl group (e.g., NHS). In certain embodiments of compound 12, X is chloro.

In some embodiments of Scheme 1, tetrazolone 17 is produced from to tetrazolone 16 via reaction with an alkylating agent. Any convenient alkylating agents and methods of using the same may be adapted to derivatize the subject tetraolone compounds. Alkylating agents of interest include, but are not limited to, alkyl halides, alkyl sulfonates, Michael acceptor reagents, In certain embodiments, the alkylating agent is methyl iodide. In certain cases, the alkylating agent may be used in conjunction with a basic reagent, such as potassium carbonate, in any convenient solvent.

In some embodiments, the compounds can be synthesized as shown below:

Scheme 2

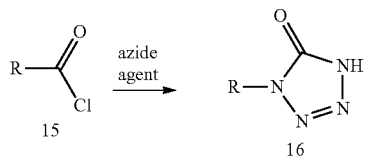

where compound 15 is an acid chloride that is converted to a tetrazolone compound 16 using an azide agent as described herein. The acid chloride compound may be prepared from any convenient starting materials according to any convenient method. In some cases, the acid chloride 15 is prepared (directly or indirectly) from a carboxylic acid containing compound of interest, e.g., as shown in scheme 1.

In some embodiments of schemes 1 and 2, R may be any convenient aryl, heteroaryl or heterocycle group, where R may be further substituted with one or more substituents. In some embodiments, compound 15 is an aryl or heteroaryl acid chloride. In some instances, R is a phenyl or substituted phenyl. In certain embodiments, R is a substituted biphenyl or a biphenyl. In certain embodiments, R is a pyridyl or a substituted pyridyl. In certain embodiments, R is an anthracene, a substituted anthracene, a naphthalene or a substituted naphthalene. In certain instances, R is a 5-membered heterocyclyl, such as a thienyl, a furanyl, an oxazole or an isooxazole. R may include a variety of additional substitutents. Any convenient electron rich or electron poor R aromatic groups may be utilized. In some embodiments, R further includes one or more substituents selected from the group consisting of alkyl, substituted alkyl, nitro, halogen, acyl, cyano, sulfonyl, alkylthio, alkoxy, substituted alkoxy, acyloxy, aralkyl, substituted aralkyl, heterocyclylalkyl, substituted heterocyclylalkyl, heteroarylalkyl, substituted heteroarylalkyl, aminosulfonyl, alkenyl, substituted alkenyl, heteroaryl, substituted heteroaryl, aryl and substituted aryl. In certain embodiments, R further includes one or more substituents selected from the group consisting of tert-butyl, trifluoromethyl, nitro, fluoro, bromo, chloro, iodo, acetyl, cyano, pentafluorosulfanyl (e.g., —$SF_5$), methylthio, acetoxy, diethylaminosulfonyl and 2-chlorophenyl.

In certain embodiments of schemes 1 and 2, R is described by the formula:

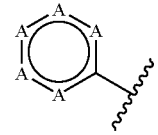

where each A is independently N or CR where R is H or a substituent. In certain instances, each R is independently selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocylooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl and trihalomethyl. In some embodiments, R is selected from the group consisting of alkyl, substituted alkyl, nitro, halogen, acyl, cyano, sulfonyl, alkylthio, alkoxy, substituted alkoxy, acyloxy, aralkyl, substituted aralkyl, heterocyclylalkyl, substituted heterocyclylalkyl, heteroarylalkyl, substituted heteroarylalkyl, aminosulfonyl, alkenyl, substituted alkenyl, heteroaryl, substituted heteroaryl, aryl and substituted aryl. In certain embodiments, R is selected from the group consisting of tert-butyl, trifluoromethyl, nitro, fluoro, bromo, chloro, iodo, acetyl, cyano, pentafluorosulfanyl (e.g., —$SF_5$), methylthio, acetoxy, diethylaminosulfonyl and 2-chlorophenyl.

In certain embodiments of schemes 1 and 2, R is described by one of the following formulae:

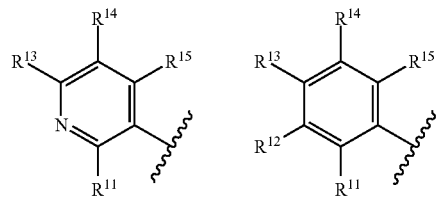

where $R^{11}$-$R^{15}$ are independently selected from the group consisting of hydrogen, acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocylooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl and trihalomethyl. In some embodiments, $R^{11}$-$R^{15}$ are independently selected from the group consisting of alkyl, substituted alkyl, nitro, halogen, acyl, cyano, sulfonyl, alkylthio, alkoxy, substituted alkoxy, acyloxy, aralkyl, substituted aralkyl, heterocyclylalkyl, substituted heterocyclylalkyl, heteroarylalkyl, substituted heteroarylalkyl, aminosulfonyl, alkenyl, substituted alkenyl, heteroaryl, substituted heteroaryl, aryl and substituted aryl. In certain embodiments, $R^{11}$-$R^{15}$ are independently selected from the group consisting of tert-butyl, trifluoromethyl, nitro, fluoro, bromo, chloro, iodo, acetyl, cyano, pentafluorosulfanyl (e.g., —$SF_5$), methylthio, acetoxy, diethylaminosulfonyl and 2-chlorophenyl.

In certain embodiments of schemes 1 and 2, R is described by one of the following formulae:

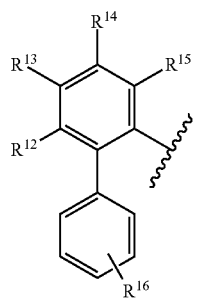 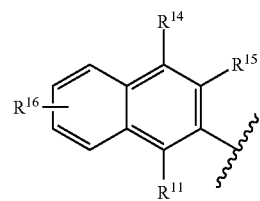

where $R^{11}$-$R^{16}$ are as described above for $R^{11}$-$R^{15}$.

In some embodiments of schemes 1 and 2, R may be any convenient alkyl, substituted alkyl, alkenyl or substituted alkenyl. In certain embodiments, R is an alkyl (e.g., methyl, ethyl, propyl, butyl). In certain embodiments, R is a substituted alkyl (e.g., isopropyl, tert-butyl). In certain embodiments, R is alkenyl. In certain embodiments, R is a substituted alkenyl (e.g., a substituted ethenyl group). In some embodiments, R further includes one or more substituents selected from the group consisting of alkyl, substituted alkyl, nitro, halogen, acyl, cyano, sulfonyl, alkylthio, alkoxy, substituted alkoxy, acyloxy, aralkyl, substituted aralkyl, heterocyclylalkyl, substituted heterocyclylalkyl, heteroarylalkyl, substituted heteroarylalkyl, aminosulfonyl, alkenyl, substituted alkenyl, heteroaryl, substituted heteroaryl, aryl and substituted aryl. In certain embodiments, R further includes one or more substituents selected from the group consisting of tert-butyl, trifluoromethyl, nitro, fluoro, bromo, chloro, iodo, acetyl, cyano, pentafluorosulfanyl (e.g., —$SF_5$), methylthio, acetoxy, diethylaminosulfonyl and 2-chlorophenyl.

Exemplary starting materials and tetrazolone compounds which may be prepared according to the methods described herein are show in Table A.

TABLE A

Tetrazolone formation from acid chloride

| Entry | Starting Material | Product |
|---|---|---|
| 1 | 5a | 6a |
| 2 | 5b | 6b |
| 3 | 5c | 6c |

TABLE A-continued
Tetrazolone formation from acid chloride
| Entry | Starting Material | Product |
|---|---|---|
| 4 | 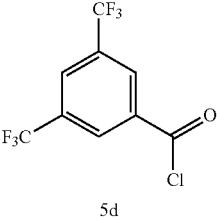 [SMILES: O=C(Cl)c1cc(C(F)(F)F)cc(C(F)(F)F)c1] 5d | 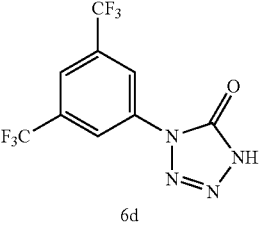 [SMILES: O=c1[nH]nnn1-c1cc(C(F)(F)F)cc(C(F)(F)F)c1] 6d |
| 5 | 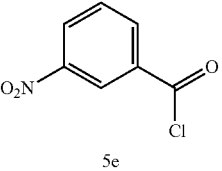 [SMILES: O=C(Cl)c1cccc([N+](=O)[O-])c1] 5e | 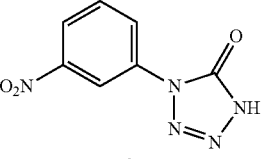 6e |
| 6 | 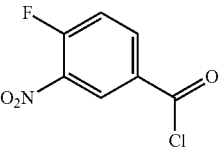 5f | 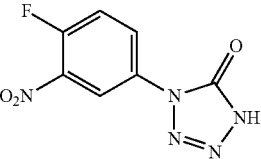 6f |
| 7 | 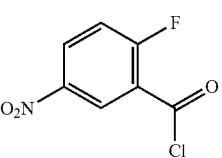 5g | 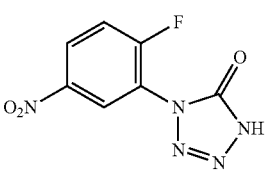 6g |
| 8 | 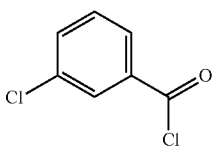 5h | 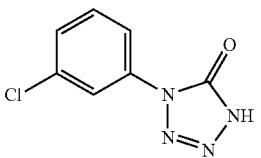 6h |
| 9 | 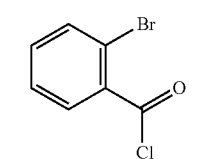 5i | 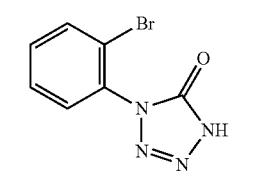 6i |
| 10 | 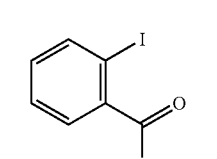 5j | 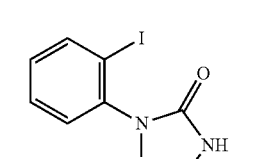 6j |

TABLE A-continued
Tetrazolone formation from acid chloride
| Entry | Starting Material | Product |
|---|---|---|
| 11 | 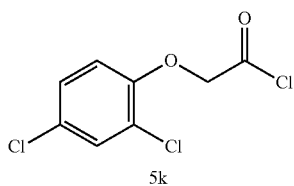 [SMILES: O=C(Cl)COc1ccc(Cl)cc1Cl]<br>5k | 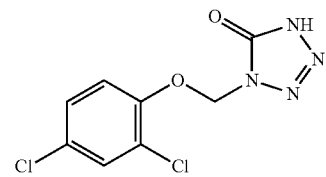<br>6k |
| 12 | 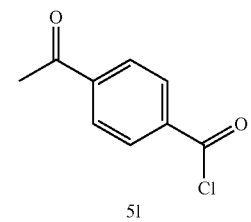<br>5l | 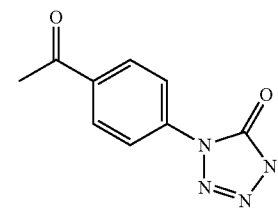<br>6l |
| 13 | 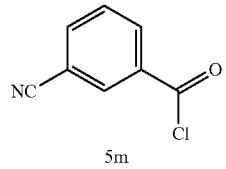<br>5m | 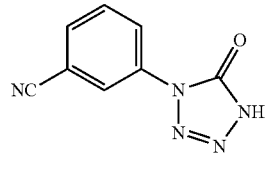<br>6m |
| 14 | 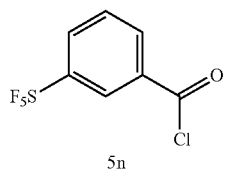<br>5n | 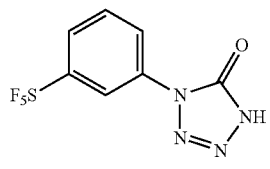<br>6n |
| 15 | 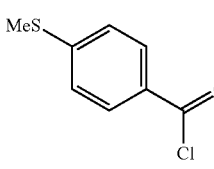<br>5o | 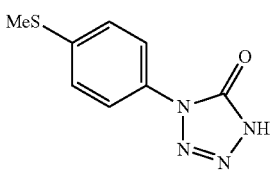<br>6o |
| 16 | 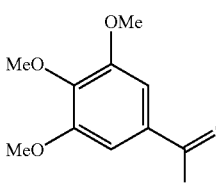<br>5p | 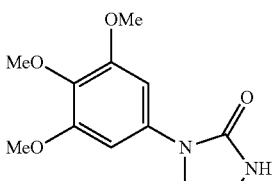<br>6p |

TABLE A-continued
Tetrazolone formation from acid chloride
| Entry | Starting Material | Product |
|---|---|---|
| 17 | 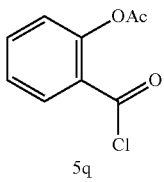 [SMILES: CC(=O)Oc1ccccc1C(=O)Cl] 5q | 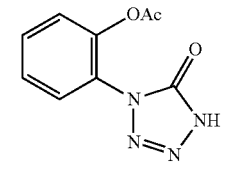 6q |
| 18 | 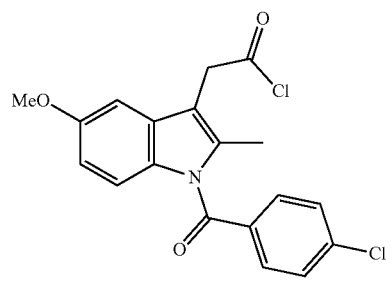 5r | 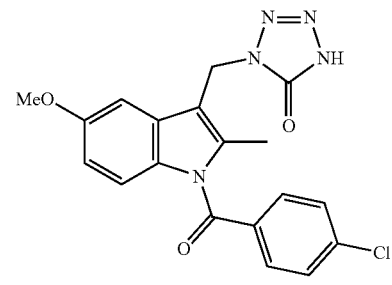 6r |
| 19 | 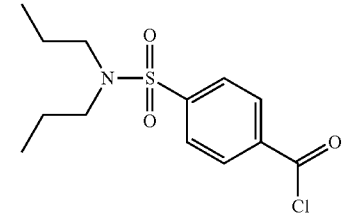 5s | 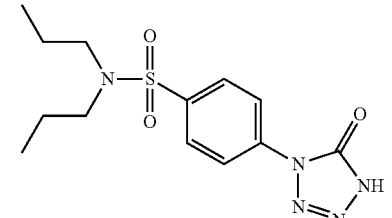 6s |
| 20 | 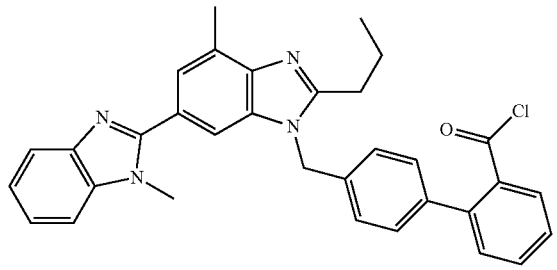 5t | 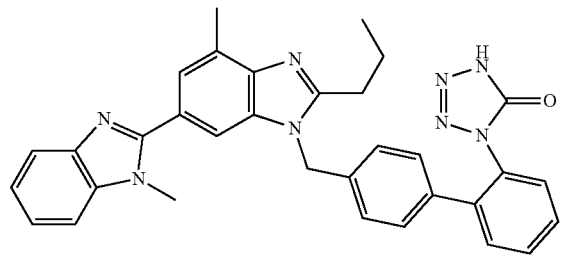 6t |

TABLE A-continued

Tetrazolone formation from acid chloride

| Entry | Starting Material | Product |
|---|---|---|
| 21 | 5u | 6u |
| 22 | 5v | 6v |
| 23 | 5w | 6w |
| 24 | 5x | 6x |
| 25 | 5y | 6y |
| 26 | 5z | 6z |

Azide Agents

For the synthesis of tetrazolone compounds, e.g., via scheme 1 or 2, any convenient azido agents may be utilized. As used herein, the term azide agent is used to refer to both stable commercially available reagents that are utilized in the subject methods, and transient azido reagents that may be formed in situ and are involved in the preparation of the subject tetrazolone compounds, e.g., in situ reagent formed by the combination of two or more starting agents. Azide agents of interest include, but are not limited to, an inorganic azide and a lewis acid, such as sodium azide/aluminium chloride; an organic azido reagent, such as an azido silane; and hydrazoic acid ($HN_3$). In some instances, the azide agent is provided using one or more agents selected from the group consisting of sodium azide, trimethylsilyl azide, imidazole-1-sulfonyl azide, trifluoromethanesulfonyl azide, and hydrazoic acid. In certain embodiments, the azide agent may be provided using an additional agent such as a Bronsted or Lewis acid, e.g., aluminium chloride, $TiCl_4$, $SiCl_4$, phosphorus pentachloride, $BF_3$, $OEt_2$, etc. In some embodiments, the azide agent is an azido silane (i.e., a silyl azide). In certain embodiments, the azide agent is trimethylsilyl azide ($TMSN_3$). In some cases, the azide agent is provided or pre-formed using a convenient method and then added to the reaction mixture of the subject methods. In other cases, the azide agent is formed in situ by adding two or more reagents to a reaction mixture that are capable of forming the azide agent of interest.

The subject methods of preparing a tetrazolone using an azide agent, e.g., as described in scheme 2, may be performed under any convenient reaction conditions that provide for production of the target tetrazolones. It is understood that a variety of reaction conditions such as solvent, temperature, pressure, microwave, flow chemistry, concentration, equivalents or stoichiometry of reagents and time may be adjusted as needed according to any convenient methods known in the art.

The subject methods of preparing a tetrazolone using an azide agent, e.g., as described in scheme 2, may be performed using any convenient solvents. In certain embodiments, the azide agent itself is utilized as a solvent. In certain instances, the azide agent is dissolved in an organic solvent. In certain embodiments, the reaction mixture, e.g., of scheme 2, includes 3.0 equivalents or more of the azide agent relative to the starting material, e.g., compound 5 of scheme 2, such as 3.5 equivalent or more, 4.0 equivalents or more, 4.5 equivalents or more, 5.0 equivalents or more, 5.5 equivalents or more, 6.0 equivalents or more, 6.5 equivalents or more, 7.0 equivalents or more, 8.0 equivalents or more, 9.0 equivalents or more, 10 equivalents or more, 20 equivalents or more, or even more.

The subject methods of preparing a tetrazolone using an azide agent, e.g., as described in scheme 2, may be performed at any convenient temperature and for any convenient length of time. In certain embodiments, the reaction mixture, e.g., of scheme 2, is heated at 50° C. or more, such as 60° C. or more, 70° C. or more, 80° C. or more, 90° C. or more, 100° C. or more, 110° C. or more, or even more, for a period of time sufficient to convert starting material (e.g., compound 15) to tetrazolone (16). Any convenient methods of monitoring the reaction may be utilized to assess the degree of completion, such as thin layer chromatography, HPLC, NMR, and the like.

In certain embodiments, tetrazolone compounds as described herein are prepared by adapting procedures known to those skilled in the art. Any convenient methods and materials may be adapted for use in the preparation of the subject compounds. Methods and materials of interest include, but are not limited to those described by, Singh et al., U.S. 2011/0130415, the disclosure of which is herein incorporated by reference in its entirety.

In some embodiments, the tetrazolone of the subject compound is prepared from an isocyanate precursor by reaction with an azide agent. Any convenient azide agents may be utilized. Azide agents of interest include but are not limited to, an inorganic azide and a lewis acid, such as sodium azide/aluminium chloride; an organic azido reagent, such as silyl azide, e.g. azidotrimethylsilane. The isocyanate precursors may be prepared using any convenient methods. Methods and materials of interest that may be adapted for use in the preparation of isocyanate precursors include, but are not limited to, those methods and materials described by Singh et al., U.S. 2011/0130415, the disclosure of which is herein incorporated by reference in its entirety. Any convenient organic solvents may be utilized in these methods of preparation. The methods may be performed at a variety of temperatures. In some cases, the methods are performed at room temperature. In some cases, the methods are performed with heating. In certain cases, the methods are performed at a temperature within 20° C. of the boiling point of the solvent, such as within 10° C. of the boiling point.

In certain embodiments, stereoisomers of compounds can be isolated by procedures known to those skilled in the art. The individual stereoisomers may be obtained, for instance, by a resolution technique or by chromatography techniques (e.g., silica gel chromatography, chiral chromatography, etc.).

Although the synthetic schemes discussed above may not illustrate the use of protecting groups, skilled artisans will recognize that in some instances certain substituents may include functional groups requiring protection. The exact identity of the protecting group used will depend upon, among other things, the identity of the functional group being protected and the reaction conditions used in the particular synthetic scheme, and will be apparent to those of skill in the art. Guidance for selecting protecting groups, their attachment and removal suitable for a particular application can be found, for example, in Greene & Wuts, supra.

Prodrugs as described herein can be prepared by routine modification of the above-described methods. Alternatively, such prodrugs can be prepared by reacting a suitably protected compound with a suitable progroup. Conditions for carrying out such reactions and for deprotecting the product to yield prodrugs as described herein are well-known.

Pharmaceutical Compositions

In certain embodiments, the disclosed compounds are useful for the treatment of a disease or disorder. Accordingly, pharmaceutical compositions comprising at least one disclosed compound are also described herein. In some instances, the pharmaceutical composition includes a compound of the present disclosure and a pharmaceutically acceptable carrier. In some cases, the pharmaceutical composition includes a therapeutically effective amount of compound of the present disclosure or a pharmaceutically acceptable salt or solvate or stereoisomer thereof, and a pharmaceutically acceptable carrier.

A disclosed compound can be administered alone, as the sole active pharmaceutical agent in the pharmaceutical composition, or in combination with one or more additional compounds of the present disclosure or in conjunction with other active agents. When administered as a combination, the therapeutic agents can be formulated as separate compositions that are administered simultaneously or at different times, or the therapeutic agents can be administered together as a single composition combining two or more therapeutic agents. Thus, the pharmaceutical compositions disclosed herein containing a compound of the present disclosure optionally include other therapeutic agents. Accordingly, certain embodiments are directed to such pharmaceutical compositions, where the composition further includes a therapeutically effective amount of an agent selected as is known to those of skill in the art.

Examples of such pharmaceutical compositions that include two or more active agents are pharmaceutical compositions having two or more compounds of the present disclosure. Other examples of pharmaceutical composition that include two or more active agents are pharmaceutical compositions having a compound of the present disclosure in conjunction with another active agent. For example, a pharmaceutical composition may include a compound of the present disclosure and an antihypertensive active agent, such as, but not limited to sacubitril or a prodrug thereof.

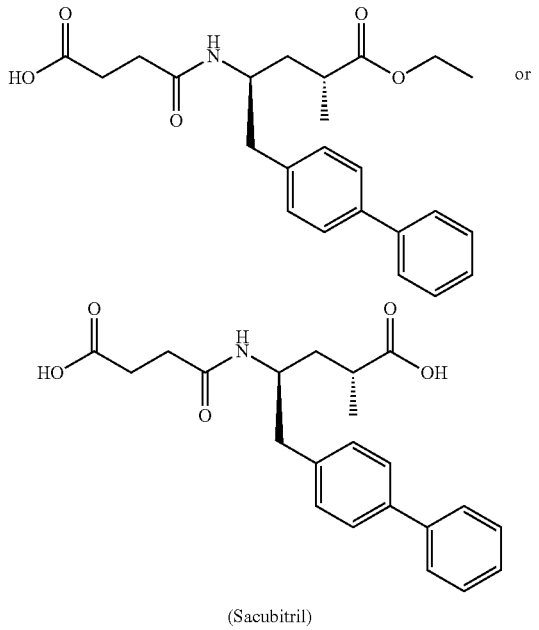

(Sacubitril)

In certain embodiments, a pharmaceutical composition may include an antihypertensive active agent, such as sacubitril, and a compound of the present disclosure, such as, but not limited to:

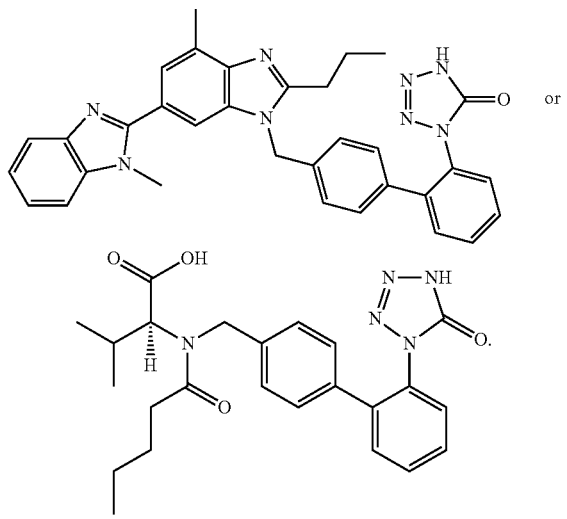

In certain embodiments, pharmaceutical compositions that include two active agents have a ratio (w/w) of a first active agent to a second active agent of 10:1, or 9:1, or 8:1, or 7:1, or 6:1, or 5:1, or 4:1, or 3:1, or 2:1, or 1:1, or 1:2, or 1:3, or 1:4, or 1:5, or 1:6, or 1:7, or 1:8, or 1:9, or 1:10. In some cases, pharmaceutical compositions that include two active agents have a ratio (w/w) of a first active agent to a second active agent of 1:1.

A pharmaceutical composition that includes a subject compound may be administered to a patient alone, or in combination with other supplementary active agents as described above. The pharmaceutical compositions may be manufactured using any of a variety of processes, including, but not limited to, conventional mixing, dissolving, granulating, dragee-making, levigating, emulsifying, encapsulating, entrapping, lyophilizing, and the like. The pharmaceutical composition can take any of a variety of forms including, but not limited to, a sterile solution, suspension, emulsion, lyophilisate, tablet, pill, pellet, capsule, powder, syrup, elixir or any other dosage form suitable for administration.

A subject compound may be administered to a subject using any convenient means capable of resulting in the desired reduction in disease condition or symptom. Thus, a subject compound can be incorporated into a variety of formulations for therapeutic administration. More particularly, a subject compound can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, aerosols, and the like.

Formulations for pharmaceutical compositions are described in, for example, Remington's Pharmaceutical Sciences, by E. W. Martin, Mack Publishing Co., Easton, Pa., 19th Edition, 1995, which describes examples of formulations (and components thereof) suitable for pharmaceutical delivery of disclosed compounds. Pharmaceutical compositions that include at least one of the subject compounds can be formulated for use in human or veterinary medicine. Particular formulations of a disclosed pharmaceutical composition may depend, for example, on the mode of administration and/or on the location of the subject to be treated. In some embodiments, formulations include a pharmaceutically acceptable carrier in addition to at least one active ingredient, such as a subject compound. In other embodiments, other medicinal or pharmaceutical agents, for example, with similar, related or complementary effects on the disease or condition being treated can also be included as active ingredients in a pharmaceutical composition.

Pharmaceutically acceptable carriers useful for the disclosed methods and compositions may depend on the particular mode of administration being employed. For example, parenteral formulations may include injectable fluids, such as, but not limited to, pharmaceutically and physiologically acceptable fluids such as water, physiological saline, balanced salt solutions, aqueous dextrose, glycerol or the like as a vehicle. For solid compositions (e.g., powder, pill, tablet, or capsule forms), non-toxic solid carriers can include, for example, pharmaceutical grades of mannitol, lactose, starch, or magnesium stearate. In addition to biologically neutral carriers, pharmaceutical compositions to be administered can optionally contain minor amounts of non-toxic auxiliary substances (e.g., excipients), such as wetting or emulsifying agents, preservatives, and pH buffering agents and the like; for example, sodium acetate or sorbitan monolaurate. Other examples of excipients include, nonionic solubilizers, such as cremophor, or proteins, such as human serum albumin or plasma preparations.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) water (e.g., pyrogen-free water); (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

The disclosed pharmaceutical compositions may be formulated as a pharmaceutically acceptable salt of a disclosed compound. Pharmaceutically acceptable salts are non-toxic salts of a free base form of a compound that possesses the desired pharmacological activity of the free base. These salts may be derived from inorganic or organic acids. Non-limiting examples of suitable inorganic acids are hydrochloric acid, nitric acid, hydrobromic acid, sulfuric acid, hydroiodic acid, and phosphoric acid. Non-limiting examples of suitable organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, methyl sulfonic acid, salicylic acid, formic acid, trichloroacetic acid, trifluoroacetic acid, gluconic acid, asparagic acid, aspartic acid, benzenesulfonic acid, para-toluenesulfonic acid, naphthalenesulfonic acid, and the like. In certain embodiments, the pharmaceutically acceptable salt includes formic acid. In certain embodiments, the pharmaceutically acceptable salt includes trifluoroacetic acid. Other suitable pharmaceutically acceptable salts are found in Remington's Pharmaceutical Sciences, 17th Edition, Mack Publishing Company, Easton, Pa., 1985. A pharmaceutically acceptable salt may also serve to adjust the osmotic pressure of the composition.

A subject compound can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. Such preparations can be used for oral administration.

A subject compound can be formulated into preparations for injection by dissolving, suspending or emulsifying the compound in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. The preparation may also be emulsified or the active ingredient encapsulated in liposome vehicles. Formulations suitable for injection can be administered by an intravitreal, intraocular, intramuscular, subcutaneous, sublingual, or other route of administration, e.g., injection into the gum tissue or other oral tissue. Such formulations are also suitable for topical administration.

In some embodiments, a subject compound can be delivered by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

A subject compound can be utilized in aerosol formulation to be administered via inhalation. A subject compound can be formulated into pressurized acceptable propellants such as dichlorodifluoromethane, propane, nitrogen and the like.

Furthermore, a subject compound can be made into suppositories by mixing with a variety of bases such as emulsifying bases or water-soluble bases. A subject compound can be administered rectally via a suppository. The suppository can include vehicles such as cocoa butter, carbowaxes and polyethylene glycols, which melt at body temperature, yet are substantially solid at room temperature.

The term "unit dosage form," as used herein, refers to physically discrete units suitable as unitary dosages for human and animal subjects, each unit containing a predetermined quantity of a subject compound calculated in an amount sufficient to produce the desired effect in association with a pharmaceutically acceptable diluent, carrier or vehicle. The specifications for a subject compound depend on the particular compound employed and the effect to be achieved, and the pharmacodynamics associated with each compound in the host.

The dosage form of a disclosed pharmaceutical composition may be determined by the mode of administration chosen. For example, in addition to injectable fluids, topical or oral dosage forms may be employed. Topical preparations may include eye drops, ointments, sprays and the like. Oral formulations may be liquid (e.g., syrups, solutions or suspensions), or solid (e.g., powders, pills, tablets, or capsules). Methods of preparing such dosage forms are known, or will be apparent, to those skilled in the art.

Certain embodiments of the pharmaceutical compositions that include a subject compound may be formulated in unit dosage form suitable for individual administration of precise dosages. The amount of active ingredient administered may depend on the subject being treated, the severity of the affliction, and the manner of administration, and is known to those skilled in the art. In certain instances, the formulation to be administered contains a quantity of the compounds disclosed herein in an amount effective to achieve the desired effect in the subject being treated.

Each therapeutic compound can independently be in any dosage form, such as those described herein, and can also be administered in various ways, as described herein. For example, the compounds may be formulated together, in a single dosage unit (that is, combined together in one form such as capsule, tablet, powder, or liquid, etc.) as a combination product. Alternatively, when not formulated together in a single dosage unit, an individual subject compound may be administered at the same time as another therapeutic compound or sequentially, in any order thereof.

Methods of Administration

The subject compounds find use in the treatment of a disease or disorder. Accordingly, the route of administration may be selected according to a variety of factors including, but not limited to, the condition to be treated, the formulation and/or device used, the patient to be treated, and the like. Routes of administration useful in the disclosed methods include but are not limited to oral and parenteral routes, such as intravenous (iv), intraperitoneal (ip), rectal, topical, ophthalmic, nasal, and transdermal. Formulations for these dosage forms are described herein.

An effective amount of a subject compound may depend, at least, on the particular method of use, the subject being treated, the severity of the affliction, and the manner of administration of the therapeutic composition. A "therapeutically effective amount" of a composition is a quantity of a specified compound sufficient to achieve a desired effect in a subject (e.g., patient) being treated. For example, this may be the amount of a subject compound necessary to treat (e.g., prevent, inhibit, reduce or relieve) a disease or disorder in a subject. In some instances, a therapeutically effective amount of a compound is an amount sufficient to prevent, inhibit, reduce or relieve a disease or disorder in a subject without causing a substantial cytotoxic effect on host cells.

Therapeutically effective doses of a subject compound or pharmaceutical composition can be determined by one of skill in the art, with a goal of achieving local (e.g., tissue) concentrations that are at least as high as the $IC_{50}$ of an applicable compound disclosed herein.

An example of a dosage range is from 0.1 to 200 mg/kg body weight orally in single or divided doses. In some embodiments, a dosage range is from 1.0 to 100 mg/kg body weight orally in single or divided doses, including from 1.0 to 50 mg/kg body weight, from 1.0 to 25 mg/kg body weight, from 1.0 to 10 mg/kg body weight (assuming an average body weight of approximately 70 kg; values may be adjusted accordingly for persons weighing more or less than average). For oral administration, the compositions are, for example, provided in the form of a tablet containing from about 10 to about 1000 mg of the active ingredient, such as 25 to 750 mg, or 50 to 500 mg, for example 75 mg, 100 mg, 200 mg, 250 mg, 400 mg, 500 mg, 600 mg, 750, mg, or 1000 mg of the active ingredient for the symptomatic adjustment of the dosage to the subject being treated. In certain embodiments of an oral dosage regimen, a tablet containing from 500 mg to 1000 mg active ingredient is administered once (e.g., a loading dose) followed by administration of ½ (i.e., half) dosage tablets (e.g., from 250 to 500 mg) each 6 to 24 hours for 3 days or more.

The specific dose level and frequency of dosage for any particular subject may be varied and may depend upon a variety of factors, including the activity of the subject compound, the metabolic stability and length of action of that compound, the age, body weight, general health, sex and diet of the subject, mode and time of administration, rate of excretion, drug combination, and severity of the condition of the host undergoing therapy.

Embodiments of the present disclosure also include combinations of one or more disclosed compounds with one or more other agents or therapies useful in the treatment of a disease or disorder. For example, one or more disclosed compounds may be administered in combination with therapeutically effective doses of other medicinal and pharmaceutical agents, or in combination other non-medicinal therapies, such as hormone or radiation therapy. The term "administration in combination with" refers to both concurrent and sequential administration of the active agents.

Therapeutic Applications

The subject compounds are useful for treating a disease or disorder in a subject in need of treatment. Accordingly, the present disclosure provides methods of treating a disease or disorder in a subject by administering an amount (e.g., a therapeutically effective amount) of a subject compound, including a salt or solvate or stereoisomer thereof.

Embodiments of the present disclosure are also directed to a compound of the present disclosure or a salt or solvate or stereoisomer thereof, for use in therapy or as a medicament. Additionally, embodiments are directed to the use of a compound of the present disclosure or a salt or solvate or stereoisomer thereof, for the manufacture of a medicament.

The embodiments are also directed to the use of a compound of the present disclosure or a salt or solvate or stereoisomer thereof for the manufacture of a medicament for the treatment of a disease or disorder.

Diseases or conditions of interest for treatment according to the present disclosure include, but are not limited to, hypertension, cancer (e.g., lymphoma, such as cutaneous T cell lymphoma (CTCL), relapsed or refractory peripheral T-cell lymphoma, etc.), multiple sclerosis (e.g., relapsing-remitting multiple sclerosis), anemia (e.g., anemia in Chronic Kidney Disease (CKD)), Irritable Bowel Syndrome (IBS; e.g., diarrhea predominant Irritable Bowel Syndrome (IBS-d)), cystic fibrosis, muscular dystrophy (e.g., Duchenne muscular dystrophy), bacterial infections, cardiovascular disease (e.g., myocardial infarction, stroke, unstable angina, coronary heart disease, high blood pressure, congestive heart failure, etc.), hyperlipidemia, diabetes, viral infections (e.g., HIV), liver disease (e.g., primary biliary cirrhosis, nonalcoholic steatohepatitis (NASH), portal hypertension, bile acid diarrhea (bile acid malabsorption), etc.), inflammation, gout, inflammatory bowel disease (IBD), Crohn's disease, endometriosis, dyslipidemia (e.g., hypercholesterolemia (heterozygous familial and nonfamilial) and mixed dyslipidemia (Fredrickson types IIa and IIb), heterozygous familial hypercholesterolemia, homozygous familial hypercholesterolemia, hypertriglyceridemia (Fredrickson Type IV), primary dysbetalipoproteinemia (Fredrickson Type III), combined hyperlipidemia, etc.), and the like.

Research Applications

Since subject compounds find use in the treatment of a disease or disorder, such compounds are also useful as research tools. Accordingly, the disclosure also provides for a method for using a compound of the present disclosure or a salt or solvate or stereoisomer thereof as a research tool for studying a biological system or sample, or for discovering new chemical compounds.

The present disclosure also provides a method for using subject compounds as a research tool for studying a biological system or sample. For example, the disclosure provides for a method of studying a biological system or sample, the method including: (a) contacting the biological sample with a compound of the present disclosure or a salt or solvate or stereoisomer thereof; and (b) determining the effects caused by the compound on the biological sample.

Any suitable biological sample can be employed in such studies which can be conducted either in vitro or in vivo. Representative biological samples suitable for such studies include, but are not limited to, cells, cellular extracts, plasma membranes, tissue samples, isolated organs, mammals (such as mice, rats, guinea pigs, rabbits, dogs, pigs, humans, and so forth), and the like, with mammals being of particular interest.

When used as a research tool, a biological sample is typically contacted with an effective amount of a subject compound. After the biological sample is exposed to the compound, the effects of the compound are determined using conventional procedures and equipment, such as the assays disclosed herein. Exposure encompasses contacting the biological sample with the compound or administering the compound to a subject. The determining step can involve measuring a response (a quantitative analysis) or can involve making an observation (a qualitative analysis). Measuring a response involves, for example, determining the effects of the compound on the biological sample using conventional procedures and equipment, such as radioligand binding assays and measuring ligand-mediated changes in functional assays. The assay results can be used to determine the activity level as well as the amount of compound necessary to achieve the desired result.

Additionally, the subject compounds can be used as research tools for evaluating other chemical compounds, and thus are also useful in screening assays to discover, for example, new compounds having a similar activity. In this manner, a subject compound can be used as a standard in an assay to allow comparison of the results obtained with a test compound and with the subject compounds to identify those test compounds that have about equal or superior activity, if any. For example, $IC_{50}$ data for a test compound or a group of test compounds is compared to the $IC_{50}$ data for a subject compound to identify those test compounds that have the desired properties, for example, test compounds having an $IC_{50}$ about equal or superior to a subject compound, if any.

This aspect includes, as separate embodiments, both the generation of comparison data (using the appropriate assays) and the analysis of test data to identify test compounds of interest. Thus, a test compound can be evaluated in a biological assay, by a method comprising the steps of: (a) conducting a biological assay with a test compound to provide a first assay value; (b) conducting the biological assay with a subject compound to provide a second assay value; wherein step (a) is conducted either before, after or concurrently with step (b); and (c) comparing the first assay value from step (a) with the second assay value from step (b).

EXAMPLES

The following examples are put forth so as to provide those of ordinary skill in the art with a complete disclosure and description of how to make and use the embodiments, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. As will be understood, by those of skill in the art of organic synthesis and medicinal chemistry the specific conditions set forth below are exemplary and can be varied or adapted to other reagents and products in routine fashion. Unless indicated otherwise, parts are parts by weight, molecular weight is weight average molecular weight, temperature is in degrees Celsius, and pressure is at or near atmospheric. Standard abbreviations may be used.

All reagents and solvents were purchased from commercial suppliers and used without further purification. Reactions were monitored by thin-layer chromatography or high-performance liquid chromatography. NMR was performed on a 300 MHz NMR spectrometer and all chemical shifts are reported relative to a tetramethylsilane internal standard, or by referencing on the deuterated solvent. Reverse-phase high-performance liquid chromatography was performed on standard equipment and was coupled to diode array and mass spectra detectors—the mass-spectra detector operating under the electrospray ionization (ESI) mode. The column-gradient system was as follows:
Column: Phenomenex Gemini 4.6×100 mm, C18, 5 μm, 110 Å
Column temperature 30° C.
Sample temperature 15° C.
Solvent A—0.05% Formic acid in Water
Solvent B—0.05% Formic acid in Acetonitrile
Flow rate—1.5 mL/min Gradient:

| Time | A % | B % |
|---|---|---|
| 0 | 95 | 5 |
| 10 | 0 | 100 (curve = 6) |
| 11.1 | 0 | 100 |
| 11.2 | 95 | 5 |
| 12.1 | 95 | 5 |

High resolution mass spectrometry were obtained on a LCT Premier XE mass spectrometer (time-of-flight) operating under the electrospray ionization mode. Mass analysis was performed in extended W-mode using leucine enkephalin as reference lock mass (556.2771 Da for positive ion & 554.2615 Da for negative ion).

20 mL Vials with pressure-release caps were obtained from Chemglass (catalogue #CG-4912-05). Reactions could also be undertaken in parallel using a heating block. The last position of the heating block was used to house a vial containing heat-resistant silicone oil. A thermocouple was then inserted in to the oil to control the temperature of the block.

Example 1

Experiments were performed to synthesize tetrazolones from acid chlorides using azidotrimethylsilane, which was used as both a co-reactant and solvent. The synthetic protocol minimized the formation of by-products, allowed for large-scale reactions, and provided products which contained a variety of functional groups, including the synthesis of tetrazolone analogs of active agents.

The general synthesis of tetrazolone derivatives is shown in Table 1.

TABLE 1

Reaction of 2-bromo-3-fluorobenzoyl chloride with azidotrimethylsilane.

| Entry | TMS-$N_3$ (equiv.) | Yield of 4 (%) |
|---|---|---|
| 1 | 6.0 | 82 |
| 2 | 4.5 | 76 |
| 3 | 3.0 | 37 |
| 4 | 4.0-6.0 (20-36 g scale) | 80-94 |

An example of the synthesis of tetrazolones included the reaction of 2-bromo-4-fluorobenzoyl chloride 3 with azidotrimethylsilane (TMS-$N_3$) at 100° C. (Table 1). Reacting 3 (1.5 g) with 6.0 equiv. of TMS-$N_3$ produced tetrazolone 4 in 82% isolated yield (entry 1). Reducing the stoichiometry of TMS-N₃ led to significant formation of a symmetrical urea by-product, and a lower isolated yield of desired tetrazolone 4. For example, the use of 4.5 equivalents of TMS-N₃ gave a 76% yield of tetrazolone 4 (entry 2), while the use of 3.0, equivalents of TMS-N₃ gave a 37% yield of tetrazolone 4 (entry 3), together with large quantities of a symmetrical urea, 1,3-bis-(2-bromo-4-fluorophenyl)urea. The desired tetrazolone 4 was obtained from all the above reaction mixtures by cooling, evaporation of the excess TMS-N₃ and use of a base/acidification extraction process to give product of high purity (>96%). The reaction was scaled-up without a significant decrease in yield. For instance, reactions with 20-36 g of acid chloride 3 and 4.0-6.0 equivalents of TMS-N₃ resulted in a 80-94% isolated yields of tetrazolone 4 (entry 4).

Reactions were performed using at least 6.0 equivalents of neat TMS-N₃ with a variety of different acid chloride substrates. In order to demonstrate that tetrazolone formation could be undertaken in a parallel manner, some reactions were performed in sealed vials with a pressure-release cap. Multiple reactions could be performed in a single heating block. After completion of the reaction, the mixture was worked-up by evaporating the excess TMS-N₃, extracting using a base/acid protocol, then purifying further with silica gel chromatography, if needed. The results of these experiments are shown in Table 2. As shown in Table 2, the reaction was useful for a variety of different functionalities in the acid chloride. For example, alkyl, trifluoromethyl, aryl, heteroaryl, alkenyl, nitro, fluoro, chloro, bromo, iodo, ketone, nitrile, pentafluorosulfanyl, ether, thioether, ester, amide and sulfonamide groups remained intact under the reaction conditions (entries 1-21). Additionally, reactions of acid chlorides directly attached to heteroaryl, alkenyl, or alkyl moieties were also successful (entries 22-26).

As shown in Table 2, reactions of acid chlorides containing trifluoromethyl- or fluoro-groups were successful (entries 4, 6 and 7). In addition, groups prone to nucleophilic aromatic displacement, such as activated halides, remained intact under the reaction conditions (entries 6, 7, 9-10). The efficiency of the reaction was unaffected by the presence of large ortho-substituents (entries 9-11), such as in a reaction to produce a tetrazolone analog of the herbicide 2,4-D (entry 11). The reaction of an acid chloride containing a ketone group did not produce concomitant Schmidt reaction (entry 12). Similarly, azidotrimethylsilane did not react with a substrate containing a nitrile group (entry 13). As shown in Table 2, the reaction of an acid chloride containing a pentafluorosulfanyl substituent also resulted in production of the desired tetrazolone derivative (entry 14).

In addition, reactions were performed to form a tetrazolone in a final-step, from fully-functionalized active agents, where a tetrazolone group served as a carboxylic acid bioisostere. For example, a tetrazolone derivative of Aspirin was produced and gave a 56% isolated yield of the tetrazolone product (entry 17). Tetrazolone analogs of the active agents Indomethacin, Probenecid, Telmisartan and Bexarotene were also prepared (entries 18-21). Isolated yields were 33-89%. Reactions with hetroaroyl chlorides were also performed. Both electron-deficient six-membered heterocycles (entry 22), and electron-rich five-membered heterocycles (entries 23 and 24) formed tetrazolone products under the reaction conditions. Compound 6v (entry 22) was a direct tetrazolone analog of the active agent Niacin. Reaction of acid chlorides attached to an olefin, or alkane (entries 25 and 26) were also performed. The reaction of hemi-fumarate 5y, gave a 62% yield of tetrazolone 6y (entry 25). The reaction with an acid chloride attached to an alkane, such as propionyl chloride 5z, afforded ethyl-tetrazolone 6z, in a 14% yield under the reaction conditions (entry 26; compare also with entries 11 and 18).

TABLE 2

Tetrazolone formation with acid chlorides and azidotrimethylsilane.

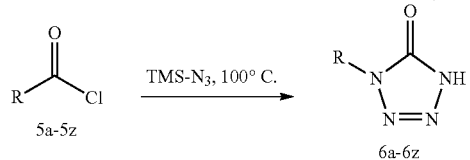

| Entry | Starting Material | Product | Yield (%) |
|---|---|---|---|
| 1 | 5a | 6a | 76 |
| 2 | 5b | 6b | 66 |

TABLE 2-continued

Tetrazolone formation with acid chlorides and azidotrimethylsilane.

| Entry | Starting Material | Product | Yield (%) |
|---|---|---|---|
| 3 | 5c (4-tert-butylbenzoyl chloride) | 6c | 61 |
| 4 | 5d (3,5-bis(trifluoromethyl)benzoyl chloride) | 6d | 56 |
| 5 | 5e (3-nitrobenzoyl chloride) | 6e | 90 |
| 6 | 5f (4-fluoro-3-nitrobenzoyl chloride) | 6f | 70 |
| 7 | 5g (2-fluoro-5-nitrobenzoyl chloride) | 6g | 86 |
| 8 | 5h (3-chlorobenzoyl chloride) | 6h | 60 |

TABLE 2-continued
Tetrazolone formation with acid chlorides and azidotrimethylsilane.
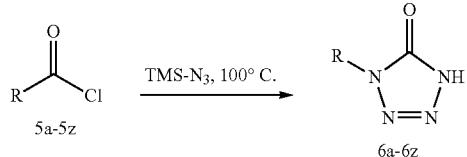
| Entry | Starting Material | Product | Yield (%) |
|---|---|---|---|
| 9 | 5i | 6i | 76 |
| 10 | 5j | 6j | 66 |
| 11 | 5k | 6k | 43[a] |
| 12 | 5l | 6l | 59[a] |
| 13 | 5m | 6m | 90 |
| 14 | 5n | 6n | 65[a] |

TABLE 2-continued
Tetrazolone formation with acid chlorides and azidotrimethylsilane.
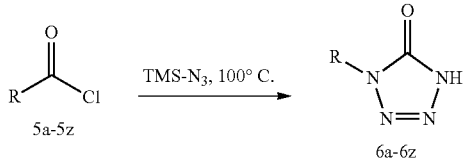
| Entry | Starting Material | Product | Yield (%) |
|---|---|---|---|
| 15 | 5o | 6o | 73[a] |
| 16 | 5p | 6p | 20 |
| 17 | 5q | 6q | 56 |
| 18 | 5r | 6r | 82[a] |
| 19 | 5s | 6s | 68[a] |

TABLE 2-continued
Tetrazolone formation with acid chlorides and azidotrimethylsilane.
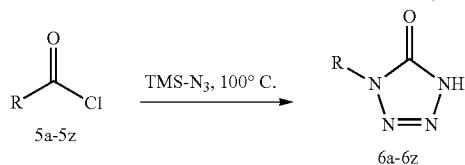
| Entry | Starting Material | Product | Yield (%) |
|---|---|---|---|
| 20 | 5t | 6t | 33[a] |
| 21 | 5u | 6u | 89[a] |
| 22 | 5v | 6v | 65 |
| 23 | 5w | 6w | 30 |
| 24 | 5x | 6x | 86 |

TABLE 2-continued

Tetrazolone formation with acid chlorides and azidotrimethylsilane.

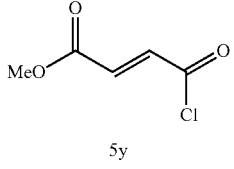

| Entry | Starting Material | Product | Yield (%) |
|---|---|---|---|
| 25 | 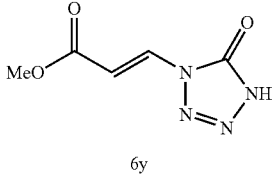 [SMILES: COC(=O)/C=C/n1nn[nH]c1=O] 5y | 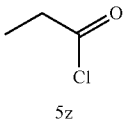 6y | 62[a] |
| 26 | 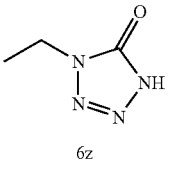 5z | 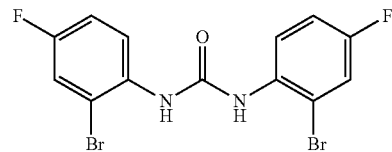 [SMILES: O=C(Nc1ccc(F)cc1Br)Nc1ccc(F)cc1Br] 6z | 14 |

[a] Acid chloride was prepared from acid prior to reaction with azidotrimethylsilane - reported yield is from acid to tetrazolone.

Preparation of 1-(2-bromo-4-fluorophenyl)-1,4-dihydro-5H-tetrazol-5-one 4

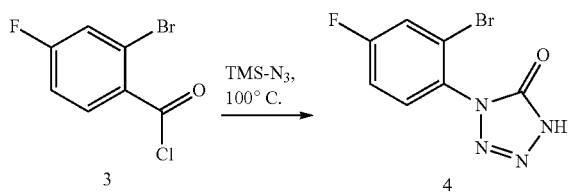 [SMILES: O=C(Cl)c1ccc(F)cc1Br ; O=c1[nH]nnn1-c1ccc(F)cc1Br]

Table 1, Entry 1:

Azidotrimethylsilane (5 mL, 38.0 mmol) was added in one portion to 2-bromo-4-fluorobenzoyl chloride 3 (1.5 g, 6.3 mmol). The mixture was placed under nitrogen and then heated to 100° C. with stirring [Note: 100° C. refers to temperature of heating block]. The mixture was left to stir at 100° C. overnight. After cooling, the mixture was concentrated under vacuum and the residue partitioned between EtOAc (50 mL) and H$_2$O (50 mL). The organic layer was then extracted with a saturated aqueous solution of NaHCO$_3$ (4×40 mL) [Note: extraction continued until TLC showed all tetrazolone product removed from the organic layer]. EtOAc (50 mL) was added to the combined NaHCO$_3$ layers, and the pH was adjusted to <3 using 6N HCl with efficient stirring. The aqueous and organic layers were partitioned, and the aqueous layer extracted with EtOAc (1×50 mL). The combined organic layers were dried (MgSO$_4$), filtered and the solvent removed under vacuum to afford the product (1.34 g, 82%) as a solid.

$^1$H NMR (DMSO-d$_6$, 300 MHz): δ 7.90 (dd, J=8.4, 2.7 Hz, 1H), 7.77 (dd, J=8.7, 5.7 Hz, 1H), 7.52-7.45 (m, 1H), −1.2 (br. s. 1H)

$^{19}$F NMR (DMSO-d$_6$, MHz): −107.6 (dd, J=13.8, 7.6 Hz)

$^{13}$C NMR (DMSO-d$_6$, 75 MHz): δ 164.2 (d, J=251 Hz), 150.7, 132.0 (d, J=9.3 Hz), 128.7 (d, J=3.8 Hz), 122.6 (d, J=11.0 Hz), 121.0 (d, J=26 Hz), 116.4 (d, J=23 Hz) m/z=257.28 [M−H]$^+$ for $^{79}$Br HRMS (EI): [1M−H]$^+$ calc'd for C$_7$H$_4$BrFN$_4$O m/z 256.9474, found 256.9527.

Table 1, Entry 2:

The above reaction was repeated using 4.5 equivalents of azidotrimethylsilane (3.75 mL) to give the product (1.24 g, 76%) as a solid.

Table 1, Entry 3:

The above reaction was repeated using 3.0 equivalents of azidotrimethylsilane (2.5 mL) to give the product (0.6 g, 37%) as a solid. Also isolated from the EtOAc layer after extraction with saturated NaHCO$_3$ was a symmetrical urea by-product, bis-(2-bromo-4-fluorphenyl)urea.

Data for bis-(2-bromo-4-fluorphenyl)urea:

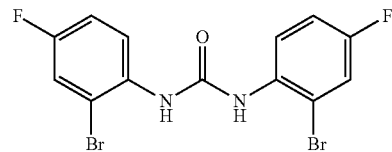 [SMILES: O=C(Nc1ccc(F)cc1Br)Nc1ccc(F)cc1Br]

$^1$H NMR (DMSO-d$_6$, 300 MHz): δ 8.82 (br. s, 2H), 7.88 (dd, J=9.0, 5.7 Hz, 2H), 7.57 (dd, J=8.7, 3.0 Hz, 2H), 7.22 (ddd, J=9.0, 8.1, 3.0, Hz, 2H)

$^{13}$C NMR (DMSO-d$_6$, 75 MHz): δ 159.2 (d, J=244 Hz), 152.7, 133.7 (d, J=3.3 Hz), 125.1 (d, J=8.3 Hz), 119.4 (d, J=25 Hz), 115.0 (d, J=22 Hz), 114.8 (d, J=10 Hz)

m/z=407.26 [M+H]$^+$ and 405.37 [M−H]$^+$

HRMS (EI): [M+H]$^+$ calc'd for C$_{13}$H$_8$Br$_2$F$_2$N$_2$O m/z 404.9050, found 404.9047; m/z 406.9030, found 406.9025; m/z 408.9011, found 408.9003.

HRMS (EI): [M−H]$^+$ calc'd for C$_{13}$H$_8$Br$_2$F$_2$N$_2$O m/z 402.8893, found 402.8912; m/z 404.8873, found 404.8815; m/z 406.8854, found 406.8802.

Table 1, Entry 4:

Note: For large-scale reactions, the mixtures were only placed under a nitrogen atmosphere after cessation of the gas evolution. The above reaction was repeated on a large-scale using azidotrimethylsilane (65 mL, 494 mmol) and 2-bromo-4-fluorobenzoyl chloride 3 (20.4 g, 85.9 mmol). The mixture was heated slowly and evolution of a gas (presumably, arising from a Curtius rearrangement) was noted from 50-60° C. (block temperature), which became a vigorous evolution when the block temperature was raised to ca. 65° C. The mixture was removed from the heat at a block temperature of ca. 70° C., and when gas evolution subsided, was re-subjected to heating stepwise from ca. 70° C. to 90° C. The mixture was stirred at 90° C. overnight. Usual workup, partitioning between EtOAc (200 mL) and H$_2$O (100 mL) and then extracting the organic layer with a saturated solution of NaHCO$_3$ (5×150 mL), followed by acidification and extraction with EtOAc, gave the product (19.9 g, 89%) as a solid.

A separate reaction using 20.0 g of 2-bromo-4-fluorobenzoyl chloride 3 and 47 mL of azidotrimethylsilane (4.0 equivalents) gave the product (17.4 g, 80%) as a solid.

A separate reaction using 36 g of 2-bromo-4-fluorobenzoyl chloride 3 and 120 mL of azidotrimethylsilane (6.0 equivalents) gave the product (37 g, 94%) as a solid. For this reaction, the mixture was heated slowly to ca. 55° C., whereupon the evolution of gas became regular. Evolution of gas stopped after ca. 15 min at 55° C. The mixture was then slowly heated to 90-95° C. (block temperature), placed under a nitrogen atmosphere and stirred overnight.

Preparation of 1-(2-bromo-4-fluorophenyl)-1,4-dihydro-5H-tetrazol-5-one 4 from 2-bromo-4-fluoro-1-isocyanoatobenzene

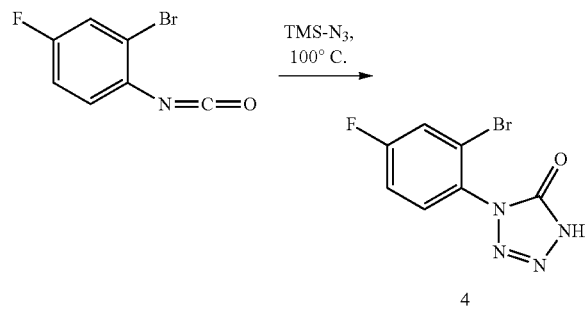

Azidotrimethylsilane (10 mL, 76 mmol) was added in one portion to 2-bromo-4-fluoro-1-isocyanatobenzene (3.0 g, 13.9 mmol). The mixture was placed under nitrogen and then heated to 90° C. with stirring [Note: 90° C. refers to temperature of heating block]. The mixture was left to stir at 90° C. overnight. After cooling, the mixture was concentrated under vacuum and the residue partitioned between EtOAc (50 mL) and a saturated aqueous solution of NaHCO$_3$ (100 mL). The organic layer was extracted with a further quantity of saturated aqueous NaHCO$_3$ (1×50 mL). EtOAc (100 mL) was added to the combined NaHCO$_3$ layers, and the pH was adjusted to <3 using 2N HCl with efficient stirring. The aqueous and organic layers were partitioned, and the organic layer was dried (Na$_2$SO$_4$), filtered and the solvent removed under vacuum to afford the product (3.44 g, 95%) as a solid.

A separate reaction was performed using 20.0 g of 2-bromo-4-fluoro-1-isocyanatobenzene (92.6 mmol) and 50 mL of azidotrimethylsilane (380 mmol; ca. 4.0 equivalents) to give the product (20.1 g, 84%) after workup.

Experiments with related starting materials indicated that the isocyanate to tetrazolone formation was complete within ca. 2 hours. It was likely that the reaction of acid chlorides to tetrazolones was similarly complete within a few hours, since it was observed that the Curtius rearrangement occurred quickly (evolution of gas complete within 15-30 min). In some instances, the reactions were typically run overnight for convenience.

Preparation of 1-phenyl-1,4-dihydro-5H-tetrazol-5-one 6a

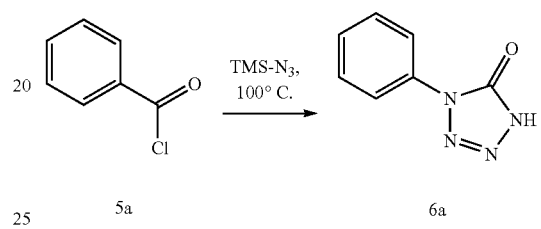

A stirred mixture of azidotrimethylsilane (2.4 mL, 18 mmol) and benzoyl chloride (422 mg, 3.0 mmol) was heated from room temperature to 100° C. (block temperature) in a sealed vial with pressure-release cap. The mixture was then stirred at 100° C. overnight (Note: pressure developed during heating). After cooling, the mixture was concentrated under vacuum and the residue partitioned between EtOAc (10 mL) and a saturated aqueous solution of NaHCO$_3$ (10 mL). The organic layer was extracted with a further quantity of saturated aqueous NaHCO$_3$ (1×10 mL) [note: organic layer assessed by TLC to ascertain if tetrazolone product was completely removed. If tetrazolone was still present in organic layer, then further extractions with saturated NaHCO$_3$ were used]. EtOAc (20 mL) was added to the combined NaHCO$_3$ layers, and the pH was adjusted to <3 using 6N HCl with efficient stirring. The aqueous and organic layers were partitioned and the aqueous layer was extracted with EtOAc (2×10 mL). The combined organic layers were dried (Na$_2$SO$_4$), filtered and the solvent removed under vacuum to afford the product (369 mg, 76%) as a solid. A sample was recrystallized from EtOAc.

$^1$H NMR (DMSO-d$_6$, 300 MHz): δ 7.85-7.81 (m, 2H), 7.57-7.50 (m, 2H), 7.41 (dt, J=7.5, 1.5 Hz, 1H), −1.3 (br. s, 1H)

$^{13}$C NMR (DMSO-d$_6$, 75 MHz): δ 150.3, 134.2, 129.5, 127.6, 119.5 m/z=163.18 [M+H]$^+$ and 161.24 [M−H]$^+$.

HRMS (EI): [M−H]$^+$ calc'd for C$_7$H$_6$N$_4$O m/z 161.0463, found 161.0532.

Preparation of 1-(naphthalen-2-yl)-1,4-dihydro-5H-tetrazol-5-one 6b

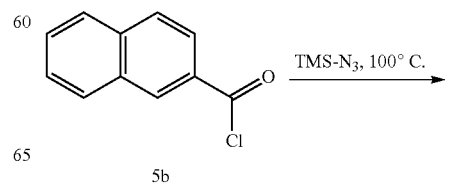

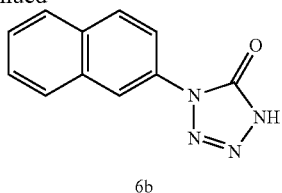

6b

A stirred mixture of azidotrimethylsilane (2.4 mL, 18 mmol) and 2-naphthoyl chloride (572 mg, 3.0 mmol) was heated from room temperature to 100° C. (block temperature) in a sealed vial with pressure-release cap. The mixture was then stirred at 100° C. overnight (Note: pressure developed during heating). After cooling, the mixture was concentrated under vacuum and the residue partitioned between EtOAc (10 mL) and a saturated aqueous solution of NaHCO$_3$ (10 mL). The organic layer was extracted with a further quantity of saturated aqueous NaHCO$_3$ (1×10 mL) [note: organic layer was assessed by TLC to ascertain if tetrazolone product was completely removed. If tetrazolone was still present in organic layer, then further extractions with saturated NaHCO$_3$ were used]. EtOAc (20 mL) was added to the combined NaHCO$_3$ layers, and the pH was adjusted to <3 using 6N HCl with efficient stirring. The aqueous and organic layers were partitioned and the aqueous layer was extracted with EtOAc (2×10 mL). The combined organic layers were dried (Na$_2$SO$_4$), filtered and the solvent removed under vacuum to afford the product (419 mg, 66%) as a solid. A sample was recrystallized from EtOAc.

$^1$H NMR (DMSO-d$_6$, 300 MHz): δ 8.42 (d, J=2.1 Hz, 1H), 8.09 (d, =8.7 Hz, 1H), 8.02-7.93 (m, 31H), 7.60-7.52 (m, 2H), −1.1 (br. s, 1H)

$^{13}$C NMR (DMSO-d$_6$, 75 MHz): δ 150.4, 132.7, 131.8, 131.6, 129.5, 128.1, 127.8, 127.2, 126.6, 118.1, 117.0 m/z=216.36 [M+H]$^+$ and 215.45 [M−H]$^+$

HRMS (EI): [M+H]$^+$ calc'd for C$_{11}$H$_8$N$_4$O m/z 213.0776, found 213.0764.

Preparation of 1-(4-(tert-butyl)phenyl)-1,4-dihydro-5H-tetrazol-5-one 6c

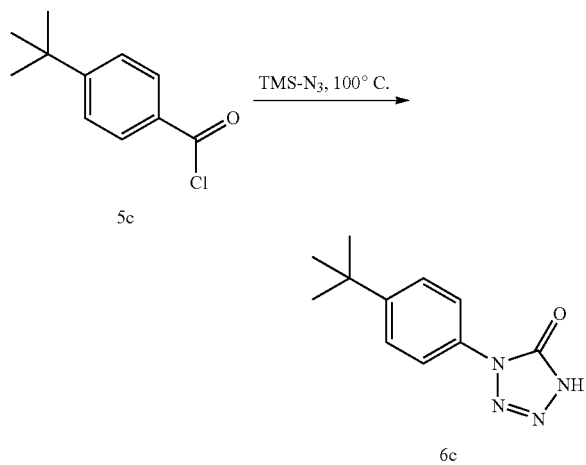

A stirred mixture of azidotrimethylsilane (2.4 mL, 18 mmol) and 4-(tert-butyl)benzoyl chloride (590 mg, 3.0 mmol) was heated from room temperature to 100° C. (block temperature) in a sealed vial with pressure-release cap. The mixture was then stirred at 100° C. overnight (Note: pressure developed during heating). After cooling, the mixture was concentrated under vacuum and the residue partitioned between EtOAc (20 mL) and a saturated aqueous solution of NaHCO$_3$ (20 mL). The organic layer was extracted with a further quantity of saturated aqueous NaHCO$_3$ (10×15 mL) [note: organic layer was assessed by TLC to ascertain if tetrazolone product was completely removed. If tetrazolone was still present in organic layer, then further extractions with saturated NaHCO$_3$ were used]. EtOAc (40 mL) was added to the combined NaHCO$_3$ layers, and the pH was adjusted to <3 using 6N HCl with efficient stirring. The aqueous and organic layers were partitioned and the aqueous layer was extracted with EtOAc (2×40 mL). The combined organic layers were dried (Na$_2$SO$_4$), filtered and the solvent removed under vacuum to afford the product (401 mg, 61%) as a solid.

$^1$H NMR (DMSO-d$_6$, 300 MHz): δ 7.74 (dt, J=8.7, 2.4 Hz, 2H), 7.57 (dt, J=8.7, 2.4 Hz, 2H), 1.29 (s, 9H), −1.3 (br. s, 1H)

$^{13}$C NMR (DMSO-d$_6$, 75 MHz): δ 150.3, 139.0, 131.7, 126.2, 119.5, 34.4, 31.0 m/z=219.31[M+H]$^+$ and 217.38 [M−H]$^+$

HRMS (EI): [M−H]$^+$ calc'd for C$_{11}$H$_{14}$N$_4$O m/z 217.1089, found 213.1139.

Preparation of 1-(3,5-bis(trifluoromethyl)phenyl)-1,4-dihydro-5H-tetrazol-5-one 6d

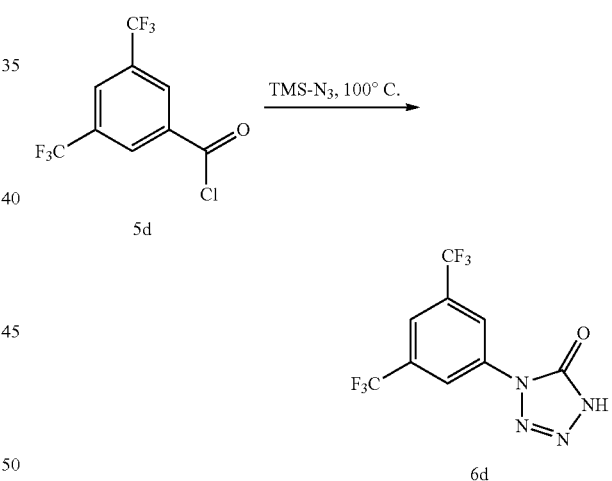

A stirred mixture of azidotrimethylsilane (2.4 mL, 18 mmol) and 3,5-bis(trifluoromethyl)benzoyl chloride (830 mg, 3.0 mmol) was heated from room temperature to 100° C. (block temperature) in a sealed vial with pressure-release cap. The mixture was then stirred at 100° C. overnight (Note: pressure developed during heating). After cooling, the mixture was concentrated under vacuum and the residue partitioned between EtOAc (10 mL) and a saturated aqueous solution of NaHCO$_3$ (10 mL). The organic layer from the initial partition above was concentrated under vacuum and purified by column chromatography on silica gel using hexane/EtOAc as eluent (ISCO Combiflash System) to give the product (503 mg, 56%) as a solid.

$^1$H NMR (DMSO-d$_6$, 300 MHz): δ 8.48 (s, 2H), 8.14 (s, 1H), −1.2 (br. s, 1H)

$^{19}$F NMR (DMSO-d$_6$, 282 MHz): δ −61.8 (s)
$^{13}$C NMR (DMSO-d$_6$, 75 MHz): δ 150.4, 136.0, 131.7 (q, J=33 Hz), 124.6 (q, J=271 Hz), 120.6 (m), 118.9 (m)
m/z=297.36 [M−H]$^+$
HRMS (EI): [M−H]$^+$ calc'd for C$_9$H$_4$F$_6$N$_4$O m/z 297.0211, found 297.0157.

Preparation of 1-(3-nitrophenyl)-1,4-dihydro-5H-tetrazol-5-one 6e

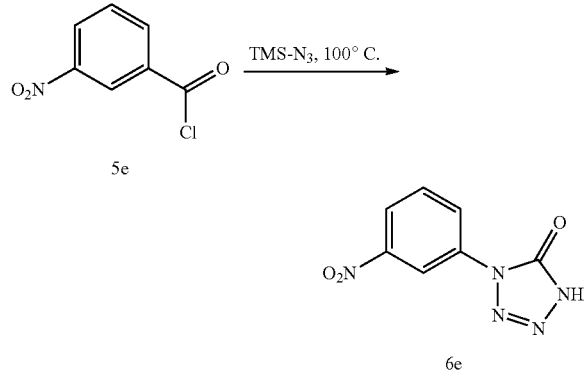

A stirred mixture of azidotrimethylsilane (2.4 mL, 18 mmol) and 3-nitrobenzoyl chloride (554 mg, 3.0 mmol) was heated from room temperature to 100° C. (block temperature) in a sealed vial with pressure-release cap. The mixture was then stirred at 100° C. for 2 hr (Note: pressure develops during heating). After cooling, the mixture was concentrated under vacuum and the residue partitioned between EtOAc (10 mL) and a saturated aqueous solution of NaHCO$_3$ (10 mL). The organic layer was extracted with a further quantity of saturated aqueous NaHCO$_3$ (1×10 mL) [note: organic layer was assessed by TLC to ascertain if tetrazolone product was completely removed. If tetrazolone was still present in organic layer, then further extractions with saturated NaHCO$_3$ were used]. EtOAc (20 mL) was added to the combined NaHCO$_3$ layers, and the pH was adjusted to <3 using 6N HCl with efficient stirring. The aqueous and organic layers were partitioned and the aqueous layer was extracted with EtOAc (2×10 mL). The combined organic layers were dried (Na$_2$SO$_4$), filtered and the solvent removed under vacuum to afford the product (560 mg, 90%) as a solid. A sample was recrystallized from EtOAc.
$^1$H NMR (DMSO-d$_6$, 300 MHz): δ 8.69 (t, J=4.2 Hz, 1H), 8.28-8.19 (m, 2H), 7.82 (t, J=8.3 Hz, 1H), −1.0 (br. s, 1H)
$^{13}$C NMR (DMSO-d$_6$, 75 MHz): δ 150.1, 148.1, 135.1, 131.2, 124.8, 121.8, 113.2
m/z=208.25 [M+H]$^+$ and 206.30 [M−H]$^+$
HRMS (EI): [M−H]$^+$ calc'd for C$_7$H$_5$N$_5$O$_3$ m/z 206.0314, found 206.0398.

Preparation of 1-(4-fluoro-5-nitrophenyl)-1,4-dihydro-5H-tetrazol-5-one 6f

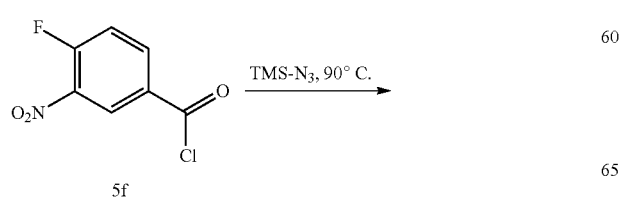

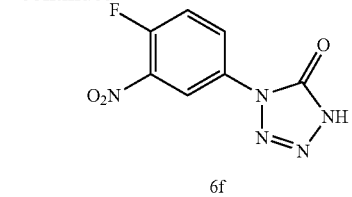

A stirred mixture of azidotrimethylsilane (7.9 mL, 60 mmol) and 4-fluoro-5-nitrobenzoyl chloride (2.04 g, 10 mmol) in a round bottom flask with reflux condenser was heated slowly from room temperature to 90° C. under an atmosphere of nitrogen (block temperature). The mixture was then stirred at 90° C. overnight. After cooling, the mixture was concentrated under vacuum and the residue partitioned between EtOAc (50 mL) and H$_2$O (50 mL). The organic layer was extracted with a saturated aqueous solution of NaHCO$_3$ (3×50 mL) [note: organic layer was assessed by TLC to ascertain if tetrazolone product was completely removed. If tetrazolone was still present in organic layer, then further extractions with saturated NaHCO$_3$ were used]. EtOAc (100 mL) was added to the combined NaHCO$_3$ layers, and the pH was adjusted to <3 using 6N HCl with efficient stirring. The aqueous and organic layers were partitioned and the organic layer was dried (MgSO$_4$), filtered and the solvent removed under vacuum to afford the product (1.96 g) as a solid. $^1$H NMR analysis indicated that the product was ca. 80-90% purity with approximately 10-20% of 4-fluoro-3-nitrobenzoic acid as a contaminant. Adjusting the yield for purity gives ca. 70% of desired product.

A sample of the above material was recrystallized from EtOAc to provide pure material.
$^1$H NMR (DMSO-d$_6$, 300 MHz): δ 8.63 (dd, J=9.6, 2.7 Hz, 1H), 8.25 (ddd, J=9.3, 3.9, 2.7 Hz, 1H), 7.80 (dd, J=11.1, 9.0 Hz, 1H), −1.0 (br. s, 1H)
$^{19}$F NMR (DMSO-d$_6$, 272 MHz): δ −119.7 (m)
$^{13}$C NMR (DMSO-d$_6$, 75 MHz): δ 154.9 (d, J=261 Hz), 150.2, 136.9 (d, J=8 Hz), 130.6 (d, J=3 Hz), 127.0 (d, J=9 Hz), 120.1 (d, J=23 Hz), 116.6 (d, J=3 Hz)
m/z=226.24 [M+H]$^+$ and 224.32 [M−H]$^+$
HRMS (EI): [M−H]$^+$ calc'd for C$_7$H$_4$FN$_5$O$_3$ m/z 224.0220, found 224.0227.

Preparation of 1-(2-fluoro-5-nitrophenyl)-1,4-dihydro-5H-tetrazol-5-one 6g

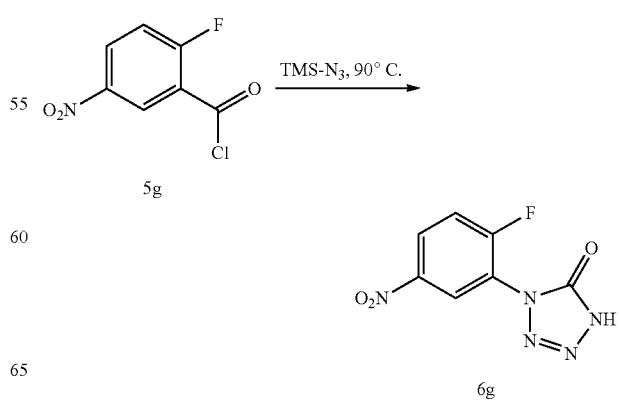

A stirred mixture of azidotrimethylsilane (19.7 mL, 150 mmol) and 2-fluoro-5-nitrobenzoyl chloride (5.1 g, 25 mmol) in a round bottom flask with reflux condenser was heated slowly from room temperature to 90° C. (block temperature) (note: evolution of nitrogen was observed from 70° C.). The mixture was then stirred at 90° C. for 5-6 hr (TLC indicated complete reaction). After cooling, the mixture was concentrated under vacuum and the residue partitioned between EtOAc (100 mL) and a saturated aqueous solution of NaHCO$_3$ (150 mL). The organic layer was extracted with a further quantity of saturated aqueous NaHCO$_3$ (1×50 mL) [note: organic layer was assessed by TLC to ascertain if tetrazolone product was completely removed. If tetrazolone was still present in organic layer, then further extractions with saturated NaHCO$_3$ were used]. EtOAc (200 mL) was added to the combined NaHCO$_3$ layers, and the pH was adjusted to <3 using 6N HCl with efficient stirring. The aqueous and organic layers were partitioned and the aqueous layer was extracted with EtOAc (1×100 mL). The combined organic layers were dried (MgSO$_4$), filtered and the solvent removed under vacuum to afford the product (4.8 g, 86%) as a solid. A sample was recrystallized from EtOAc.

$^1$H NMR (DMSO-d$_6$, 300 MHz): δ 8.66-8.63 (m, 1H), 8.49-8.43 (m, 1H), 7.82 (t, J=7.5 Hz, 1H), −1.0 (br. s, 1H)

$^{19}$F NMR (DMSO-d$_6$, 272 MHz): δ −110.4 (m)

$^{13}$C NMR (DMSO-d$_6$, 75 MHz): δ 160.9 (d, J=262 Hz), 150.5, 144.0 (d, J=3.1 Hz), 127.2 (d, J=9.9 Hz), 123.4 (d, J=2.2 Hz), 121.6 (d, J=13.7 Hz), 118.7 (d, J=22.1 Hz)

m/z=226.24 [M+H]$^+$ and 224.30 [M−H]$^+$

HRMS (EI): [M−H]$^+$ calc'd for C$_7$H$_4$FN$_5$O$_3$ m/z 224.0220, found 224.0231.

Preparation of 1-(3-chlorophenyl)-1,4-dihydro-5H-tetrazol-5-one 6h

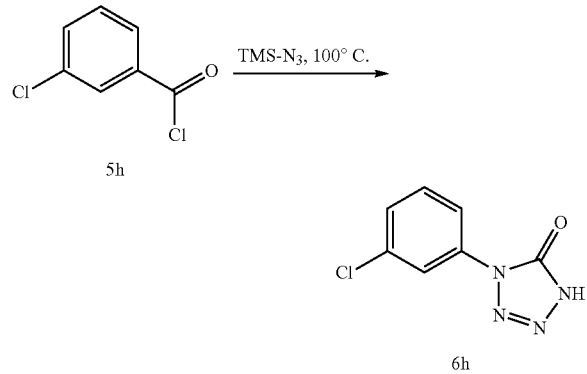

A stirred mixture of azidotrimethylsilane (2.4 mL, 18 mmol) and 3-chlorobenzoyl chloride (525 mg, 3.0 mmol) was heated from room temperature to 100° C. (block temperature) in a sealed vial with pressure-release cap. The mixture was then stirred at 100° C. overnight (Note: pressure developed during heating). After cooling, the mixture was concentrated under vacuum and the residue partitioned between EtOAc (10 mL) and a saturated aqueous solution of NaHCO$_3$ (10 mL). The organic layer was extracted with a further quantity of saturated aqueous NaHCO$_3$ (1×10 mL) [note: organic layer was assessed by TLC to ascertain if tetrazolone product was completely removed. If tetrazolone was still present in organic layer, then further extractions with saturated NaHCO$_3$ were used]. EtOAc (20 mL) was added to the combined NaHCO$_3$ layers, and the pH was adjusted to <3 using 6N HCl with efficient stirring. The aqueous and organic layers were partitioned and the aqueous layer was extracted with EtOAc (2×10 mL). The combined organic layers were dried (Na$_2$SO$_4$), filtered and the solvent removed under vacuum to afford the product (355 mg, 60%) as a solid. A sample was recrystallized from EtOAc.

$^1$H NMR (DMSO-d$_6$, 300 MHz): δ 7.92 (t, J=2.1 Hz, 1H), 7.82 (ddd, J=8.2, 2.1, 1.2 Hz, 1H), 7.59 (t, J=8.3 Hz, 1H), 7.46 (ddd, J=8.1, 2.1, 0.9 Hz, 1H), −1.1 (br. s, 1H)

$^{13}$C NMR (DMSO-d$_6$, 75 MHz): δ 150.1, 135.4, 133.7, 131.3, 127.3, 118.7, 117.6 m/z=197.30 [M+H]$^+$ and 195.38 [M−H]$^+$ for $^{35}$Cl

HRMS (EI): [M+H]$^+$ calc'd for C$_7$H$_5$ClN$_4$O m/z 195.0074, found 195.0099.

Preparation of 1-(2-bromophenyl)-1,4-dihydro-5H-tetrazol-5-one 6i

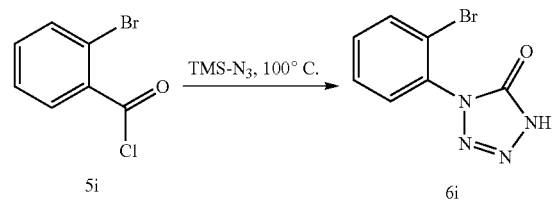 [SMILES: O=C(Cl)c1ccccc1Br ; O=c1[nH]nnn1-c1ccccc1Br]

A stirred mixture of azidotrimethylsilane (2.4 mL, 18 mmol) and 2-bromobenzoyl chloride (590 mg, 3.0 mmol) was heated from room temperature to 100° C. (block temperature) in a sealed vial with pressure-release cap. The mixture was then stirred at 100° C. for 24 hr (Note: pressure developed during heating). After cooling, the mixture was concentrated under vacuum and the residue partitioned between EtOAc (20 mL) and a saturated aqueous solution of NaHCO$_3$ (20 mL). The organic layer was extracted with a further quantity of saturated aqueous NaHCO$_3$ (1×20 mL) [note: organic layer was assessed by TLC to ascertain if tetrazolone product was completely removed. If tetrazolone was still present in organic layer, then further extractions with saturated NaHCO$_3$ were used]. EtOAc (30 mL) was added to the combined NaHCO$_3$ layers, and the pH was adjusted to <3 using 6N HCl with efficient stirring. The aqueous and organic layers were partitioned and the aqueous layer was extracted with EtOAc (2×30 mL). The combined organic layers were dried (Na$_2$SO$_4$), filtered and the solvent removed under vacuum to afford the product (546 mg, 76%) as a solid. A sample was recrystallized from EtOAc.

$^1$H NMR (DMSO-d$_6$, 300 MHz): δ 7.89 (dd, J=8.1, 1.5 Hz, 1H), 7.68 (dd, J=7.8, 2.1 Hz, 1H), 7.61-7.50 (m, 2H), −1.3 (br. s, 1H)

$^{13}$C NMR (DMSO-d$_6$, 75 MHz): δ 150.7, 133.5, 132.4, 131.9, 130.3, 129.0, 121.3 m/z=239.24 [M−H]$^+$

HRMS (EI): [M−H]$^+$ calc'd for C$_7$H$_5$BrN$_4$O m/z 238.9568, found 238.9577.

Preparation of 1-(2-iodophenyl)-1,4-dihydro-5H-tetrazol-5-one 6j

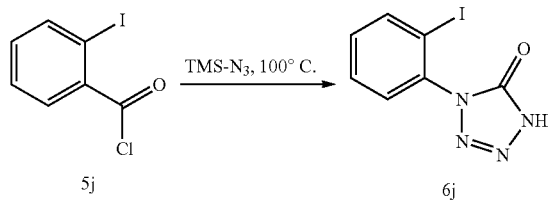 [SMILES: O=C(Cl)c1ccccc1I ; O=c1[nH]nnn1-c1ccccc1I]

A stirred mixture of azidotrimethylsilane (2.4 mL, 18 mmol) and 2-iodobenzoyl chloride (799 mg, 3.0 mmol) was heated from room temperature to 100° C. (block temperature) in a sealed vial with pressure-release cap. The mixture was then stirred at 100° C. overnight (Note: pressure developed during heating). After cooling, the mixture was concentrated under vacuum and the residue partitioned between EtOAc (10 mL) and a saturated aqueous solution of NaHCO$_3$ (10 mL). The organic layer was extracted with a further quantity of saturated aqueous NaHCO$_3$ (1×10 mL) [note: organic layer was assessed by TLC to ascertain if tetrazolone product was completely removed. If tetrazolone was still present in organic layer, then further extractions with saturated NaHCO$_3$ were used]. EtOAc (20 mL) was added to the combined NaHCO$_3$ layers, and the pH was adjusted to <3 using 6N HCl with efficient stirring. The aqueous and organic layers were partitioned and the aqueous layer was extracted with EtOAc (2×10 mL). The combined organic layers were dried (Na$_2$SO$_4$), filtered and the solvent removed under vacuum to afford the product (567 mg, 66%) as a solid. A sample was recrystallized from EtOAc.

$^1$H NMR (DMSO-d$_6$, 300 MHz): δ 8.07 (m, 1H), 7.61-7.57 (m, 2H), 7.38-7.29 (m, 1H), −1.3 (br. s, 1H)

$^{13}$C NMR (DMSO-d$_6$, 75 MHz): δ 150.5, 139.6, 135.5, 132.3, 129.6, 129.6, 98.2 m/z=289.31 [M+H]$^+$ and 287.42 [M−H]$^+$

HRMS (EI): [M+H]$^+$ calc'd for C$_7$H$_5$IN$_4$O m/z 289.9586, found 289.9588.

Preparation of 1-((2,4-dichlorophenoxy)methyl)-1,4-dihydro-5H-tetrazol-5-one 6k

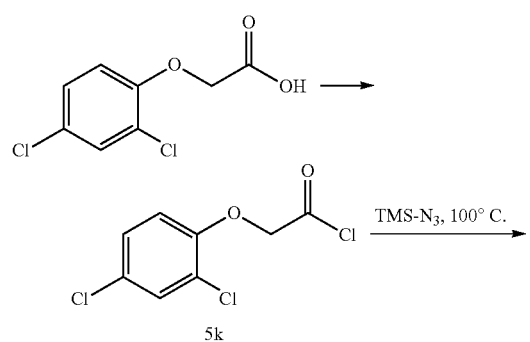

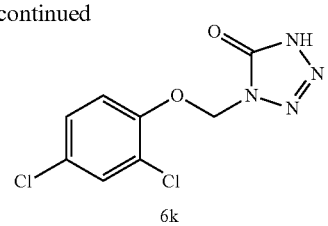

Oxalyl chloride (2.0 M in CH$_2$Cl$_2$; 3.0 mL, 6.0 mmol) was added dropwise over 2-3 min to a stirred suspension of 2,4-dichlorophenoxyacetic acid, also known as 2,4-D (663 mg, 3.0, mmol) and DMF (1-2 drops) in CH$_2$Cl$_2$ (6 mL) at 0° C. under nitrogen. After complete addition, the mixture was allowed to warm to room temperature and stirred over a weekend (note: a solution developed after warming to rt). The mixture was concentrated under vacuum to leave the acid chloride 5k, which was used directly in the tetrazolone-forming step below (yield assumed quantitative=718 mg).

A stirred mixture of azidotrimethylsilane (2.4 mL, 18 mmol) and 2,4-dichlorophenoxyacetyl chloride (718 mg, 3.0 mmol) was heated from room temperature to 100° C. (block temperature) in a round bottom flask with reflux condenser under an atmosphere of nitrogen. The mixture was then stirred at 100° C. for 3 hours. After cooling, the mixture was concentrated under vacuum and the residue partitioned between EtOAc (30 mL) and a saturated solution of NaHCO$_3$ (30 mL). The organic layer was extracted with a saturated solution of NaHCO$_3$ (1×30 mL) [note: organic layer was assessed by TLC to ascertain if tetrazolone product was completely removed. If tetrazolone was still present in organic layer, then further extractions with saturated NaHCO$_3$ were used]. EtOAc (30 mL) was added to the filtrate and the pH was adjusted to <3 using 6N HCl with efficient stirring. The aqueous and organic layers were partitioned and the aqueous layer was extracted with EtOAc (2×20 mL). The combined organic layers were dried (Na$_2$SO$_4$), filtered and the solvent removed under vacuum to afford the crude product (600 mg) of ca. 90% purity. The crude product was purified by column chromatography on silica gel (ISCO Combiflash) using CH$_2$Cl$_2$/MeOH (1:0 to 9:1) as eluent to give pure product (336 mg, 43%) as a solid. Less pure product (ca. 130 mg) was also obtained from the column, but was not purified further.

$^1$H NMR (DMSO-d$_6$, 300 MHz): δ 7.59 (d, J=2.4 Hz, 1H), 7.49 (d, J=8.7 Hz, 1H), 7.43 (dd, J=8.7, 2.4 Hz, 1H), 5.94 (s, 2H), −1.4 (br. s, 1H)

$^{13}$C NMR (DMSO-d$_6$, 75 MHz): δ 151.3, 150.6, 129.7, 128.3, 127.2, 124.2, 118.6, 71.2 m/z=261.30 [M+H]$^+$ and 259.37 [M−H]$^+$ for $^{35}$Cl

Preparation of 1-(4-acetylphenyl)-1,4-dihydro-5H-tetrazol-5-one 6l

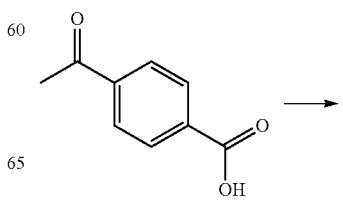

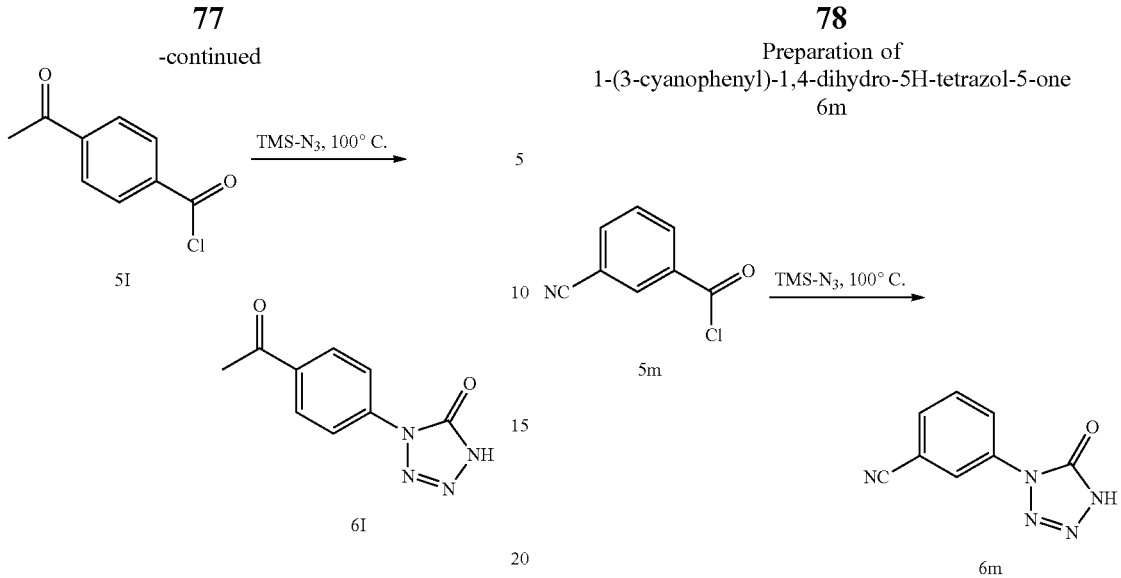

Oxalyl chloride (2.0 M in CH$_2$Cl$_2$; 3.0 mL, 6.0 mmol) was added dropwise over 2-3 min to a stirred suspension of 4-acetylbenzoic acid (493 mg, 3.0 mmol) and DMF (1-2 drops) in CH$_2$Cl$_2$ (6 mL) at 0° C. under nitrogen. After complete addition, the mixture was allowed to warm to room temperature and stirred overnight. The mixture was concentrated under vacuum to leave the acid chloride 5l, which was used directly in the tetrazolone-forming step below (yield assumed quantitative=548 mg).

A stirred mixture of azidotrimethylsilane (2.4 mL, 18 mmol) and 4-acetylbenzoyl chloride (548 mg, 3.0 mmol) was heated from room temperature to 100° C. (block temperature) in a sealed vial with pressure-release cap. The mixture was then stirred at 100° C. overnight (Note: pressure developed during heating). After cooling, the mixture was concentrated under vacuum and the residue partitioned between EtOAc (100 mL) and a 1:1 mixture of saturated NaHCO$_3$ (75 mL) and H$_2$O (75 mL). The organic layer was extracted with a 1:1 mixture of saturated NaHCO$_3$ (25 mL) and H$_2$O (25 mL) [note: organic layer was assessed by TLC to ascertain if tetrazolone product was completely removed. If tetrazolone was still present in organic layer, then further extractions with saturated NaHCO$_3$ were used]. The aqueous layer was filtered to remove minor insoluble items and then EtOAc (100 mL) was added to the filtrate. The pH was adjusted to <3 using 6N HCl with efficient stirring (if an azidohydrin was formed from the reaction, then treatment with acid may release HCN). The aqueous and organic layers were partitioned and the aqueous layer was extracted with EtOAc (2×75 mL). The combined organic layers were dried (Na$_2$SO$_4$), filtered and the solvent removed under vacuum to afford the crude product (445 mg) of ca. 90-95% purity. The crude product was purified by column chromatography on silica gel (ISCO Combiflash) using CH$_2$Cl$_2$/MeOH (1:0 to 9:1) as eluent to give the product (360 mg, 59%) as a solid.

$^1$H NMR (DMSO-d$_6$, 300 MHz): δ 8.11 (d, J=7.2 Hz, 2H), 8.02 (d, J=9.0 Hz, 2H), 2.58 (s, 3H),−1.0 (br. s, 1H)

$^{13}$C NMR (DMSO-d$_6$, 75 MHz): δ 196.8, 150.1, 137.8, 135.1, 129.7, 118.3, 26.7 m/z=203.30 [M−H]$^+$

HRMS (EI): [M+H]$^+$ calc'd for C$_9$H$_8$N$_4$O$_2$ m/z 205.0726, found 205.0721.

Preparation of 1-(3-cyanophenyl)-1,4-dihydro-5H-tetrazol-5-one 6m

A stirred mixture of azidotrimethylsilane (2.4 mL, 18 mmol) and 3-cyanobenzoyl chloride (497 mg, 3.0 mmol) was heated from room temperature to 100° C. (block temperature) in a sealed vial with pressure-release cap. The mixture was then stirred at 100° C. overnight (Note: pressure developed during heating). After cooling, the mixture was concentrated under vacuum and the residue partitioned between EtOAc (10 mL) and a saturated aqueous solution of NaHCO$_3$ (10 mL). The organic layer was extracted with a further quantity of saturated aqueous NaHCO$_3$ (1×10 mL) [note: organic layer was assessed by TLC to ascertain if tetrazolone product was completely removed. If tetrazolone was still present in organic layer, then further extractions with saturated NaHCO$_3$ were used]. EtOAc (20 mL) was added to the combined NaHCO$_3$ layers, and the pH was adjusted to <3 using 6N HCl with efficient stirring. The aqueous and organic layers were partitioned and the aqueous layer was extracted with EtOAc (2×10 mL). The combined organic layers were dried (Na$_2$SO$_4$), filtered and the solvent removed under vacuum to afford the product (505 mg, 90%) as a solid. A sample was recrystallized from EtOAc.

$^1$H NMR (DMSO-d$_6$, 300 MHz): δ 8.26 (m, 1H), 8.16 (ddd, J=8.7, 2.4, 1.2 Hz, 1H), 7.87 (dt, J=7.8, 2.7 Hz, 1H), 7.48 (dt, J=8.3, 0.6 Hz, 1H), −1.1 (br. s, 1H)

$^{13}$C NMR (DMSO-d$_6$, 75 MHz): δ 150.1, 134.9, 131.1, 131.0, 123.7, 122.1, 117.9, 112.4 m/z=188.30 [M+H]$^+$ and 186.42 [M−H]$^+$

HRMS (EI): [M−H]$^+$ calc'd for C$_8$H$_5$N$_5$O m/z 186.0486, found 186.0427.

Preparation of 1-(3-(pentafluorosulfanyl)phenyl)-1,4-dihydro-5H-tetrazol-5-one 6n

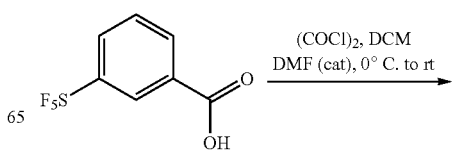

-continued

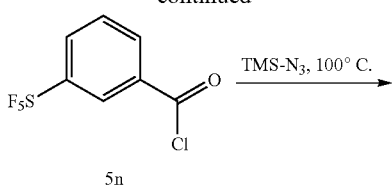

Preparation of 1-(4-(methylthio)phenyl)-1,4-dihydro-5H-tetrazol-5-one 6o

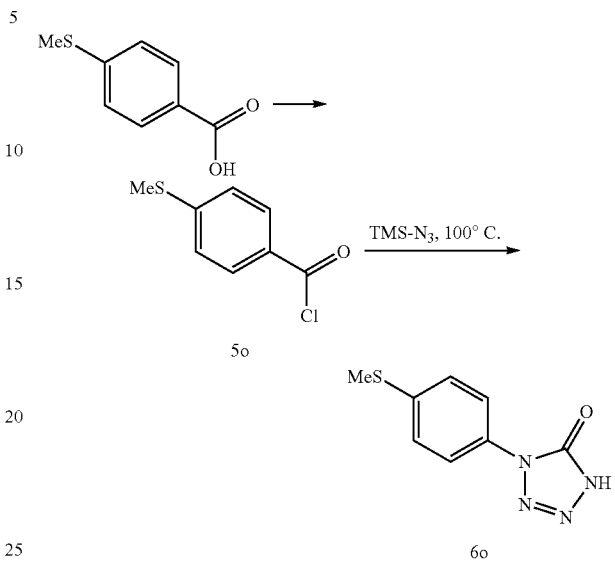

Oxalyl chloride (2.0 M in CH$_2$Cl$_2$; 0.75 mL, 1.5 mmol) was added dropwise over 2-3 min to a stirred suspension of 3-(pentafluorosulfanyl)benzoic acid (248 mg, 1.0 mmol) and DMF (2-3 drops) in CH$_2$Cl$_2$ (3 mL) at 0° C. under nitrogen. After complete addition, the mixture was stirred at 0° C. for 1 hr then allowed to warm to room temperature and stirred for 3 hr. The mixture was concentrated under vacuum to leave the acid chloride 5n, which was used directly in the tetrazolone-forming step below (yield assumed quantitative=267 mg).

Note: 18 equivalent of TMS-N$_3$ were used in order to ensure complete coverage of the material in a vial with pressure-release cap.

A stirred mixture of azidotrimethylsilane (2.4 mL, 18 mmol) and 3-(pentafluorosulfanyl)benzoyl chloride (267 mg, 1.0 mmol) was heated from room temperature to 100° C. (block temperature) in a sealed vial with pressure-release cap. The mixture was then stirred at 100° C. overnight (Note: pressure developed during heating). After cooling, the mixture was concentrated under vacuum and the residue partitioned between EtOAc (20 mL) and a saturated aqueous solution of NaHCO$_3$ (10 mL). The organic layer was extracted with a further quantity of saturated aqueous NaHCO$_3$ (8×10 mL) [note: organic layer was assessed by TLC to ascertain if tetrazolone product was completely removed. If tetrazolone was still present in organic layer, then further extractions with saturated NaHCO$_3$ were used]. EtOAc (30 mL) was added to the combined NaHCO$_3$ layers, and the pH was adjusted to <3 using 6N HCl with efficient stirring. The aqueous and organic layers were partitioned and the aqueous layer was extracted with EtOAc (2×30 mL). The combined organic layers were dried (Na$_2$SO$_4$), filtered and the solvent removed under vacuum to afford the product (187 mg, 65%) as a solid.

$^1$H NMR (DMSO-d$_6$, 300 MHz): δ 8.40 (t, J=2.1 Hz, 1H), 8.14 (d, J=8.1 Hz, 1H), 7.92-7.96 (m, 1H), 7.80 (t, J=8.6 Hz, 1H), −1.1 (br. s, 1H)

$^{19}$F NMR (DMSO-d$_6$, 272 MHz): δ −114.4 (quin., J=145 Hz), −136.2 (d, J=145 Hz)

$^{13}$C NMR (DMSO-d$_6$, 75 MHz): δ 153.0 (quin., J=17.3 Hz), 150.2, 134.7, 130.9, 124.5 (quin., J=4.7 Hz), 123.0, 116.1 (quin., J=5.0 Hz)

m/z=287.45 [M−H]$^+$

HRMS (EI): [M−H]$^+$ calc'd for C$_7$H$_5$F$_3$N$_4$OS m/z 287.0026, found 287.0059.

Oxalyl chloride (2.0 M in CH$_2$Cl$_2$; 3.0 mL, 6.0 mmol) was added dropwise over 2-3 min to a stirred suspension of 4-(methylthio)benzoic acid (505 mg, 3.0 mmol) and DMF (1-2 drops) in CH$_2$Cl$_2$ (6 mL) at 0° C. under nitrogen. After complete addition, the mixture was allowed to warm to room temperature and stirred overnight. The mixture was concentrated under vacuum to leave the acid chloride 5o, which was used directly in the tetrazolone-forming step below (yield assumed quantitative=560 mg).

A stirred mixture of azidotrimethylsilane (2.4 mL, 18 mmol) and 4-(methylthio)benzoyl chloride (560 mg, 3.0 mmol) was heated from room temperature to 100° C. (block temperature) in a sealed vial with pressure-release cap. The mixture was then stirred at 100° C. overnight (Note: pressure developed during heating). After cooling, the mixture was concentrated under vacuum and the residue partitioned between EtOAc (100 mL) and a 1:1 mixture of saturated NaHCO$_3$ (50 mL) and H$_2$O (50 mL). The organic layer was extracted with a further quantity of saturated aqueous NaHCO$_3$ (2×30 mL) [note: organic layer was assessed by TLC to ascertain if tetrazolone product was completely removed. If tetrazolone was still present in organic layer, then further extractions with saturated NaHCO$_3$ were used]. EtOAc (75 mL) was added to the combined NaHCO$_3$ layers, and the pH was carefully adjusted to <3 using 6N HCl with efficient stirring. The aqueous and organic layers were partitioned and the aqueous layer was extracted with EtOAc (2×50 mL). The combined organic layers were dried (Na$_2$SO$_4$), filtered and the solvent removed under vacuum to afford a crude residue containing product (ca. 93% purity). The residue was purified by column chromatography on silica gel (ISCO Combiflash) using CH$_2$Cl$_2$/MeOH (1:0 to 9:1) as eluent to give the product (473 mg, 73%) as a solid.

$^1$H NMR (DMSO-d$_6$, 300 MHz): δ 7.78-7.73 (m, 2H), 7.42-7.38 (m, 2H), 2.49 (s, 3H), −1.3 (br. s, 1H)

$^{13}$C NMR (DMSO-d$_6$, 75 MHz): δ 150.2, 137.9, 131.1, 126.6, 120.1, 14.7 m/z=209.27 [M+H]$^+$ and 207.41 [M−H]$^+$

HRMS (EI): [M+H]$^+$ calc'd for C$_8$H$_8$N$_4$OS m/z 209.0497, found 209.0482.

Preparation of 1-(3,4,5-trimethoxyphenyl)-1,4-dihydro-5H-tetrazol-5-one 6p

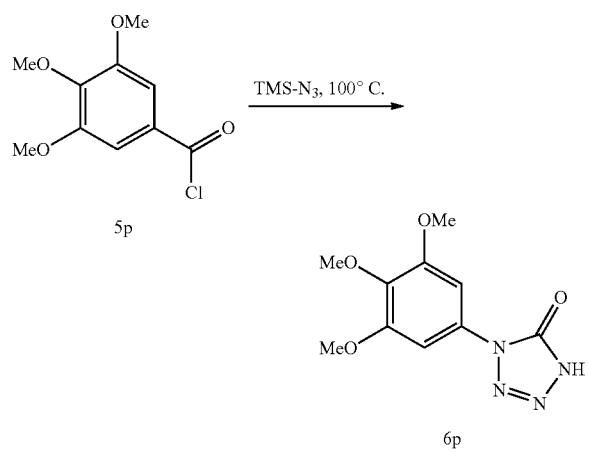

A stirred mixture of azidotrimethylsilane (2.4 mL, 18 mmol) and 3,4,5-trimethoxybenzoyl chloride (692 mg, 3.0 mmol) was heated from room temperature to 100° C. (block temperature) in a sealed vial with pressure-release cap. The mixture was then stirred at 100° C. overnight (Note: pressure developed during heating). After cooling, the mixture was concentrated under vacuum and the residue partitioned between EtOAc (10 mL) and a saturated aqueous solution of NaHCO$_3$ (10 mL). The organic layer was extracted with a further quantity of saturated aqueous NaHCO$_3$ (1×10 mL) [note: organic layer was assessed by TLC to ascertain if tetrazolone product was completely removed. If tetrazolone was still present in organic layer, then further extractions with saturated NaHCO$_3$ were used]. EtOAc (20 mL) was added to the combined NaHCO$_3$ layers, and the pH was carefully adjusted to <3 using 6N HCl with efficient stirring. The aqueous and organic layers were partitioned and the aqueous layer was extracted with EtOAc (2×10 mL). The combined organic layers were dried (Na$_2$SO$_4$), filtered and the solvent removed under vacuum to afford a crude residue containing product and carboxylic acid impurity. The residue was purified by column chromatography on silica gel (ISCO Combiflash) using hexanes/EtOAc (1:0 to 0:1) as eluent to give the product (155 mg, 20%) as a solid.

$^1$H NMR (DMSO-d$_6$, 300 MHz): δ 7.14 (s, 2H), 3.79 (s, 6H), 3.67 (s, 3H)

$^{13}$C NMR (DMSO-d$_6$, 75 MHz): δ 153.3, 150.3, 136.6, 130.1, 97.6, 60.2, 56.1 m/z=253.34 [M+H]$^+$ and 251.39 [M−H]$^+$

HRMS (EI): [M+H]$^+$ calc'd for C$_{10}$H$_{12}$N$_4$O$_4$ m/z 253.0937, found 253.0933.

Preparation of 2-(5-oxo-4,5-dihydro-1H-tetrazol-1yl)phenyl acetate 6q

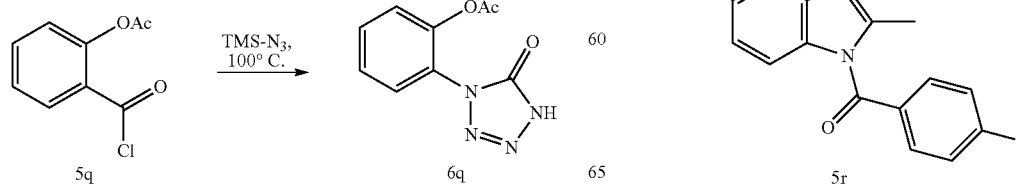

A stirred mixture of azidotrimethylsilane (2.4 mL, 18 mmol) and 2-chlorocarbonyl)phenyl acetate (566 mg, 3.0 mmol) was heated from room temperature to 100° C. (block temperature) in a sealed vial with pressure-release cap. The mixture was then stirred at 100° C. overnight (Note: pressure developed during heating). After cooling, the mixture was concentrated under vacuum and the residue partitioned between EtOAc (10 mL) and a saturated aqueous solution of NaHCO$_3$ (10 mL). The organic layer was extracted with a further quantity of saturated aqueous NaHCO$_3$ (1×10 mL) [note: organic layer was assessed by TLC to ascertain if tetrazolone product was completely removed. If tetrazolone was still present in organic layer, then further extractions with saturated NaHCO$_3$ were used]. EtOAc (20 mL) was added to the combined NaHCO$_3$ layers, and the pH was carefully adjusted to <3 using 6N HCl with efficient stirring. The aqueous and organic layers were partitioned and the aqueous layer was extracted with EtOAc (2×10 mL). The combined organic layers were dried (Na$_2$SO$_4$), filtered and the solvent removed under vacuum to afford a crude residue containing product and other impurities. The residue was purified by column chromatography on silica gel (ISCO Combiflash) using hexanes/EtOAc (1:0 to 0:1) as eluent to give the product (367 mg, 56%) as a solid.

$^1$H NMR (DMSO-d$_6$, 300 MHz): δ 7.66-7.54 (m, 2H), 7.50-7.38 (m, 2H), 2.16 (s, 3H), −1.3 (br. s, 1H)

$^{13}$C NMR (DMSO-d$_6$, 75 MHz): δ 168.2, 150.5, 144.4, 130.5, 126.9, 126.7, 125.4, 124.6, 20.6 m/z=219.45 [M−H]$^+$

HRMS (EI): [M−H]$^+$ calc'd for C$_9$H$_8$N$_4$O$_3$ m/z 219.0518, found 219.0507.

Preparation of 1-((1-(4-chlorobenzoyl)-5-methoxy-1H-indol-3-yl)methyl)-1,4-dihydro-5H-tetrazol-5-one 6r

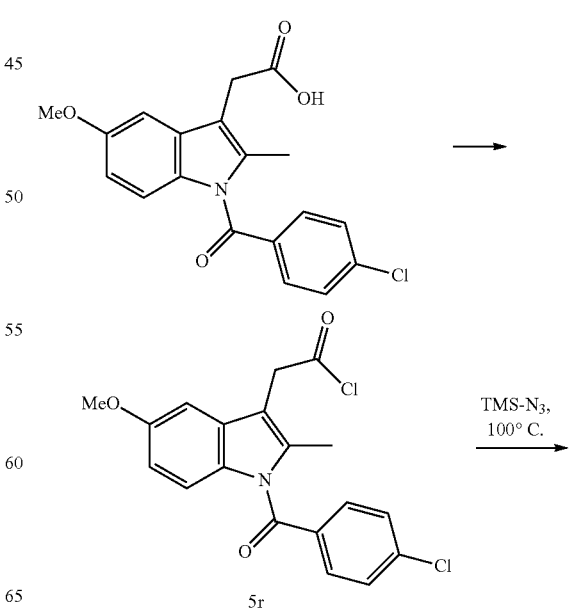

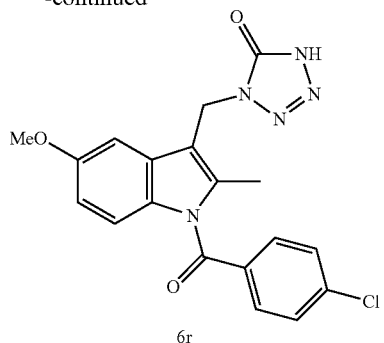

Oxalyl chloride (2.0 M in CH$_2$Cl$_2$; 2.3 mL, 4.6 mmol) was added dropwise over 2-3 min to a stirred suspension of 2-(1-(4-chlorobenzoyl)-5-methoxy-1H-indol-3-yl)acetic acid, also known as Indomethacin (1.07 g, 3.0 mmol) and DMF (1-2 drops) in CH$_2$Cl$_2$ (9 mL) at 0° C. in a vial with pressure-release top. After complete addition, the mixture was allowed to warm to room temperature and stirred at room temperature for ca. 60 min. The mixture was concentrated under vacuum to leave the acid chloride 5r, which was used directly in the tetrazolone-forming step below after drying on a high vacuum for 30 min (yield assumed quantitative=1.13 g).

Note: 4.8 mL (12 equiv.) of azidotrimethylsilane used in order to give sufficient volume for acid chloride to dissolve.

A stirred mixture of azidotrimethylsilane (4.8 mL, 18 mmol) and 2-(1-(4-chlorobenzoyl)-5-methoxy-1H-indol-3-yl)acetyl chloride (1.13 g, 3.0 mmol) was heated from room temperature to 100° C. (block temperature) in a sealed vial with pressure-release cap. The temperature was lowered to 90° C. and the mixture was stirred at 90° C. overnight (Note: pressure developed during heating). After cooling, the mixture was concentrated under vacuum and then the mixture was dry-loaded on to silica gel by evaporation from EtOAc. The mixture was purified by column chromatography on silica gel (ISCO Combiflash) using hexanes/EtOAc (1:0 to 0:1) as eluent to the product (0.98 g, 82%) as a solid.

$^1$H NMR (DMSO-d$_6$, 300 MHz): δ 7.69-7.60 (m, 4H), 7.21 (d, J=2.4 Hz, 1H), 6.89 (d, J=9.0 Hz, 1H), 6.73 (dd, J=9.0, 2.4 Hz, 1H), 5.17 (s, 2H), 3.73 (s, 3H), 2.39 (s, 3H), −1.6 (br. s, 1H)

$^{13}$C NMR (DMSO-d$_6$, 75 MHz): δ 168.0, 155.6, 151.6, 137.9, 137.2, 133.7, 131.3, 130.3, 129.3, 129.1, 114.7, 113.4, 111.6, 101.6, 55.3, 37.1, 13.0 m/z=398.41 [M+H]$^+$ and 396.53 [M−H]$^+$

HRMS (EI): [M+H]$^+$ calc'd for C$_{19}$H$_{16}$ClN$_5$O$_3$ m/z 398.1020, found 398.1034.

HRMS (EI): [M−H]$^+$ calc'd for C$_{19}$H$_{16}$ClN$_5$O$_3$ m/z 396.0863, found 396.0823.

Preparation of 4-(5-oxo-4,5-dihydro-1H-tetrazol-1-yl)-dipropylbenzenesulfonamide 6s

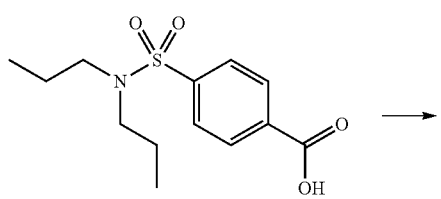

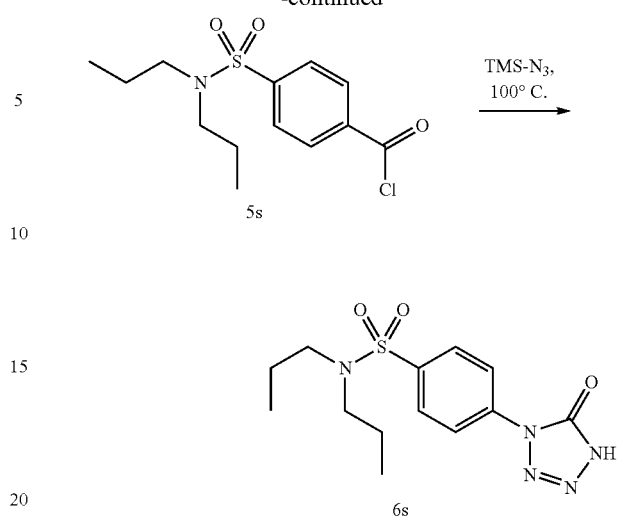

Oxalyl chloride (2.0 M in CH$_2$Cl$_2$; 3.0 mL, 6.0 mmol) was added dropwise over 2-3 min to a stirred suspension of 4-(N,N-dipropylsulfamoyl)benzoic acid (856 mg, 3.0 mmol) and DMF (1-2 drops) in CH$_2$Cl$_2$ (6 mL) at 0° C. under nitrogen. After complete addition, the mixture was allowed to warm to room temperature and stirred overnight. The mixture was concentrated under vacuum to leave the acid chloride 5s, which was used directly in the tetrazolone-forming step below (yield assumed quantitative=911 mg).

A stirred mixture of azidotrimethylsilane (2.4 mL, 18 mmol) and 4-(N,N-dipropylsulfamoyl)benzoyl chloride (911 mg, 3.0 mmol) was heated from room temperature to 100° C. (block temperature) in a sealed vial with pressure-release cap. The mixture was then stirred at 100° C. overnight (Note: pressure developed during heating). After cooling, the mixture was concentrated under vacuum and the residue partitioned between EtOAc (30 mL) and an aqueous saturated NaHCO$_3$ (30 mL). The organic layer was extracted with a further quantity of saturated aqueous NaHCO$_3$ (8×30 mL) [note: organic layer was assessed by TLC to ascertain if tetrazolone product was completely removed. If tetrazolone was still present in organic layer, then further extractions with saturated NaHCO$_3$ were used]. EtOAc (60 mL) was added to the combined NaHCO$_3$ layers, and the pH was carefully adjusted to <3 using 6N HCl with efficient stirring. The aqueous and organic layers were partitioned and the aqueous layer was extracted with EtOAc (2×30 mL). The combined organic layers were dried (Na$_2$SO$_4$), filtered and the solvent removed under vacuum to afford the product (665 mg, 68%) as a solid.

$^1$H NMR (DMSO-d$_6$, 300 MHz): δ 8.13-8.08 (m, 2H), 7.98-7.93 (m, 2H), 3.03 (t, J=7.7 Hz, 2H), 1.47 (app. sextet, J=7.4 Hz, 2H), 0.79 (t, J=7.4 Hz, 3H), −1.1 (br. s, 1H)

$^{13}$C NMR (DMSO-d$_6$, 75 MHz): δ 150.1, 137.8, 137.3, 128.4, 119.0, 49.6, 21.6, 11.0 m/z=326.35 [M+H]$^+$ and 324.43 [M−H]$^+$

HRMS (EI): [M+H]$^+$ calc'd for C$_{13}$H$_{19}$N$_5$O$_3$S m/z 326.1287, found 326.1257.

HRMS (EI): [M−H]$^+$ calc'd for C$_{13}$H$_{19}$N$_5$O$_3$S m/z 324.1130, found 324.1116.

Preparation of 1-(4'-((1,7-dimethyl-2'-propyl-1H,
3'H-[2,5'-dibenzo[d]imidazol]-3'-yl)methyl-[1,1'-
biphenyl-2-yl)-1,4-dihydro-5H-tetrazol-5-one 6t

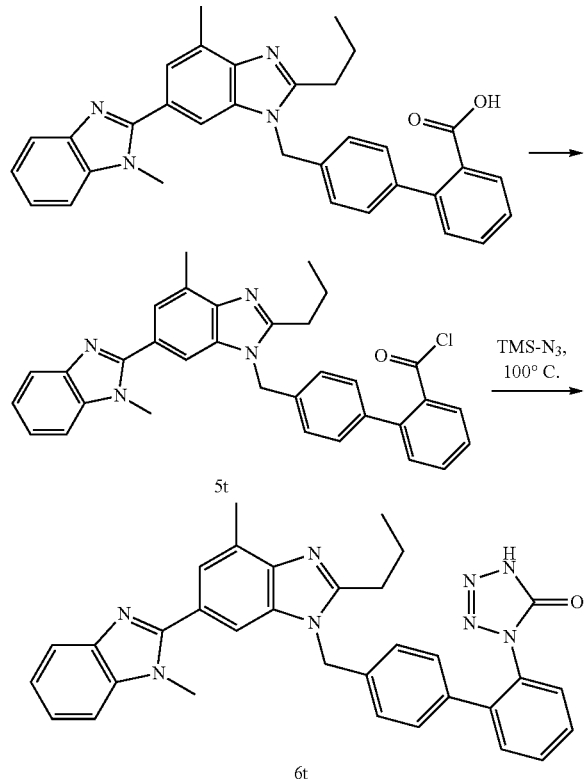

Oxalyl chloride (2.0 M in CH$_2$Cl$_2$; 0.75 mL, 1.5 mmol) was added dropwise over 2-3 min to a stirred suspension of 4'-((1,7-dimethyl-2'-propyl-1H,3'H-[2,5'-dibenzo[d]imidazol]-3'-yl)methyl-[1,1'-biphenyl)-2-carboxylic acid, also known as Telmisartan (514 mg, 1.0 mmol) and DMF (3 drops) in CH$_2$Cl$_2$ (6 mL) at 0° C. under nitrogen. After complete addition, the mixture was stirred at 0° C. for 10 min, then allowed to warm to room temperature and stirred for 30 min (a yellow then orange solution develops). The mixture was concentrated under vacuum, then fresh CH$_2$Cl$_2$ (2 mL) was added to the residue and the mixture concentrated under vacuum again to leave the acid chloride 5t, which was used directly in the tetrazolone-forming step below, after drying on a high vacuum for 15 min (yield assumed quantitative=533 mg).

Note: 4.8 mL (36 equiv.) of azidotrimethylsilane used in order to give sufficient volume for the reaction.

A stirred mixture of azidotrimethylsilane (4.8 mL, 36 mmol) and 4'-((1,7-dimethyl-2'-propyl-1H,3'H-[2,5'-dibenzo[d]imidazol]-3'-yl)methyl-[1,1'-biphenyl)-2-carbonyl chloride (533 mg, 1.0 mmol) was heated from room temperature to 100° C. (block temperature) in a round bottom flask with reflux condenser under an atmosphere of nitrogen. The mixture was then stirred at 100° C. for 2 hours. After cooling, the mixture was concentrated under vacuum and MeOH was added to the residue. The mixture was dry-loaded on to silica gel (ISCO Combiflash) and then purified by column chromatography on silica gel (ISCO Combiflash) using CH$_2$Cl$_2$/MeOH (1:0 to 92:8) as eluent to give the pure product (87 mg) and mixed fractions. The mixed fractions were re-purified by column chromatography on silica gel (ISCO Combiflash) using CH$_2$Cl$_2$/MeOH (1:0 to 92:8) as eluent to give the product (97 mg) as a solid. Total yield of product=184 mg (33%). Also obtained, was a faster-eluting unidentified by-product (181 mg).

$^1$H NMR (DMSO-d$_6$, 300 MHz): δ 7.73 (s, 1H), 7.64-7.47 (m, 7H), 7.29-7.11 (m, 6H), 5.58 (s, 2H), 3.80 (s, 3H), 2.86 (t, J=7.5 Hz, 2H), 2.61 (s, 3H), 1.75 (sextet, J=7.5 Hz, 2H), 0.94 (t, J=7.5 Hz, 3H), −1.5 (br. s, 1H)

$^{13}$C NMR (DMSO-d$_6$, 75 MHz): δ 156.2, 154.0, 151.3, 142.6, 142.4, 139.2, 136.7, 136.7, 136.6, 134.7, 130.9, 130.7, 130.3, 128.8, 128.6, 128.6, 128.3, 126.8, 123.3, 123.2, 122.1, 121.8, 118.6, 110.4, 109.1, 45.9, 31.7, 28.7, 20.7, 16.4, 13.8 m/z=555.66 [M+H]$^+$ and 553.75 [M−H]$^+$

HRMS (EI): [M+H]$^+$ calc'd for C$_{33}$H$_{30}$N$_8$O m/z 555.2621, found 555.2585.

HRMS (EI): [M−H]$^+$ calc'd for C$_{33}$H$_{30}$N$_8$O m/z 553.2465, found 555.2411.

Figure 1B:
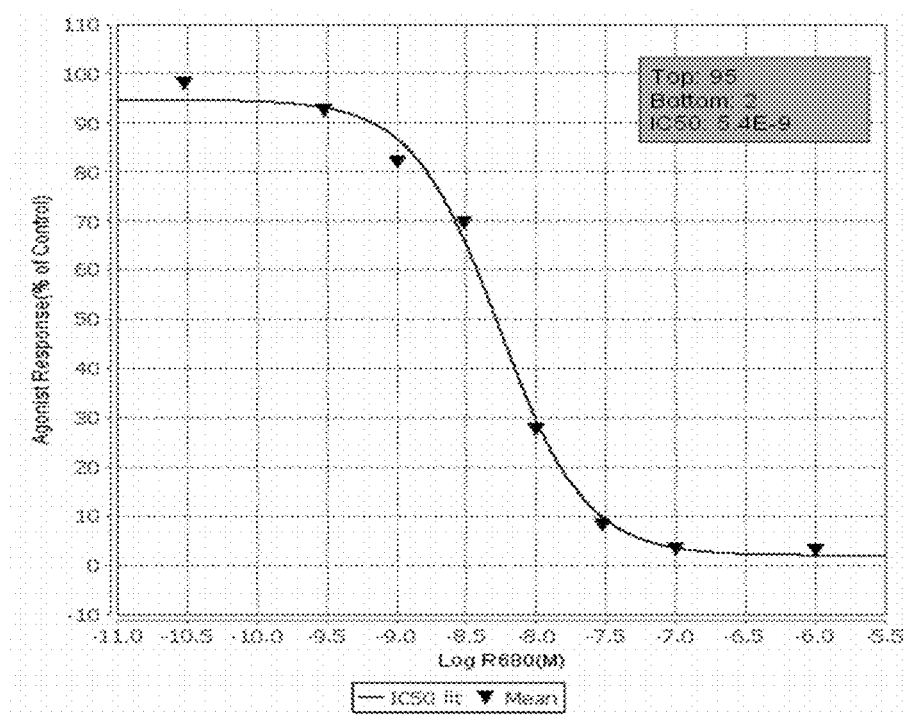
FIG. 1B shows a graph of agonist response (% control) vs. Log concentration (M) for compound 4'-((1,7-dimethyl-2'-propyl-1H,3'H-[2,5'-dibenzo[d]imidazol]-3'-yl)methyl-[1,1'-biphenyl)-2-carboxylic acid (Telmisartan).

The compound 1-(4'-((1,7-dimethyl-2'-propyl-1H,3'H-[2,5'-dibenzo[d]imidazol]-3'-yl)methyl-[1,1'-biphenyl-2-yl)-1,4-dihydro-5H-tetrazol-5-one 6t was tested for angiotensin II receptor type 1 (AT1) antagonist activity. The inhibition of response to 3 nM angiotensin-II for HEK-293 cells expressing hAT1 was assayed. Intracellular [Ca]$^{2+}$ was measured by fluorimetry. The compound 1-(4'-((1,7-dimethyl-2'-propyl-1H,3'H-[2,5'-dibenzo[d]imidazol]-3'-yl)methyl-[1,1'-biphenyl-2-yl)-1,4-dihydro-5H-tetrazol-5-one 6t had an IC$_{50}$=1.7 nM (K$_b$=0.14 nM), as shown in FIG. 1A. For comparison, Telmisartan had an IC$_{50}$=5.4 nM (K$_b$=0.44 nM), as shown in FIG. 1B.

Preparation of 1-(4-(1-(3,5,5,8,8-pentamethyl-5,6,7,
8-tetrahydronaphthalen-2-yl)vinyl)phenyl)-1,4-di-
hydro-5H-tetrazol-5-one 6u

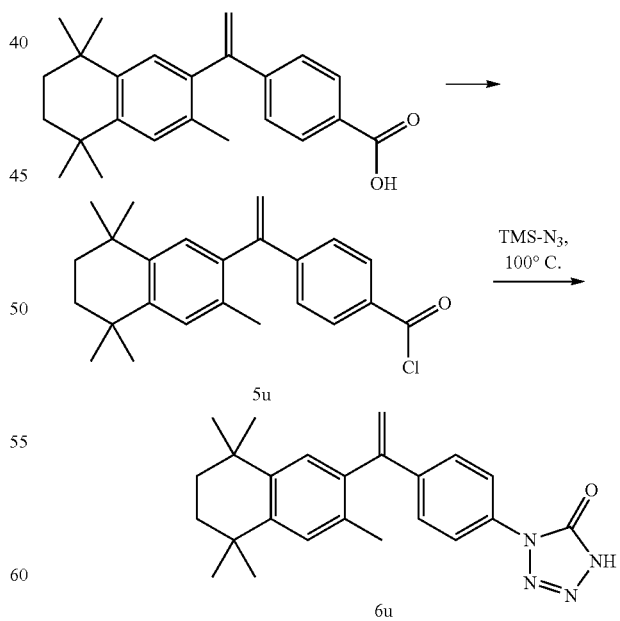

Oxalyl chloride (2.0 M in CH$_2$Cl$_2$; 0.38 mL, 0.75 mmol) was added dropwise over 1 min to a stirred suspension of 4-(1-(3,5,5,8,8-pentamethyl-5,6,7,8-tetrahydronaphthalen-2-yl)vinyl)benzoic acid, also known as Bexarotene (175 mg, 0.5 mmol) and DMF (1-2 drops) in CH$_2$Cl$_2$ (5 mL) at 0° C. under nitrogen. After complete addition, the mixture was allowed to warm to room temperature and for 2 hr. The mixture was concentrated under vacuum to leave the acid chloride 5u, which was used directly in the tetrazolone-forming step below (yield assumed quantitative=184 mg).

Note: 1.0 mL (15 equiv.) of azidotrimethylsilane used in order to give sufficient volume for the reaction.

A stirred mixture of azidotrimethylsilane (1.0 mL, 7.5 mmol) and 4-(1-(3,5,5,8,8-pentamethyl-5,6,7,8-tetrahydronaphthalen-2-yl)vinyl)benzoyl chloride (184 mg, 0.5 mmol) was heated from room temperature to 100° C. (block temperature) in a 10 mL round-bottom flask under an atmosphere of nitrogen. The mixture was then stirred at 100° C. for 2 hr, by which time LC/MS and TLC analysis indicated completion of the reaction. After cooling, CH$_2$Cl$_2$ and MeOH was added to the mixture, which was then dry-loaded on to silica gel and purified by column chromatography on silica gel (ISCO Combiflash) using hexanes/EtOAc (1:0 to 0:1) as eluent to give the product (173 mg, 89%) as a solid.

$^1$H NMR (DMSO-d$_6$, 300 MHz): δ 7.82-7.79 (m, 2H), 7.39-7.36 (m, 2H), 7.13 (s, 1H), 7.06 (s, 1H), 5.84 (s, 1H), 5.18 (s, 1H), 1.91 (s, 3H), 1.63 (br. s, 4H), 1.24 (s, 6H), 1.21 (s, 6H), -1.0 (br. s, 1H)

$^{13}$C NMR (DMSO-d$_6$, 75 MHz): δ 150.2, 147.9, 143.7, 141.8, 138.3, 137.9, 133.4, 132.1, 127.9, 127.3, 127.1, 119.5, 115.9, 34.7, 34.6, 33.6, 33.5, 31.7, 31.6, 19.5 m/z=389.63 [M+H]$^+$ and 387.68 [M-H]$^+$

HRMS (EI): [M+H]$^+$ calc'd for C$_{24}$H$_{28}$N$_4$O m/z 389.2341, found 389.2344.

HRMS (EI): [M-H]$^+$ calc'd for C$_{24}$H$_{28}$N$_4$O m/z 387.2185, found 387.2211.

Compound 1-(4-(1-(3,5,5,8,8-pentamethyl-5,6,7,8-tetrahydronaphthalen-2-yl)vinyl)phenyl)-1,4-dihydro-5H-tetrazol-5-one 6u was tested for agonist activity against retinoid X receptor alpha (RXRα). Activity assays indicated that compound 1-(4-(1-(3,5,5,8,8-pentamethyl-5,6,7,8-tetrahydronaphthalen-2-yl)vinyl)phenyl)-1,4-dihydro-5H-tetrazol-5-one 6u had an EC$_{50}$ hRXRα=64 nM. For comparison, Bexarotene had an EC$_{50}$ hRXRα<10 nM, and fluoro-Bexarotene had an EC$_{50}$ hRXRα=9 nM.

Preparation of 1-(pyridin-3-yl)-1,4-dihydro-5H-tetrazol-5-one 6v

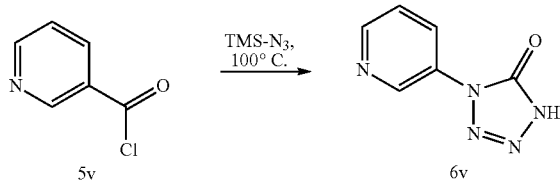 [SMILES: O=C(Cl)c1cccnc1 ; "TMS-N3,100° C." ; O=c1[nH]nnn1-c1cccnc1]

A stirred mixture of azidotrimethylsilane (2.4 mL, 18 mmol) and nicotinoyl chloride (425 mg, 3.0 mmol) was heated from room temperature to 100° C. (block temperature) in a sealed vial with pressure-release cap. The mixture was then stirred at 100° C. overnight (Note: pressure developed during heating). After cooling, the mixture was concentrated under vacuum and the residue partitioned between EtOAc (10 mL) and a saturated aqueous solution of NaHCO$_3$ (10 mL). The organic layer was extracted with a further quantity of saturated aqueous NaHCO$_3$ (1×10 mL) [note: organic layer was assessed by TLC to ascertain if tetrazolone product was completely removed. If tetrazolone was still present in organic layer, then further extractions with saturated NaHCO$_3$ were used]. EtOAc (20 mL) was added to the combined NaHCO$_3$ layers, and the pH was adjusted to <3 using 6N HCl with efficient stirring. Once acidified, the aqueous layer was re-adjusted to pH 6-7 using saturated NaHCO$_3$. The aqueous and organic layers were partitioned and the aqueous layer was extracted with EtOAc (2×10 mL). The combined organic layers were dried (Na$_2$SO$_4$), filtered and the solvent removed under vacuum to afford the product (330 mg, 65%) as a solid. A sample was recrystallized from EtOAc.

$^1$H NMR (DMSO-d$_6$, 300 MHz): δ 9.04 (d, J=2.1 Hz, 1H), 8.60 (d, J=4.5 Hz, 1H), 8.22 (ddd, J=8.4, 2.7, 1.5 Hz, 1H), 7.58 (dd, J=8.4, 4.8, Hz, 1H), -1.1 (br. s, 1H)

$^{13}$C NMR (DMSO-d$_6$, 75 MHz): δ 150.4, 148.5, 140.7, 131.1, 127.1, 12.2 m/z=162.20 [M-H]$^+$

HRMS (EI): [M+H]$^+$ calc'd for C$_6$H$_5$N$_5$O m/z 164.0572, found 164.0542.

Preparation of 1-(3-chlorothiophen-2-yl)-1,4-dihydro-5H-tetrazol-5-one 6w

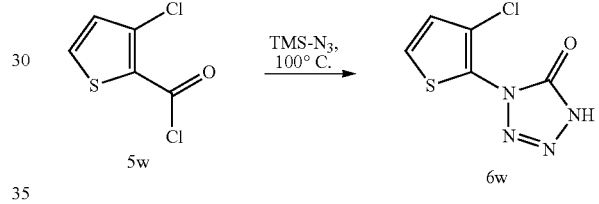

A stirred mixture of azidotrimethylsilane (2.4 mL, 18 mmol) and 3-chlorothiophene-2-carbonyl chloride (543 mg, 3.0 mmol) was heated from room temperature to 100° C. (block temperature) in a sealed vial with pressure-release cap. The mixture was then stirred at 100° C. overnight (Note: pressure developed during heating). After cooling, the mixture was concentrated under vacuum and the residue partitioned between EtOAc (10 mL) and a saturated aqueous solution of NaHCO$_3$ (10 mL). The organic layer was extracted with a further quantity of saturated aqueous NaHCO$_3$ (1×10 mL) [note: organic layer was assessed by TLC to ascertain if tetrazolone product was completely removed. If tetrazolone was still present in organic layer, then further extractions with saturated NaHCO$_3$ were used]. EtOAc (20 mL) was added to the combined NaHCO$_3$ layers, and the pH was adjusted to <3 using 6N HCl with efficient stirring. The aqueous and organic layers were partitioned and the aqueous layer was extracted with EtOAc (2×10 mL). The combined organic layers were dried (Na$_2$SO$_4$), filtered and the solvent removed under vacuum to afford a mixture of the desired product and 3-chlorothiophene-2-carboxylic acid. This mixture was purified by column chromatography on silica gel (ISCO Combiflash) using hexanes/EtOAc (1:0 to 0:1) as eluent to give the product (185 mg, 30%) as a solid [also obtained from the column was 3-chlorothiophene-2-carboxylic acid (20 mg)].

$^1$H NMR (DMSO-d$_6$, 300 MHz): δ 7.88 (d, J=6.0 Hz, 1H), 7.25 (d, J=6.0 Hz, 1H), -1.1 (br. s, 1H)

$^{13}$C NMR (DMSO-d$_6$, 75 MHz): δ 150.5, 128.0, 126.6, 125.8, 123.6 m/z=203.26 [M+H]$^+$ and 201.37 [M-H]$^+$

HRMS (EI): [M−H]+ calc'd for C5H3ClN4OS m/z 200.9638, found 200.9674.

Preparation of 1-(3-(2-chlorophenyl)5-methylisoxazol-4-yl)-1,4-dihydro-5H-tetrazol-5-one 6x

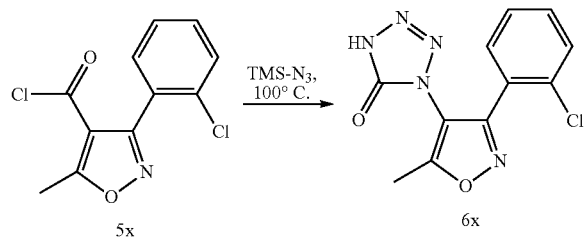 [SMILES: Cc1onc(-c2ccccc2Cl)c1C(=O)Cl ; "TMS-N3,100° C." ; Cc1onc(-c2ccccc2Cl)c1-n1nn[nH]c1=O]

A stirred mixture of azidotrimethylsilane (2.4 mL, 18 mmol) and 3-(2-chlorophenyl)-5-methylisoxazole-4-carbonyl chloride (768 mg, 3.0 mmol) was heated from room temperature to 100° C. (block temperature) in a sealed vial with pressure-release cap. The mixture was then stirred at 100° C. overnight (Note: pressure developed during heating). After cooling, the mixture was concentrated under vacuum and the residue partitioned between EtOAc (10 mL) and a saturated aqueous solution of NaHCO3 (10 mL). The organic layer was extracted with a further quantity of saturated aqueous NaHCO3 (1×10 mL) [note: organic layer was assessed by TLC to ascertain if tetrazolone product was completely removed. If tetrazolone was still present in organic layer, then further extractions with saturated NaHCO3 were used]. EtOAc (20 mL) was added to the combined NaHCO3 layers, and the pH was adjusted to <3 using 6N HCl with efficient stirring. The aqueous and organic layers were partitioned and the aqueous layer was extracted with EtOAc (2×10 mL). The combined organic layers were dried (Na2SO4), filtered and the solvent removed under vacuum to afford the product (713 mg, 86%) as a solid. A sample was recrystallized from EtOAc.

1H NMR (DMSO-d6, 300 MHz): δ 7.58-7.44 (m, 4H), 2.55 (s, 3H), −1.2 (br. s, 1H)

13C NMR (DMSO-d6, 75 MHz): δ 167.4, 157.9, 150.8, 132.7, 132.1, 130.3, 128.2, 126.2, 115.5, 111.6 m/z=278.36 [M+H]+ and 276.51 [M−H]+

HRMS (EI): [M+H]+ calc'd for C11H8ClN5O2 m/z 278.0445, found 278.0450.

Preparation of methyl (E)-3-(5-oxo-4,5-dihydro-1H-tetrazol-1-yl)acrylate 6y

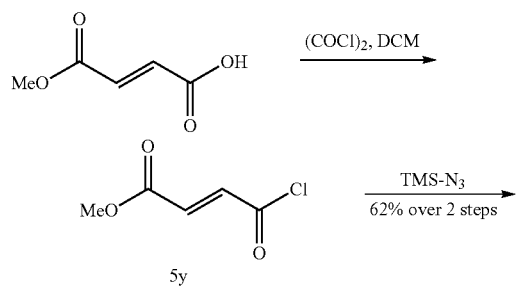

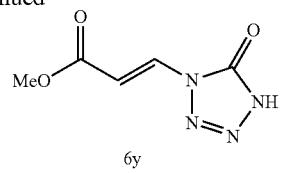

Oxalyl chloride (2.0 M in CH2Cl2; 15.2 mL, 30.3 mmol) was added dropwise over 2-3 min to a stirred suspension of monomethyl fumarate (2.63 g, 20.2 mmol) in CH2Cl2 (80 mL) at 0° C. under nitrogen. After complete addition, the mixture was stirred at 0° C. for 5 min then allowed to warm to room temperature and stirred for 3 hr (a yellow solution developed). A small aliquot was removed and quenched with MeOH—TLC indicated no acid remaining. The mixture was concentrated under vacuum and CH2Cl2 (50 mL) was added to the residue and the mixture concentrated under vacuum once more to leave the acid chloride 5w, which was used directly in the tetrazolone-forming step below (yield assumed quantitative=3.0 g).

Azidotrimethylsilane (16.1 mL, 121.2 mmol) was added in one portion to the acid chloride from the above procedure (3.0 g, 20.2 mmol) at room temperature (gas evolution was noted). The mixture was place under nitrogen and heated from room temperature to 100° C. (block temperature), then stirred at 100° C. for 90 min. After cooling to room temperature, the excess solvent was removed under vacuum to leave a crude residue. EtOAC (150 mL) and saturated NaHCO3 (150 mL) were added to the residue. A solid was noticed, so the mixture was filtered. The filter cake was dissolved in H2O (350 mL) and then combined with the saturated NaHCO3 layer of the filtrate. EtOAc (150 mL) was added to the combined aqueous system described above, and the mixture was acidified to ca. pH 3 with 1N HCl. The aqueous and organic layers were partitioned and the aqueous layer was extracted with EtOAc (2×100 mL). The combined organic extracts were dried (Na2SO4), filtered and the solvent removed under vacuum to leave a crude residue (2.6 g; ca. 90% purity of desired product). The residue was purified by column chromatography on silica gel using CH2Cl2/MeOH (1:0 to 9:1) as eluent to give the product (2.14 g, 62% over 2 steps) as a solid.

1H NMR (DMSO-d6, 300 MHz): δ 7.73 (d, J=14.4 Hz, 1H), 6.49 (d, J=14.4 Hz, 1H), 3.71 (s, 3H),−1.0 (br. s, 1H)

13C NMR (DMSO-d6, 75 MHz): δ 165.7, 149.8, 132.3, 106.3, 51.9 m/z=169.34 [M−H]+

HRMS (EI): [M+H]+ calc'd for C5H6N4O3 m/z 171.0518, found 171.0522.

Preparation of 1-ethyl-1,4-dihydro-5H-tetrazol-5-one 6z

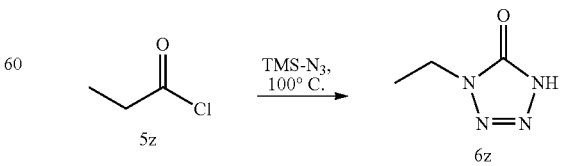

A stirred mixture of azidotrimethylsilane (2.4 mL, 18 mmol) and propionyl chloride (278 mg, 3.0 mmol) was heated from room temperature to 100° C. (block temperature) in a sealed vial with pressure-release cap. The mixture was then stirred at 100° C. overnight (Note: pressure developed during heating). After cooling, the mixture was concentrated under vacuum and the residue partitioned between EtOAc (10 mL) and a saturated aqueous solution of NaHCO$_3$ (10 mL). The organic layer was extracted with a further quantity of saturated aqueous NaHCO$_3$ (1×10 mL) [note: organic layer was assessed by TLC to ascertain if tetrazolone product was completely removed. If tetrazolone was still present in organic layer, then further extractions with saturated NaHCO$_3$ were used]. EtOAc (20 mL) was added to the combined NaHCO$_3$ layers, and the pH was adjusted to <3 using 6N HCl with efficient stirring. The aqueous and organic layers were partitioned and the aqueous layer was extracted with EtOAc (2×10 mL). The combined organic layers were dried (Na$_2$SO$_4$), filtered and the solvent removed under vacuum to afford the product (49 mg, 14%) as a solid.

$^1$H NMR (DMSO-d$_6$, 300 MHz): δ 3.86 (q, J=7.3 Hz, 2H), 1.26 (t, J=7.3 Hz, 3H), −1.7 (br. s, 1H)

$^{13}$C NMR (DMSO-d$_6$, 75 MHz): δ 151.6, 38.7, 13.7

Example 2

Reactions were performed to form tetrazolone derivatives of active agents having a carboxyl group, where a tetrazolone group served as a bioisostere of the carboxyl group.

Preparation of (Z)-1-(3'-(2-(1-(3,4-dimethylphenyl)-3-methyl-5-oxo-1,5-dihydro-4H-pyrazol-4-ylidene)hydrazinyl)-2'-hydroxy-[1,1'-biphenyl]-3-yl)-1,4-dihydro-5H-tetrazol-5-one

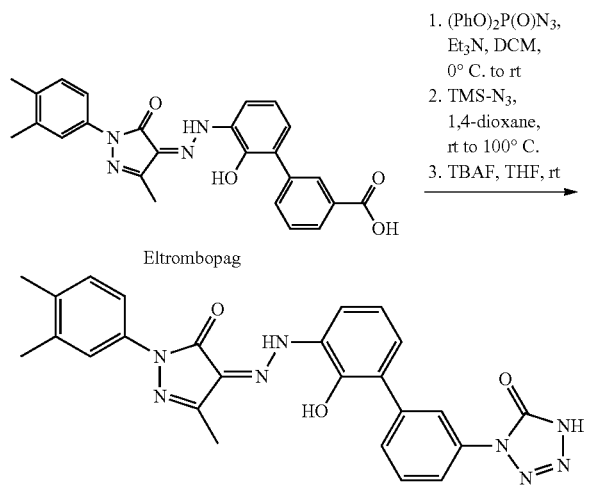

Eltrombopag

Diphenyl phosphoryl azide (196 μL, 0.9 mmol) was added to a stirred solution of Eltrombopag (365 mg, 0.83 mmol) and Et$_3$N (140 μL, 1.0 mmol) in CH$_2$Cl$_2$ (10 mL) at 0° C. under an atmosphere of nitrogen. The mixture was stirred at 0° C. for 2 min, then allowed to warm to room temperature and stirred for 2 hr. Further aliquots of diphenyl phosphoryl azide (196 μL, 0.9 mmol) and Et$_3$N (140 μL, 1.0 mmol) were added and the mixture was stirred at room temperature overnight. H$_2$O (15 mL) and CH$_2$Cl$_2$ (10 mL) were added and the aqueous and organic layers were partitioned. The aqueous layer was extracted with CH$_2$Cl$_2$ (1×20 mL), and the combined organic layers were dried over Na$_2$SO$_4$, filtered and the solvent removed under vacuum to leave a crude solid.

The solid was suspended in azidotrimethylsilane (10 mL), placed under a nitrogen atmosphere and then slowly heated from room temperature to 100° C. The mixture was stirred at 100° C. for 10 min. As the mixture was still a suspension, it was removed from the heat and allowed to cool. 1,4-Dioxane (10 mL) was added and the mixture was returned to the heat block and a solution formed. The mixture was stirred at 100° C. under nitrogen for 6 hr. The solvent was removed under vacuum [note: at this stage LC/MS indicated that the phenol had been protected as a TMS ether]. The mixture was suspended in THF (10 mL) and a 1N solution of tetrabutylammonium fluoride in THF (1 mL) was added, and the mixture was stirred at room temperature for 1 hr. The mixture was dry-loaded on to silica gel and was purified by column chromatography on silica gel using DCM/(MeOH/AcOH) as eluent. While collecting fractions, some solid product had precipitated in some fractions. The main fractions were filtered and the filter cake was washed with MeOH to afford the desired product (155 mg, 40%) as a solid.

$^1$H NMR (DMSO-d$_6$, 300 MHz): δ 13.72 (br. s, 1H), 9.72 (br. s, 1H), 8.06 (s, 1H), 7.84 (d, J=7.8 Hz, 1H), 7.72-7.58 (m, 5H), 7.19-7.10 (m, 3H), 2.20 (s, 3H), 2.24 (s, 3H), 2.20, (s, 3H), −1.18 (br. s, 1H)

m/z=483.22 [M+H]$^+$ and 481.26 [M−H]$^+$

HRMS (EI): [M+H]$^+$ calc'd for C$_{25}$H$_{22}$N$_8$O$_3$ m/z 483.1868, found 481.1893.

HRMS (EI): [M−H]$^+$ calc'd for C$_{25}$H$_{22}$N$_8$O$_3$ m/z 481.1741, found 481.1737.

Preparation of 9-methyl-3-(5-oxo-4,5-dihydro-1H-tetrazol-1-yl)-4H-pyrido[1,2-a]pyrimidin-4-one

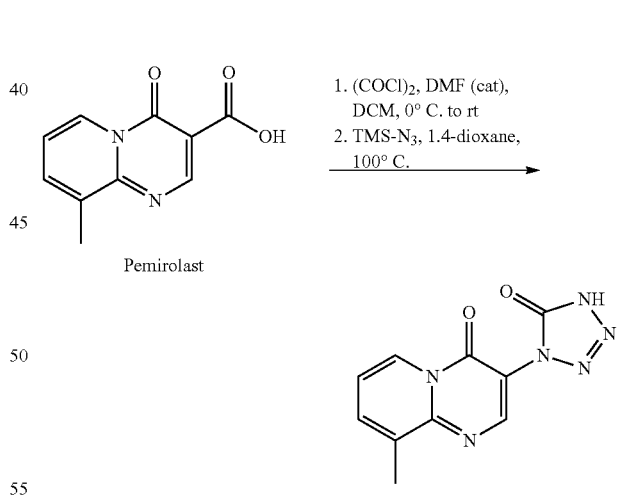

Pemirolast

Oxalyl chloride (2.0 M in CH$_2$Cl$_2$; 1.0 mL, 2.0 mmol) was added to a stirred suspension of Pemirolast (204 mg, 1.0 mmol) in CH$_2$Cl$_2$ (5 mL) at 0° C. under an atmosphere of nitrogen. The mixture was allowed to warm to room temperature and stirred overnight. An analytical sample was removed and quenched with MeOH. Analysis of the sample by LC/MS indicated a complete reaction. The mixture was concentrated under vacuum to leave a crude residue.

The residue was suspended in 1,4-dioxane (5 mL) and azidotrimethylsilane (5 mL) and placed under an atmosphere of nitrogen. The mixture was then slowly heated from room temperature to 100° C. and stirred at 100° C. for 4 hr. The mixture was cooled, and dry-loaded on to silica gel. Purification by silica gel chromatography using CH$_2$Cl$_2$/MeOH (1:0 to 9:1) as eluent gave the desired product (41 mg, 18%) as a solid [note: mixed fractions containing product were not isolated].

$^1$H NMR (DMSO-d$_6$, 300 MHz): δ 8.94 (dd, J=7.1, 0.6 Hz, 1H), 8.68 (d, J=0.6 Hz, 1H), 8.02 (d, J=7.1 Hz, 1H), 7.45 (app. t, J=7.1 Hz, 1H), 2.56 (s, 3H), −1.32 (br. s, 1H)
m/z=245.10 [M+H]$^+$ and 243.18 [M−H]$^+$ HRMS (EI): [M+H]$^+$ calc'd for C$_{10}$H$_8$N$_6$O$_2$ m/z 245.0776, found 245.0787.

HRMS (EI): [M−H]$^+$ calc'd for C$_{10}$H$_8$N$_6$O$_2$ m/z 243.0634, found 243.0630.

Preparation of (S)-9-fluoro-3-methyl-10-(4-methyl-piperazin-1-yl)-6-(5-oxo-4,5-dihydro-1H-tetrazol-1-yl)-2,3-dihydro-7H-[1,4]oxazino[2,3,4-ij]quinolin-7-one

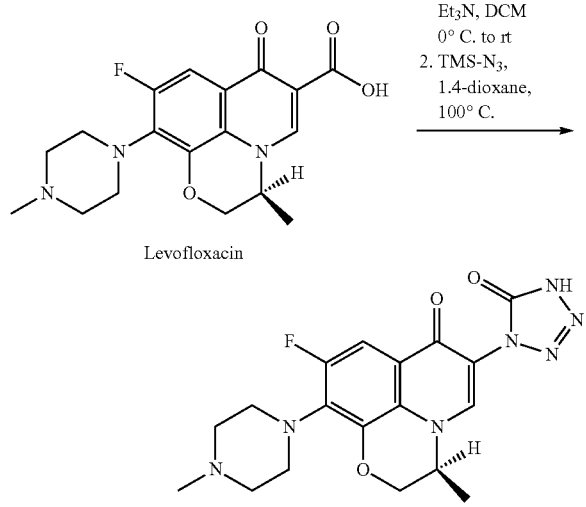

Diphenyl phosphoryl azide (323 µL, 1.5 mmol) was added to a stirred solution of Levofloxacin (361 mg, 1.0 mmol) and Et$_3$N (280 µL, 2.0 mmol) in CH$_2$Cl$_2$ (10 mL) at 0° C. under an atmosphere of nitrogen. The mixture was stirred at 0° C. for 15 min, then allowed to warm to room temperature and stirred for 4 hr. Further aliquots of diphenyl phosphoryl azide (323 µL, 1.0 mmol) and Et$_3$N (280 µL, 2.0 mmol) were added and the mixture was stirred at room temperature overnight. H$_2$O (20 mL) and CH$_2$Cl$_2$ (15 mL) were added and the aqueous and organic layers were partitioned. The aqueous layer was extracted with CH$_2$Cl$_2$ (2×20 mL), and the combined organic layers were dried over Na$_2$SO$_4$, filtered and the solvent was removed under vacuum to leave a crude residue.

The residue was suspended in azidotrimethylsilane (5 mL) and 1,4-dioxane (5 mL), then placed under an atmosphere of nitrogen. The mixture was slowly heated from room temperature to 100° C., and then stirred at 100° C. for 4 hr. After cooling, the mixture was dry-loaded on to silica gel and purified by column chromatography on silica gel using CHCl$_3$/(MeOH/NH$_4$OH; 7:1) [1:0 to 7:3] as eluent to give the product as a solid.

$^1$H NMR (DMSO-d$_6$, 300 MHz): δ 8.51 (s, 1H), 7.39 (d, J=12.3 Hz, 1H), 4.62-4.54 (m, 1H), 4.47 (dd, J=11.4, 1.5 Hz, 1H), 4.34 (dd, J=11.4, 2.1 Hz, 1H), 3.25 (br. s, 8H), 2.24 (s, 3H), 1.41 (d, J=6.3 Hz, 3H)

$^{19}$F NMR (DMSO-d$_6$, 282 MHz): δ −122.9 (d, J=12.3 Hz)
m/z=402.91 [M+H]$^+$

HRMS (EI): [M+H]$^+$ calc'd for C$_{10}$H$_8$N$_6$O$_2$ m/z 402.1701, found 402.1690.

HRMS (EI): [M−H]$^+$ calc'd for C$_{10}$H$_8$N$_6$O$_2$ m/z 400.1527, found 400.1534.

Preparation of 4-hydroxy-1-methyl-N-((5-oxo-4,5-dihydro-1H-tetrazol-1-yl)methyl)-7-phenoxyisoquinoline-3-carboxamide

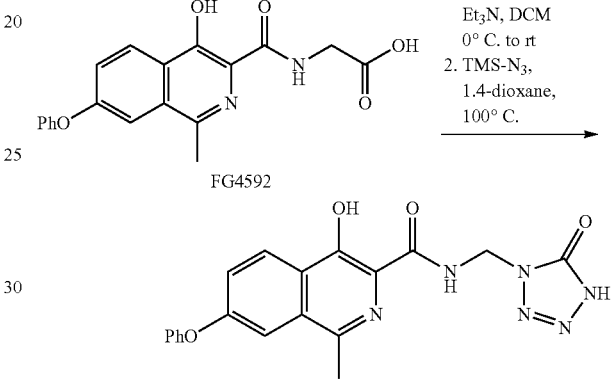

Diphenyl phosphoryl azide (216 µL, 1.0 mmol) was added to a stirred solution of FG4592 (177 mg, 0.5 mmol) and Et$_3$N (210 µL, 1.5 mmol) in CH$_2$Cl$_2$ (5 mL) at 0° C. under an atmosphere of nitrogen. The mixture was stirred at 0° C. for 15 min, then allowed to warm to room temperature and stirred at room temperature overnight. H$_2$O (20 mL) and CH$_2$Cl$_2$ (15 mL) were added and the aqueous and organic layers were partitioned. The aqueous layer was extracted with CH$_2$Cl$_2$ (1×20 mL), and the combined organic layers were dried over Na$_2$SO$_4$, filtered and the solvent was removed under vacuum to leave a crude residue.

The residue was suspended in azidotrimethylsilane (5 mL) and 1,4-dioxane (5 mL), then placed under an atmosphere of nitrogen. The mixture was slowly heated from room temperature to 100° C., and then stirred at 100° C. overnight. After cooling, the mixture was dry-loaded on to silica gel and purified by column chromatography on silica gel to give the product (85 mg, 43%) as a solid.

$^1$H NMR (DMSO-d$_6$, 300 MHz): δ 13.19 (s, 1H), 9.20 (t, J=6.3 Hz, 1H), 8.68 (t, J=5.7 Hz, 1H), 8.27 (d, J=9.0 Hz, 1H), 7.59 (d, J=2.4 Hz, 1H), 7.54-7.43 (m, 3H), 7.24 (tt, J=7.5, 1.2 Hz, 1H), 7.18-7.14 (m, 2H), 4.72 (t, J=6.0 Hz, 2H), 2.67 (s, 3H)

$^{13}$C NMR (DMSO-d$_6$, 75 MHz): δ 169.8, 157.9, 156.1, 155.5, 153.1, 147.0, 131.5, 130.4, 125.3, 124.6, 123.4, 122.5, 119.5, 119.2, 112.1, 45.2, 21.4 m/z=393.17 [M+H]$^+$ & 391.20 [M−H]$^+$

HRMS (EI): [M+H]$^+$ calc'd for C$_{19}$H$_{16}$N$_6$O$_4$ m/z 393.1311, found 393.1327.

HRMS (EI): [M−H]$^+$ calc'd for C$_{19}$H$_{16}$N$_6$O$_4$ m/z 391.1529, found 391.1155.

Preparation of (E)-4-(2-(4-oxo-3-(3-(5-oxo-4,5-dihydro-1H-tetrazol-1-yl)phenyl)-3,4-dihydroquinazolin-2-yl)vinyl)benzonitrile

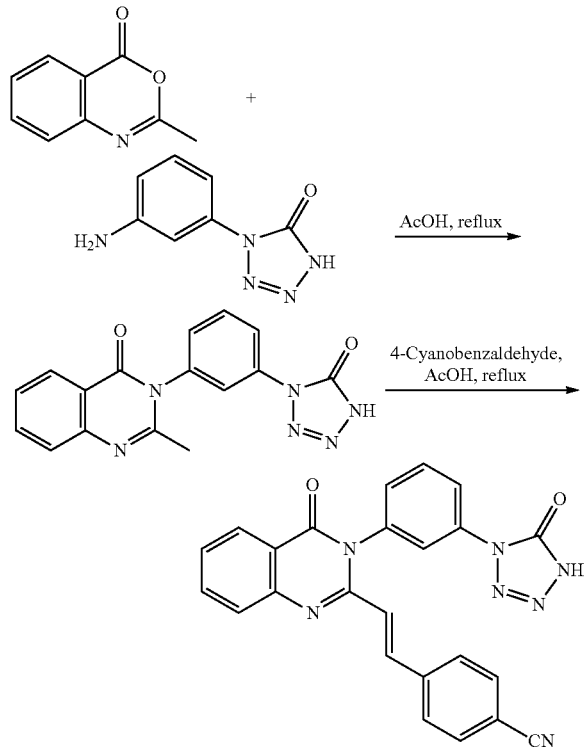

Preparation of 1-(3-aminophenyl)-1,4-dihydro-5H-tetrazol-5-one

A mixture of 1-(3-nitrophenyl)-1,4-dihydro-5H-tetrazol-5-one (130 mg, 0.63 mmol) and palladium on charcoal (Aldrich Cat. No. 330108; 13 mg) in MeOH (10 mL) was hydrogenated at 20 psi for 3 hr. The mixture was then filtered through celite and the filter cake washed with MeOH (×3). The filtrate was concentrated under vacuum to leave the product, which was used directly in the next step (yield assumed quantitative=111 mg).

rt=1.43 min; m/z=178.11 [M+H]$^+$ & 176.16 [M–H]$^+$

Preparation of 2-methyl-3-(3-(5-oxo-4,5-dihydro-1H-tetrazol-yl)phenyl)quinazolin-4(3H)-one A mixture of 2-methyl-4H-benzo[d][1,3]oxazin-4-one (101 mg, 0.63 mmol) and 1-(3-aminophenyl)-1,4-dihydro-5H-tetrazol-5-one (111 mg, 0.63 mmol) in AcOH (10 mL) was heated to reflux and stirred overnight. Analysis indicated the formation of product. The mixture was allowed to cool and dry-loaded onto silica gel. The mixture was purified by column chromatography on silica gel using CH$_2$Cl$_2$/MeOH (1:0 to 9:1) as eluent to give the product (32 mg, 16% ca. 94% purity by LC/MS). The product was used directly in the next step.

rt=3.88 min; m/z=321.15 [M+H]$^+$ & 319.23 [M–H]$^+$

Preparation of (E)-4-(2-(4-oxo-3-(3-(5-oxo-4,5-dihydro-1H-tetrazol-1-yl)phenyl)-3,4-dihydroquinazolin-2-yl)vinyl)benzonitrile A mixture of 2-methyl-3-(3-(5-oxo-4,5-dihydro-1H-tetrazol-1-yl)phenyl)quinazolin-4(3H)-one (32 mg, 0.1 mmol) and 4-cyanobenzaldehyde (16 mg, 0.12 mmol) in AcOH (5 mL) was heated to reflux and stirred for 3 days (continuously monitored by LC/MS, which indicated product formation after 3 hr). After cooling, the mixture was dry-loaded onto silica gel and purified by column chromatography on silica gel using CH$_2$Cl$_2$/MeOH (1:0 to 95:5) as eluent to give a solid (11 mg; desired product ca. 70% purity). The solid was re-purified by preparative thin-layer chromatography using CH$_2$Cl$_2$/MeOH (9:1) as eluent to give the product (6 mg, 14%) as a solid.

rt=5.95 min; m/z=434.19 [M+H]$^+$ & 432.23 [M–H]$^+$ $^1$H NMR (CD$_3$OD; 300 MHz): δ 8.15-8.09 (m, 2H), 8.01 (t, J=2.0 Hz, 1H), 7.83 (d, J=15.5 Hz, 1H), 7.82-7.71 (m, 2H), 7.64 (t. J=8.0 Hz, 1H), 7.55 (d, J=8.7 Hz, 2H). 7.49-7.42 (m, 3H), 7.24 (ddd, J=7.8, 2.7, 0.9 Hz, 1H), 6.54 (d, J=15.5 Hz, 1H)

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating a disease or disorder in a subject in need of treatment, the method comprising administering to the subject a compound comprising a tetrazolone derivative of a carboxyl group of an active agent wherein said compound is of formula:

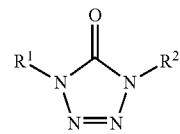

wherein

R1 is the active agent; and

R2 is selected from hydrogen, alkyl, substituted alkyl, alkenyl, substituted alkenyl, alkynyl, substituted alkynyl, cycloalkyl, substituted cycloalkyl, aryl, substituted aryl, heteroaryl, and substituted heteroaryl; or a salt or stereoisomer thereof.

2. The method of claim 1, wherein R$^2$ is hydrogen or alkyl.

3. A The method of claim 1, wherein the active agent is a therapeutically effective active agent.

4. The method of claim 1, wherein the tetrazolone derivative is produced from the carboxyl group of the active agent.

5. The method of claim 1, wherein the compound is selected from:

97
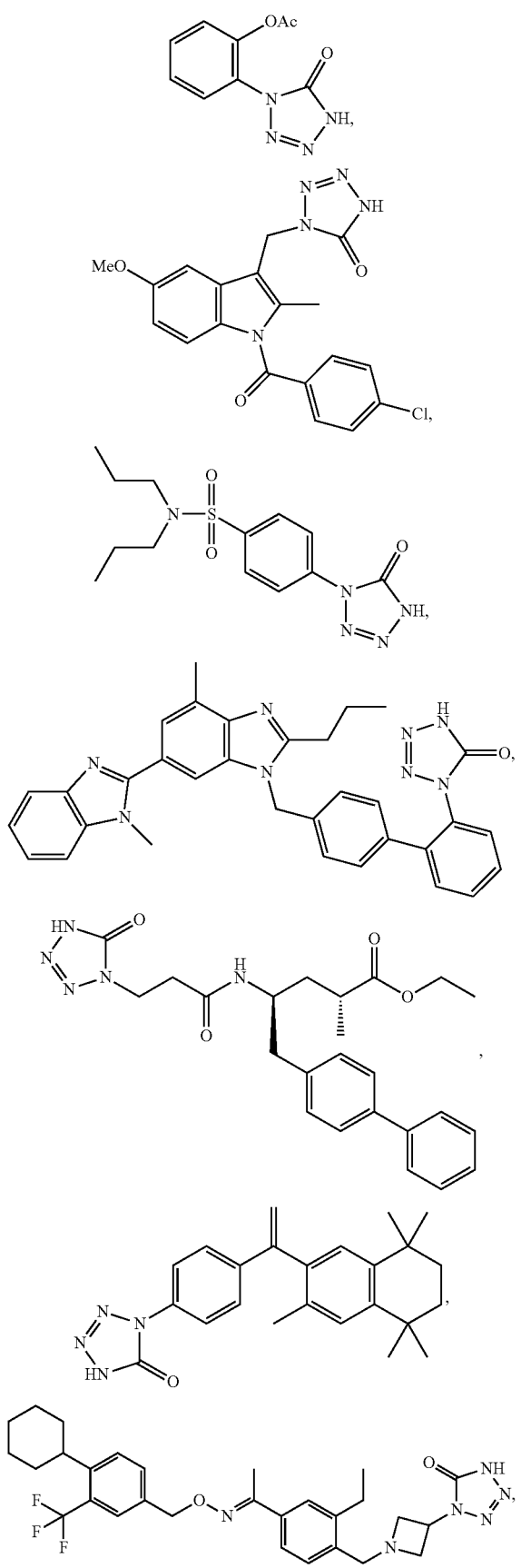
98
-continued
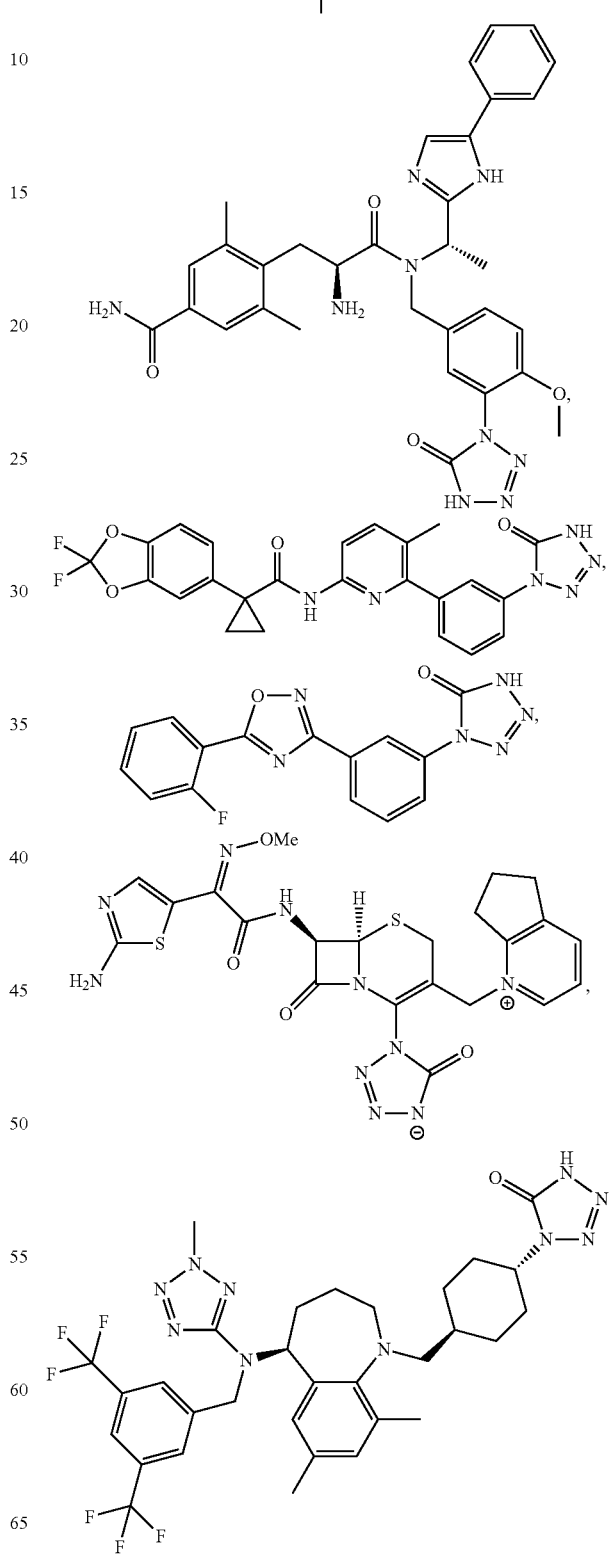

99
-continued
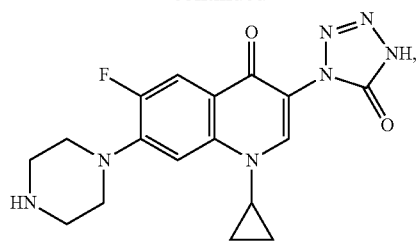
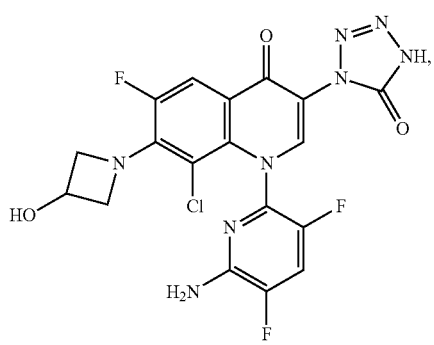
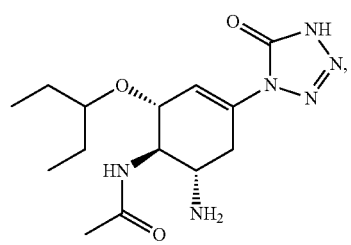
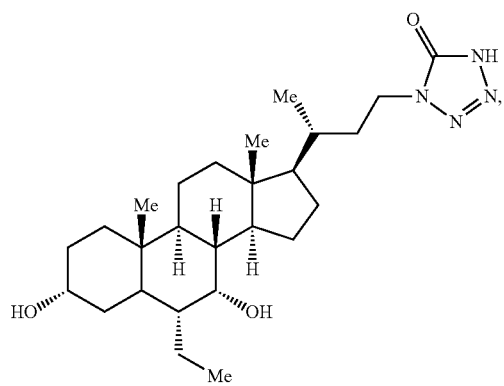
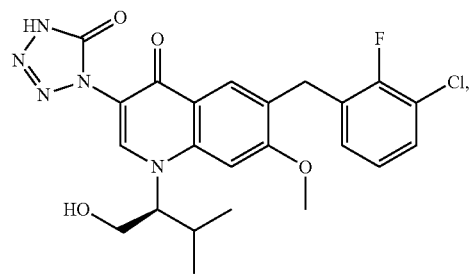
100
-continued
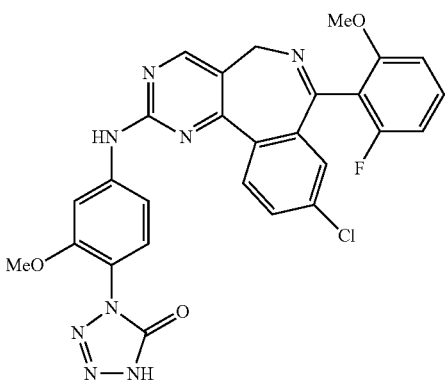
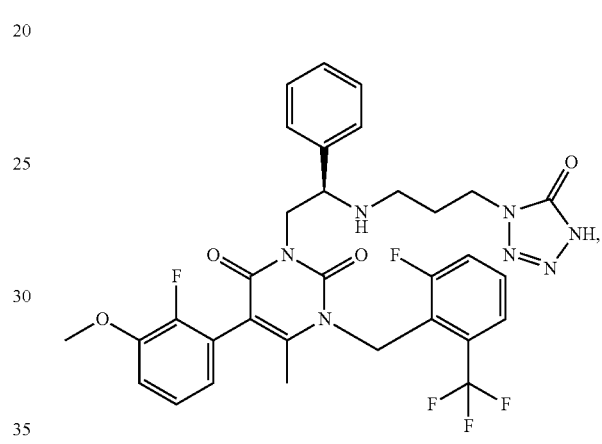
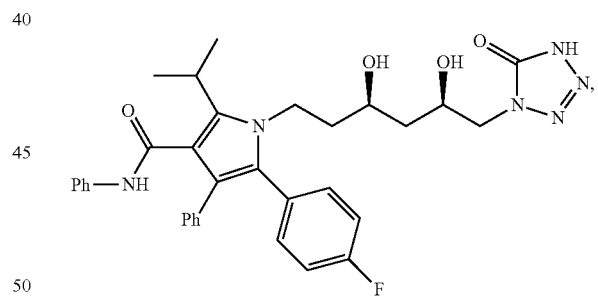
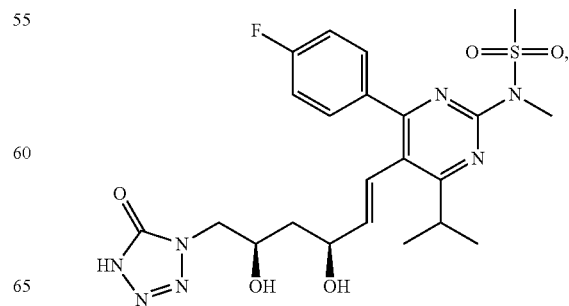

101
-continued
102
-continued
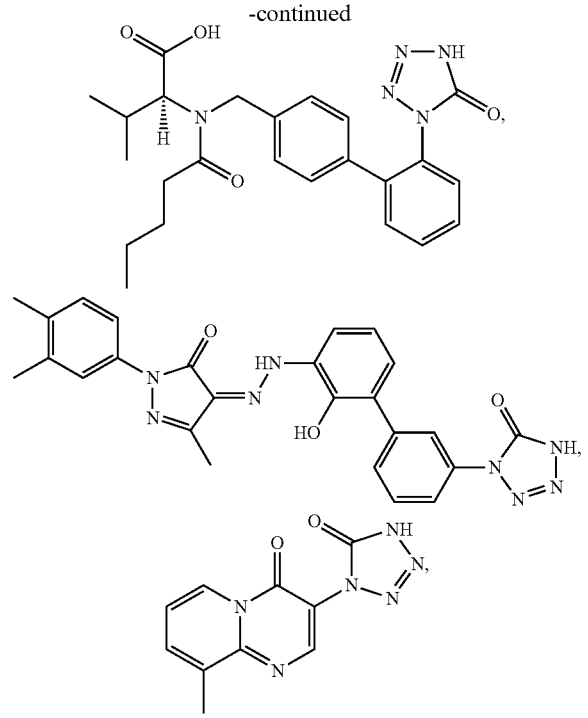
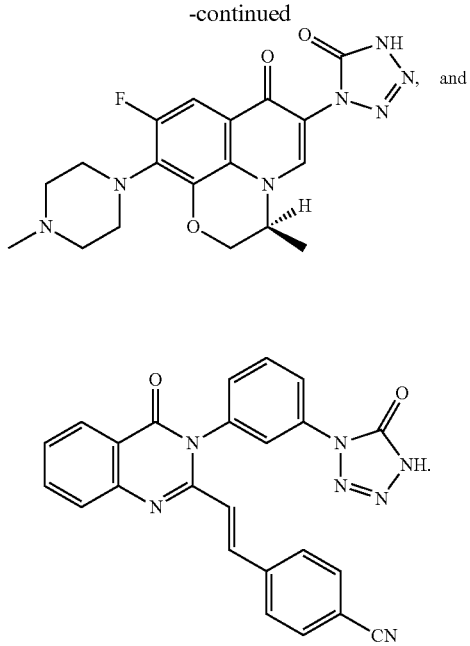
* * * * *